(12) United States Patent
Linden et al.

(10) Patent No.: US 7,427,606 B2
(45) Date of Patent: *Sep. 23, 2008

(54) METHOD TO REDUCE INFLAMMATORY RESPONSE IN TRANSPLANTED TISSUE

(75) Inventors: Joel M. Linden, Charlottesville, VA (US); Kenneth Brayman, Charlottesville, VA (US); Gail W. Sullivan, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 160 days.

This patent is subject to a terminal disclaimer.

(21) Appl. No.: 11/002,008

(22) Filed: Dec. 2, 2004

(65) Prior Publication Data

US 2005/0182018 A1 Aug. 18, 2005

Related U.S. Application Data

(63) Continuation-in-part of application No. 10/379,154, filed on Mar. 3, 2003, which is a continuation of application No. 09/827,083, filed on Apr. 5, 2001, now Pat. No. 6,531,457, which is a continuation of application No. 09/333,387, filed on Jun. 15, 1999, now Pat. No. 6,232,297, application No. 11/002,008, which is a continuation-in-part of application No. 10/263,379, filed on Oct. 1, 2002, now Pat. No. 7,214,665.

(60) Provisional application No. 60/383,200, filed on May 24, 2002, provisional application No. 60/326,517, filed on Oct. 1, 2001, provisional application No. 60/135,573, filed on May 24, 1999, provisional application No. 60/133,374, filed on May 10, 1999, provisional application No. 60/124,316, filed on Mar. 12, 1999, provisional application No. 60/118,029, filed on Feb. 1, 1999.

(51) Int. Cl.
*A61K 31/70* (2006.01)

(52) U.S. Cl. .......................................... 514/46; 514/47

(58) Field of Classification Search ............... 514/46, 514/47, 423
See application file for complete search history.

(56) References Cited

U.S. PATENT DOCUMENTS

| 3,892,777 | A | 7/1975 | Gruenman et al. |
|---|---|---|---|
| 4,012,495 | A | 3/1977 | Schmiechen et al. |
| 4,193,926 | A | 3/1980 | Schmiechen et al. |
| 4,242,345 | A | 12/1980 | Brenner et al. |
| 4,665,074 | A | 5/1987 | Amschler |
| 4,824,660 | A | 4/1989 | Angello et al. |
| 4,879,296 | A | 11/1989 | Daluge et al. |
| 4,938,949 | A | 7/1990 | Borch et al. |
| 4,956,345 | A | 9/1990 | Miyasaka et al. |
| 4,965,271 | A | 10/1990 | Mandell et al. |
| 5,070,877 | A | 12/1991 | Mohiuddin et al. |
| 5,096,906 | A | 3/1992 | Mandell et al. |
| 5,124,455 | A | 6/1992 | Lombardo et al. |
| 5,140,015 | A | 8/1992 | Olsson et al. |
| 5,189,027 | A | 2/1993 | Miyashita et al. |
| 5,272,153 | A | 12/1993 | Mandell et al. |
| 5,278,150 | A | 1/1994 | Olsson et al. |
| 5,298,508 | A | 3/1994 | Jacobson et al. |
| 5,565,462 | A | 10/1996 | Eitan et al. |
| 5,593,975 | A | 1/1997 | Cristalli |
| 5,593,976 | A | 1/1997 | Mongelli et al. |
| 5,665,754 | A | 9/1997 | Feldman et al. |
| 5,668,139 | A | 9/1997 | Belardinelli et al. |
| 5,696,254 | A | 12/1997 | Mansour et al. |
| 5,731,296 | A | 3/1998 | Sollevi |
| 5,756,706 | A | 5/1998 | Mansour et al. |
| 5,854,081 | A * | 12/1998 | Linden et al. ............... 436/501 |
| 5,877,180 | A * | 3/1999 | Linden et al. ............... 514/45 |
| 5,932,558 | A | 8/1999 | Cronstein et al. |
| 5,998,386 | A | 12/1999 | Feldman |
| 6,004,945 | A | 12/1999 | Fukunaga |
| RE36,494 | E | 1/2000 | Olsson et al. |
| 6,020,321 | A | 2/2000 | Cronstein et al. |
| 6,020,339 | A | 2/2000 | Perrier et al. |
| 6,034,089 | A | 3/2000 | Han et al. |
| 6,060,481 | A * | 5/2000 | LaNoue et al. ............ 514/263.34 |
| 6,117,878 | A * | 9/2000 | Linden ............... 514/263.34 |
| 6,232,297 | B1 * | 5/2001 | Linden et al. ............... 514/46 |
| 6,303,619 | B1 * | 10/2001 | Linden ............... 514/263.34 |
| 6,322,771 | B1 * | 11/2001 | Linden et al. ............... 424/9.3 |
| 6,332,771 | B1 | 12/2001 | Adams et al. |
| 6,339,072 | B2 | 1/2002 | Martin et al. |

(Continued)

FOREIGN PATENT DOCUMENTS

EP 0700908 A1 3/1996

(Continued)

OTHER PUBLICATIONS

Okusa et al., "Selective A2A Adenosine Receptor Activation Reduces Ischemia-Reperfusion Injury in Rat Kidney," American J. Physiology: Heart and Circulatory Physiology, 277(3, Pt. 2), F404-F412 (Sep. 1999).*

(Continued)

*Primary Examiner*—L. E. Crane
(74) *Attorney, Agent, or Firm*—Schwegman, Lundberg & Woessner, P.A.

(57) ABSTRACT

The present invention provides a therapeutic method for treating biological diseases that includes the administration of an effective amount of a suitable antibiotic agent, antifungal agent or antiviral agent in conjunction with an $A_{2A}$ adenosine receptor agonist. If no anti-pathogenic agent is known the $A_{2A}$ agonist can be used alone to reduce inflammation, as may occur during infection with antibiotic resistant bacteria, or certain viruses such as those that cause SARS or Ebola. Optionally, the method includes administration of a type IV PDE inhibitor.

33 Claims, 4 Drawing Sheets

U.S. PATENT DOCUMENTS

| | | | |
|---|---|---|---|
| 6,350,735 B1 * | 2/2002 | Monaghan | 514/46 |
| 6,387,889 B1 | 5/2002 | Endo et al. | |
| 6,448,235 B1 * | 9/2002 | Linden et al. | 514/46 |
| 6,514,949 B1 * | 2/2003 | Linden et al. | 514/46 |
| 6,525,032 B2 * | 2/2003 | Mantell et al. | 514/45 |
| 6,531,457 B2 * | 3/2003 | Linden et al. | 514/46 |
| 6,545,002 B1 * | 4/2003 | Linden et al. | 514/263.2 |
| 6,624,158 B2 * | 9/2003 | Mantell et al. | 514/217.06 |
| 6,670,334 B2 * | 12/2003 | Linden et al. | 514/46 |
| 6,936,596 B2 | 8/2005 | Konno et al. | |
| 7,214,665 B2 | 5/2007 | Linden et al. | |
| 7,226,913 B2 | 6/2007 | Linden et al. | |
| 2002/0032168 A1 | 3/2002 | Mantell et al. | |
| 2002/0058641 A1 | 5/2002 | Mantell et al. | |
| 2003/0013675 A1 | 1/2003 | Yeadon et al. | |
| 2003/0162742 A1 | 8/2003 | Linden et al. | |
| 2005/0282831 A1 | 12/2005 | Beauglehole et al. | |

FOREIGN PATENT DOCUMENTS

| | | |
|---|---|---|
| EP | 1150991 B1 | 4/2004 |
| HU | 174074 | 10/1979 |
| WO | WO95/11681 A1 * | 5/1995 |
| WO | WO96/02553 A2 * | 2/1996 |
| WO | WO-9604280 A1 | 2/1996 |
| WO | WO-98/47509 A1 | 10/1998 |
| WO | WO-98/57651 A1 | 12/1998 |
| WO | WO99/34804 A1 * | 7/1999 |
| WO | WO-99/38877 A2 | 8/1999 |
| WO | WO-99/41267 A1 | 8/1999 |
| WO | WO-99/62518 A1 | 12/1999 |
| WO | WO-99/63938 A2 | 12/1999 |
| WO | WO-99/67263 A1 | 12/1999 |
| WO | WO-99/67264 A1 | 12/1999 |
| WO | WO-99/67265 A1 | 12/1999 |
| WO | WO-99/67266 A1 | 12/1999 |
| WO | WO-00/23457 A1 | 4/2000 |
| WO | WO-00/44763 A2 | 8/2000 |
| WO | WO00/78774 A2 * | 12/2000 |
| WO | WO02/09701 A1 * | 2/2002 |
| WO | WO02/096462 A1 * | 12/2002 |
| WO | WO-03/014137 A1 | 2/2003 |

OTHER PUBLICATIONS

Peirce et al., "Selective A2A Adenosine Receptor Activation Reduces Skin Pressure Ulcer Formation and Inflammation," American J. Physiology: Heart and Circulatory Physiology, 281(1, Pt. 2), H67-H72 (Jul. 2001).*

Sullivan et al., "Cyclic AMP-Dependent Inhibition of Human Neutrophil Oxidation Activity by Substituted 2-Propynylcyclohexyl Adenosine A2A Receptor Agonists," British J. Pharmacology, 132(5), 1017-1026 (2001).*

Beers et al. (eds.), The Merck Manual of Diagnosis and Therapy, 17th Edition, Merck & Co., Rahway, NJ, Jan. 1999, only pp. 924-925 supplied.*

Venes et al. (eds.), Taber's Cyclopedic Medical Dictionary, 19th Edition, F. A. Davis, Philadelphia, PA, 2001, only pp. 960-961 supplied.*

Ishiwata et al., "Further Characterization of a CNS Adenosine A2A Receptor Ligand [11C] KF18446 with in vitro Autoradiography and in vivo Tissue Uptake," Annals of Nuclear Medicine, 14(2), 81-89 (2000).*

Sullivan et al., "A2A Adenosine Receptor Activation Improves Survival in Mouse Models of Endotoxemia and Sepsis," Journal of Infectioous Diseases, 189, 1897-1904 (May 15, 2004).*

Moore et al., "A2A Adenosine Receptor Agonists Modify Inflammatory Responses in an E. coli Peritonitis Murine Septic Shock Model," Abstract(###) from the 43rd Annual Meeting of the Infectious Disease Society of America, Oct. 6-9, 2005, San Francisco, California.*

Hogan et al., "Inhibiting the Inflammatory Response in Joint Sepsis," Arthroscopy, 17(3), 311-315 (Mar. 2001).*

Ross et al., "Selective Adenosine A2A Activation Reduces Lung Reperfusion Injury Following Transplantation," Journal of Heart and Lung Transplantation, 18(1), 994-1002 (Oct. 1999).*

Abiru, T., et al., "Nucleosides and nucleotides. 107.2-(cycloalkylalkynyl)adenosines: adenosine $A_2$ receptor agonists with potent antihypertensive effects", Journal of Medicinal Chemistry, 35(12), (Jun. 12, 1992), 2253-2260.

Ali, H., et al., "Methylxanthines Block Antigen-induced Responses in RBL-2H3 Cells Independently of Adenosine Receptors or Cyclic AMP: Evidence for Inhibition of Antigen Binding to IgE", Journal of Pharmacology and Experimental Therapeutics, 258, (1991), 954-962.

Andersson, P., et al., "Anti-anaphylactic and anti-inflammatory effects of xanthines in the lung", Curr. Clin. Pract. Ser., (1985), 187-192.

Baraldi, Pier G., et al., "Synthesis and Biological Activity of a New Series of $N^6$-Arylcarbamoyl, 2-(Ar)alkynyl-$N^6$-arylcarbamoyl, and $N^6$-Carboxamido derivatives of adenosine-5'-N-ethyluronamide as $A_1$ and $A_3$ Adenosine receptor agonists", Journal of Medicinal Chemistry, 41(17), (Aug. 13, 1998), 3174-3185.

Berkich, D. A., et al., "Evidence of Regulated Coupling of $A_1$ Adenosine Receptors by Phosphorylation in Zucker Rats.", American Journal of Physiology, 268 (4), (Apr. 1995), E693-E704.

Bhattacharya, S., et al., "Effects of Long-term Treatment With the Allosteric Enhancer, PD81,723, on Chinese Hamster Ovary Cells Expressing Recombitant Human $A_1$ Adenosine Receptors", Molecular Pharmacology, 50(1), (Jul. 1996), 104-111.

Bhattacharya, S., et al., "The Allosteric Enhancer, PD 81,723, Stabilizes Human $A_1$ Adenosine Receptor Coupling to G Proteins", Biochimica et Biophysica Acta, 1265 (1), (Feb. 1995),15-21.

Bridges, A.J., et al., "$N^6$-[2-(3,5-Dimethoxyphenyl)-2-(2-Methylphenyl)-Ethyl]Adenosine and Its Uronamide Derivatives. Novel Adenosine Agonists With Both High Affinity and High Selectivity for the Adenosine $A_2$ Receptor", Journal of Medicinal Chemistry, 31(7), (Jul. 1988), 1282-1285.

Bruns, R. F., "Adenosine Receptors—Roles and Pharmacology", Biological Actions of Extracellular ATP, 603, Annals of The New York Academy of Sciences, (1990), 211-226.

Bruns, R. F., et al., "Characterization of the $A_2$ Adenosine Receptor Labeled by [$^3$H]NECA in Rat Striatal Membranes", Molecular Pharmacology, 29, (1986), pp. 331-346.

Buster, B., et al., "The Effect of Adenosine Receptor Agonists on Neutrophil Pleocytosis and Blood-Brain Barrier Pathophysiology in Experimental Bacterial Meningitis", Abstract of the Interscience Conference on Antimicrobial Agents and Chemotherapy, 37, Abstract No. B-72, (1997), p. 39.

Camaioni, E., et al., "Adenosine receptor agonists: synthesis and bilogical evaluation of the diastereoisomers of 2-(3-Hydroxy-3-phenyl-1-propyn-1-yl)NECA", Bioorganic & Medicinal Chemistry, 5(12), (Dec. 1997), 2267-75.

Carruthers, A. M., et al., "Hypotensive Responses to the Putative Adenosine $A_3$ Receptor Agonist $N^5$-20(4-Aminophenyl)-Ethyladenosine in the Rat", Drug Development Research, 30, (1993),pp. 147-152.

Cassada, D C., et al., "Adenosine $A_{2A}$ agonist reduces paralysis after spinal cord ischemia: correlation with $A_{2A}$ receptor expression on motor neurons", Annals of Thoracic Surgery, 74(3), (Sep. 2002),846-9; discussion 849-50.

Cassada, D C., et al., "Adenosine $A_{2A}$ analogue ATL-146e reduces systemic tumor necrosing factor and spinal cord capillary platelet-endothelial cell adhesion molecule-1 expression after spinal cord ischemia", Journal of Vascular Surgery, 35(5), (May 2002), 994-98.

Cassada, D C., et al., "Adenosine $A_{2A}$ analogue improves neurologic outcome after spinal cord trauma in the rabbit.", Journal of Trauma-Injury Infection & Critical Care, 53(2), (Aug. 2002),225-9.

Cassada, D C., et al., "Adenosine analogue reduces spinal cord reprefusion injury in a time-dependent fashion", Surgery, 130(2), (Aug. 2001), 230-35.

Cassada, D C., et al., "An adenosine $A_{2A}$ agonist, ATL-146e, reduces paralysis and apoptosis during rabbit spinal cord reperfusion.", Journal of Vascular Surgery, 34(3), (Sep. 2001), 482-88.

Cassada, D C., et al., "Systemic adenosine A₂ agonist ameliorates ischemic reperfusion injury in the rabbit spinal cord", *Annals of Thoracic Surgery*, 72(4), (Oct. 2001), 1245-50.

Cembrzynska-Nowak M., et al., "Elevated Release of Tumor Necrosis Factor-alpha and Interferon-gamma by Bronchoalveolar Leukocytes From Patients With Bronchial Asthma.", *American Review of Respiratory Disease*, 147(2), (1993), 291-295.

Cothran, D. L., et al., "Ontogeny of Rat Myocardial A₁ Adenosine Receptors", *Biol Neonate*, 68 (2), (1995), 111-118.

Cristalli, G., "2-Alkynyl Derivatives of Adenosine an Adenosine-5'-N-ethyluronamide as Selective Agonists at A₂ Adenosine Receptors", *Journal of Medicinal Chemistry*, 35 (13), (1992), 2363-2368.

Cronstein, B. N., "Adenosine Modulates the Generation of Superoxide Anion by Stimulated Human Neutrophils Via Interaction With a Specific Cell Surface Receptor", *Annals New York Academy of Science*, 451, (1985), 291-314.

Cronstein, B. N., "Adenosine; A Physiologic Modulator Of Superoxide Anion Generated By Human Neutrophils. Adenosine Acts Via An A₂ Receptor On Human Neutrophils", *Journal Of Immunology*, 135 (2), (1985), 1366-1371.

Cronstein, B. N., "Engagement of Adenosine Receptors Inhibits Hydrogen Peroxide (H₂O₂) Release by Activated Human Neutrophils", *Clinical Immunology and Immunopathology*, 42(1), (1987), 76-85.

Cronstein, B. N., "Methotrexate Inhibits Leukocyte Influx Into Inflammatory Sites Via The Adenosine (A₂) Receptor", *Clinical Research*, 41 (2), (1993),p. 244A.

Cronstein, N., et al., "Occupancy Of Adenosine Receptors Raises Cyclic AMP Alone And In Synergy With Occupancy Of Chemoattractant Receptors And Inhibits Membrane Depolarization", *Biochemical Journal*, 252 (3), (1988),pp. 709-715.

Cronstein, B. N., "The Adenosine/Neutrophil Paradox Resolved: Human Neutrophils Possess Both A₁ and A₂ Receptors That Promote Chemotaxis and Inhibits O₂ Generation, Respectively", *Journal of Clinical Investigation*, 85 (4), (1990), 1150-1157.

Day, Y.-J., et al., "Protection From Ischemic Liver Injury by Activation of $A_{2A}$ Adenosine Receptors During Reperfusion: Inhibition of Chemokine Induction", *American Journal of Physiology Gastrointestinal and Liver Physiology*, 286, (2004), G285-293.

Day, Y. J., et al., "Renal Protection from Ischemia Mediated by $A_{2A}$ Adenosine Receptors on Bone Marrow-Derived Cells.", *Journal of Clinical Investigation*, 112(6), (2003), 883-891.

De La Harpe, J., "Adenosine Regulates the Respiratory Burst Of Cytokine—Triggered Human Neutrophils Adherent To Biological Surfaces", *Journal Of Immunology*, 143(2),596-602.

De Moraes, V. L., et al., "Effect of Cyclo-Oxygenase Inhibitors and Modulators of Cyclic AMP Formation on Lipopolysaccharide-Induced Neutrophil Infiltration in Mouse Lung", *British Journal of Pharmacology*, 117, (1996),pp. 1792-1796.

De Zwart, M., et al., "5-N-Substituted Carboxamidoadenosines as Agonists for Adenosine Receptors", *Journal of Medicinal Chemistry*, 42(8), (Apr. 22, 1999),1384-1392.

Dinarello, C. A., "interleukin-1 And Tumor Necrosis Factor: Effector Cytokines In Autoimmune Diseases", *Seminars in Immunology*, 4, (1992), 133-145.

Doyle, M. P., et al., "Nucleoside-induced Arteriolar Constriction: a Mast Cell-dependent Response.", *American Journal of Physiology*, (May 1994),pp. H2042-H2050.

Elzein, E., et al., "Design, Synthesis And Biological Evaluation Of 2-(4-Substituted-N-Pyrazolyl)-Adenosine Derivatives As Novel Short Acting Adenosine $A_{2A}$ Receptor Agonists", *Drug Development Research*, 50 (1), Abstracts From Purines 2000: Biochemical, Pharmacological, and Clinical Perspectives: Abstract No. 061,(May, 2000),p. 64.

Fang, G. D., et al., "A New Selective Adenosine A2a Receptor Agonist, Improves Survival in *E. coli* O26:B6 Lipopolysaccharide (LPS)-Induced Experimental Murine Endotoxemia", *Journal of Investigative Medicine*, Abstract No. 797,(2000), p. 148A.

Feoktistov, I., et al., "Adenosine $A_{2B}$ receptors", *The American Society for Pharmacological and Experimental Therapeutics*, 49(4), (1997), 381-402.

Feoktistov, I., et al., "Role of Adenosine in Asthma", *Drug Development Research*, 39, (1996),pp. 333-336.

Ferrante, A., "Optimal Conditions for Simultaneous Purification of Mononuclear and Polymorphonuclear Leucocytes From Human Blood by the Hypaque-Ficoll Method", *Journal of Immunological Methods*, 36(2), (1980),109-117.

Figler, R. A., et al., "Reconstitution of Bovine A₁ Adenosine Receptors and G Proteins in Phospholipid Vesicles: βγ.-Subunit Composition Influences Guanine Nucleotide Exchange and Agonist Binding", *Biochemistry*, 36(51), (1997),16288-16299.

Figler, R. A., et al., "Reconstitution of Recombinant Bovine A₁ Adenosine Receptors in Sf9 Cell Membranes with Recombitant G Proteins of Defined Composition.", *Molecular Pharmcology*, 50 (6), (Dec. 1996),pp. 1587-1595.

Firestein, G. S., "Adenosine Regulating Agents: A Novel Approach to Inflammation and Inflammatory Arthritis", *Clinical Research*, 41(2), (1993),170A.

Fiser, S M., et al., "Adenosine $A_{2A}$ receptor activation decreases reperfusion injury associated with high-flow reperfusion.", *Journal of Thoracic & Cardiovascular Surgery*, 124(5), (Nov. 2002),973-8.

Fozard, J. R., "Adenosine A₃ Receptors Mediate Hypotension in the Angiotensin II-supported Circulation of the Pithed Rat", *British Journal of Pharmacology*, 109(1), (1993), 3-5.

Francis, J. E., "Highly Selective Adenosine A₂ Receptor Agonists in a Series of N-Alkylated 2-Aminoadenosines", *Journal of Medicinal Chemistry*, 34 (8), (1991),pp. 2570-2579.

Frangogiannis, N G., et al., "Myocardinal Ischemia: Mechanisms, Reperfusion, Protection", *Birkhuser Verlag*, M. Karmazyn, ed.,(1996), 236-284.

Gao, Z., et al., "$A_{2B}$ Adenosine and $P2Y_2$ Receptors Stimulate Mitogen-activated Protein Kinase in Human Embryonic Kidney-293 Cells. Cross-talk Between Cyclic AMP and Protein Kinase c Pathways", *Journal of Biological Chemistry*, 274(9), (Feb. 26, 1999), 5972-5980.

Gao, Z., et al., "Purification of A₁ Adenosine Receptor-G-protein Complexes: Effects of Receptor Down-regulation and Phosphorylation on Coupling", *Biochemical Journal*, 338 (Pt3), (Mar. 1999), 729-736.

Gilchrist, A., et al., "Antagonists of the Receptor-G Protein Interface Block Gi-coupled Signal Transduction", *Journal of Biological Chemistry*, 273 (24), (Jun. 12, 1998),14912-14919.

Girardi, N., et al., "Inflammatory Aneurysm of the Ascending Aorta and Aortic Arch", *Ann. Thor. Surg.*, 64, (1997), 251-253.

Glover, D. K., et al., "Bolus Injection of DWH-146E, A Novel Adenosine A2A Receptor Agonist for Use in Vasodilator Stress Imaging", *Journal of Nuclear Cardiology*, 7 (4), Abstract No. 44.20,(Sep. 23, 2000),1 p.

Glover, D. K., et al., "Characterization of a New, Highly Selective Adenosine $A_{2A}$ Receptor Agonist with Potential Use in Pharmacologic Stress Perfusion Imaging", *Circulation*, 100, Abstract,(1999), 1 pg.

Glover, D K., et al., "Pharmacological stress myocardial perfusion imaging with the potent and selective $A_{2A}$ adenosine receptor agonists ATL193 and ATL146e administered by either intravenous infusion or bolus injection", *Circulation*, 104(10), (Sep. 4, 2001), 1181-1187.

Glover, D. K., et al., "Pharmacological stress thallium scintigraphy with 2-cyclohexylmethylidenehydrazinoadenosine (WRC-0470). A novel, short-acting adenosine $A_{2A}$ receptor agonist", *Circulation*, 94(7), (Oct. 1, 1996),1726-1732.

Glover, D. K., et al., "Vasodilator Stress Imaging Using New Adenosine $A_{2A}$ Receptor Agonists Administered by Bolus Injection", *J. Am. Coll. Cardiol.*, 35, Abstract,(2000).

Griswold, D. E., et al., "Effects of Selective Phosphodieasterase Type IV Inhibitor, Rolipram, on Fluid and Cellular Phases of Inflammatory Response", *Chemical Abstracts*, 119, Abstract No. 173828e,(1993), p. 49.

Hanlon, W. A., "rTNFα Facilitates Human Polymorphonuclear Leukocyte Adherence to Fibrinogen Matrices With Mobilization of Specific and Tertiary But Not Azurophilic Granule Markers", *Journal of Leukocyte Biology*, 50 (1), (1991), 43-48.

Hartung, H. P., "Immune-Mediated Demyelination", *Annals of Neurology*, 33 (6), (Jun. 1993), 563-567.

Heller, L. J., et al., "Effect of Adenosine on Histamine Release and Atrioventricular Conduction During Guinea Pig Cardia Anaphylaxis", *Circulation Research*, 62(6), (Jun. 1988), 1147-1158.

Holmes, "Restenosis After Percutaneous Transluminal Coronary Angioplasty (PTCA): A Report From the PTCA Registry of the National Heart, Lung, and Blood Institute", *American Journal of Cardiology*, 53, (1984), 77C-81C.

Homma, H., et al., "Nucleosides and nucleotides. 112.2-(1-Hexyn-1-yl)adenosine-5'-uronamides: a new entry of selective $A_2$ adenosine receptor agonists with potent antihypertensive activity.", *Journal of Medicinal Chemistry*, 35(15), (Jul. 1992), 2881-2890.

Hussain, T., et al., "$^{125}$I-APE Binding to Adenosine Receptors in Coronary Artery: Photoaffinity Labeling With $^{125}$I-azidoAPE$^{1}$", *The Journal of Pharmacology and Experimental Therapeutics*, 276 (1), (Jan. 1996),pp. 284-288.

Hutchison, A. J., "2-(Arylalkylamino)Adenosine-5'-Uronamides: A New Class of Highly Selective Adenosine $A_2$ Receptor Ligands", *Journal of Medicinal Chemistry*, 33 (7), (1990),pp. 1919-1924.

Hutchison, A. J., "CGS 21680C, an $A_2$ Selective Adenosine Receptor Agonist With Preferential Hypotensive Activity", *The Journal of Pharmacology and Experimental Therapeutics*, 251(1), (1989),pp. 47-55.

Iannone, M. A., "Effects of Adenosine on Human Neutrophil Function and Cyclic AMP Content", *In: Topics and Perspectives in Adenosine Research*, Eds. E. Gerlach et al., Springer-Verlag, Berlin, Germany,(1986), 286-298.

Imagawa, D. K., et al., "The Role of Tumor Necrosis Factor in Allograft Rejection", *Transplantation*, 51, (Jan. 1991), 57-62.

Ito, B. R., et al., "Role of Cardiac Mast Cells In Complement C5a-induced Myocardial Ischemia", *American Journal of Physiology-Heart and Circulatory Physiology*, 264(5), (May 1993), H1346-H1354.

Jarvis, M. F., "[3H]CGS 21680, A Selective $A_2$ Adenosine Receptor Agonist Directly Labels $A_2$ Receptors in Rat Brain.", *Journal of Pharmacology and Experimental Therapeutics*, 251(3), (Dec. 1989), 888-893.

Jolly, S. R., "Effects of Lodoxarnide on Ischemic Reperfused Myocardium", *Journal of Cardiovascular Pharmacology*, 4(3), (1982),441-448.

Kaminuma O., et al., "Effect of T-440, a Novel Type IV Phosphodiesterase Inhibitor, on Allergen-Induced Immediate and Late Asthmatic Reaction and Leukocyte Infiltration into the Airways of Guinea Pigs", *International Archives of Allergy & Immunology*, 112(4), (1997),406-411.

Keller, A. M., "Acute Reoxygeneration Injury in the Isolated Rat Heart: Role of Resident Cardiac Mast Cells", *Circulation Research*, 63(6), (Dec. 1988), 1044-1052.

Kennedy, A. P., et al., "Covalent Modification of Transmembrane Span III of the $A_1$ Adenosine Receptor With an antagonist Photoaffinity Probe.", *Molecular Pharmacology*, 50, (Oct. 1996), 789-798.

Klotz, K.-N., et al., "2-Substituted N-ethylcarboxamidoadenosine derivatives as high-affinity agonists at human $A_3$ adenosine receptors", *Naunyn-Schmiedebergs Archives of Pharmacology*, 360(2), (Aug. 1999), 103-108.

Kollias-Baker, C., et al., "Allosteric Enhancer PD 81,723 Acts by Novel Mechanism to Potentiate Cardiac Actions of Adenosine", *Circulation Research*, 75(6), (Dec. 1994), 961-971.

Koshiba, M., "Patterns of $A_{2A}$ Extracellular Adenosine Receptor Expression in Different Functional Subsets of Human Peripheral T Cells", *The FASEB Journal*, Abstract No. 703.38, (1999), p. A944.

Koshiba, M., et al., "Patterns of $A_{2A}$ Extracellular Adenosine Receptor Expression in Different Functional Subsets of Human Peripheral T Cells. Flow Cytometry Studies With Anti-$A_{2A}$ Receptors Monoclonal Antibodies.", *Molecular Pharmacology*, 55(3), (Mar. 1999), 614-624.

Leclerc, G., "Percutaneous Arterial Gene Transfer in a Rabbit Model", *Journal of Clinical Investigation*, 90 (3), (1992), 936-944.

Legrand-Poels, S., "Activation of Human Immunodeficiency Virus Type 1 by Oxidative Stress", *AIDS Research and Human Retroviruses*, 6(12), (1990),1389-1397.

Lette, J., et al., "Safety of Dipyridamole Testing in 73,806 Patients: The Multicenter Dipyridamole Safety Study", *Journal of Nuclear Cardiology*, 2(1), (1995), 3-17.

Linden, J., "($^{125}$I)Aminobenzyladenosine, A New Radioligand with Improved Specific Binding to Adenosine Receptors in Heart", *Circulation Research*, 56(2), (Feb. 1985), 279-284.

Linden, J., et al., "Adenosine Receptors", *In: Handbook of Receptos and Channels—G Protein Coupled Receptors, Chapter 2*, Edited by S.J. Peroutka, Published by CRC Press, Boca Raton, FL,(1994), 29-44.

Linden, J., "Allosteric Enhancement of Adenosine Receptors", *In: Purinergic Approaches in Experimental Therapeutics, Chapter 5*, Edited by K.A. Jacobson et al., and Published by Wiley-Liss, Inc. ,(1997), 85-97.

Linden, J., "Calculating the Dissociation Constant of an Unlabeled Compound from the Concentration Required to Displace Radiolabel Binding by 50%", *Journal of Cyclic Nucletide Research*, 8 (3), (1982), 163-172.

Linden, J., "Cloned Adenosine $A_3$ Receptors: Pharmacological Properties, Species Differences and Receptor Functions.", *Trends in Pharmacological Sciences*, 15(8), (Aug. 1994), 298-306.

Linden, J., "Molecular Cloning and Functional Expression of a Sheep $A_3$ Adenosine Receptor with Widespread Tissue Distribution", *Molecular Pharmacology*, 44 (3), (Sep. 1993), 524-532.

Linden, J., "Recombinant Techniques as Applied to the Study of $A_1$ Adenosine Receptors", *In: Adenosine and Adenine Nucleotides: From Molecular Biology to Integrative Physiology, Chapter 2*, Kluwer Academic Publishers, Boston, Edited by L. Belardinelli,(1995), 15-19.

Linden, J, et al., "The Structure and Function of $A_1$ and $A_{2B}$ Adenosine Receptors", *Life Science*, 62 (17/18), (1998),1519-1524.

Luthin, D. R., et al., "Adenosine Receptors", *Biomembranes*, 2B, (1996), 321-347.

Luthin, D. R., "Characterization of Two Affinity States of Adenosine $A_{2a}$ Receptors With a New Radioligand, 2-[2-(4-amino-3-[$^{125}$I]iodophenyl) Ethylamino]Adenosine.", *Molecular Pharmacology*, 47 (2), (Feb. 1995), 307-313.

Luthin, D. R., et al., "Comparison of $A_4$ and $A_{2a}$ Binding Sites in Striatum and COS Cells Transfected With Adesosine $A_{2a}$ Receptors.", *The Journal of Pharmacology and Experimental Therapeutics*, 272, (Feb. 1995), 511-518.

Luthin, D. R., et al., "Photoaffinity Labeling With 2(-)[2-(4-azido-3(-)[$^{125}$I]-iodophenyl)ethylamino]Adenosine and Autoradiography With 2(-)[2-(4-amino-3-[$^{125}$I]iodophenyl)ethylamino]Adenosine of $A_{2a}$ Adenosine Receptor in Rat Brain.", *Journal of Neurochemistry*, 65 (5), (Nov. 1995), 2072-2079.

Mager, P. P., "Neural network approaches applied to selective $A_{2a}$ adenosine receptor agonists", *Med. Chem. Res.*, 8(6), (1998), 277-290.

Mahan, L. C., et al., "Cloning and Expression of an $A_1$ Adenosine Receptor from Rat Brain", *Molecular Pharmacology*, 40 (1), (Jul. 1991), 1-7.

Mannel, D. N., "Tumor Necrosis Factor: A Cytokine Involved in Toxic Effects of Endotoxin", *Reviews of Infectious Diseases*, 9, (1987),S602-S606.

March, J., *Advanced Organic Chemistry: Reactions, Mechanisms, and Structure*, Fourth Edition, John Wiley & Sons,(1992), p. 400.

Martin, P. L., et al., "Characterization of 8-(N-methylisopropyl)amino-N6-(5' -andohydroxy-endonorbornyl)-9-methyladenine (WRC-0571), a Highly Potent and Selective, Nonxanthine Antagonist of $A_1$ Adenosine Receptors.", *The Journal of Pharmacology and Experimental Therapeutics*, 276(2), (Feb. 1996), 490-499.

Martin, P. L., et al., "Pharmacology of 2-cyclohexylmethylidenehydrazino-adenosine (WRC-0470), a Novel, Short-acting Adenosine $A_{2A}$ Receptor Agonist That Produces Selective Coronary Vasodilation", *Drug Development Research*, 40 (4), (1997), 313-324.

Matherne, G. P., et al., "Transgenic $A_1$ Adenosine Receptor Overexpression Increases Myocardial Resistence to Ischemia", *Proceedings of the National Academy of Science*, 94, (Jun. 1997), 6541-6546.

Matsuyama, T., "Cytokines and HIV Infection: is AIDS a Tumor Necrosis Factor Disease?", *AIDS*, 5(12), (1991), 1405-1417.

McGarrity, S. T., "Inhibition of Neutrophil Superoxide Anion Generation by Platelet Products: Role of Adenine Nucleotides", *Journal of Leukocyte Biology*, 44(5), (1988),411-421.

McGarrity, S. T., "Regulation of Human Neutrophil Function by Adenine Nucleotides", *Journal of Immunology*, 142(6), (1989), 1986-1994.

McLaughlin, D. P., et al., "Hemodynamic and Metabolic Correlates of Dipyridamole-induced Myocardial Thallium-201 Perfusion Abnormalities in Multivessel Coronary Artery Disease.", *American Journal of Cardiology*, 73 (16), (Jun. 1994), 1159-1164.

McPherson, J A., "Adenosine $A_{2A}$ receptor stimulation reduces inflammation and neointimal growth in a murine carotid ligation model", *Arteriosclerosis, Thrombosis & Vascular Biology*, 21(5), (May 2001), 791-796.

McPherson, J. A., et al., "Effect of Prolonged Adenosine $A_{2A}$ Receptor Activation on Neointimal Formation in the Injured Mouse Carotid Artery", *The FASEB Journal*, Abstract No. 299.2, (1999), p. A367.

McPherson, J. A., et al., "Prolonged Adenosine $A_{2a}$ Receptor Stimulation Reduces Inflammation and Neointima Formation in a Murine Carotoid Ligation Model", *Supplement to Circulation*, 100 (18), Abstract No. 3652, (Nov. 2, 1999), 1 pg.

Merritt, H. R., et al., "Abnormal Q Waves are Common Early in AMI and Do Not Predict Decreased Myocardial Salvage With Thrombolytic Therapy", *Special Issue Journal of American College of Cardiology*, Abstract No. 895-77,(Feb. 1994), p. 195A.

Miyamoto, F., et al., "Retinal Cytokine Response in Mouse Alkali-Burned Eye", *Opthalmic Res.*, 30, (1997), 168-171.

Mizumura, T., et al., "PD 81,723, an Allosteric Enhancer of the $A_1$ Adenosine Receptor, Lowers the Threshold for Ischemic Preconditioning in Dogs.", *Circulation Research*, 79 (3), (Sep. 1996),pp. 415-423.

Molnar-Kimber, K. L., et al., "Modulation of TNFα and IL-1β From Endotoxin-Stimulated Monocytes by Selective PDE Isozyme Inhibitors", *Agents & Actions*, 39, (1993), C77-C79.

Mumby, S. M., et al., "G-protein α-subunit expression, myristoylation and membrane association in COS cells", *Proceedings of the National Academy of Sciences*, 87 (2), (Jan. 1990), 728-732.

Nabel, E. G., "Site-Specific Gene Expression in Vivo by Direct Gene Transfer into the Arterial Wall", *Science*, 249, (1990), 1285-1288.

Newman, K. D., "Adenovirus-mediated Gene Transfer into Normal Rabbit Arteries Results in Prolonged Vascular Cell Activation, Inflammation and Neointimal Hyperplasia", *Journal of Clinical Investigation*, 96 (6), (1995), 2955-2965.

Nielson, C. P., "Effects of Adenosine on Polymorphonuclaer Leucocyte Function, Cyclic 3': 5'- adenosine Monophosphate, and Intracellular Calcium", *British Journal of Pharmacology*, 97(3), (1989), 882-888.

Niiya, K., "2-(N'-Alkylidenehydrazino)Adenosines: Potent and Selective Coronary Vasodilators", *Journal of Medicinal Chemistry*, 35 (24), (1992),4557-4561.

Nolte, D., "Reduction of Postischemic Leukocyte-Endothelium Interaction by Adenosine Via $A_2$ Receptor", *Biological Abstract*, 94 (11), Abstract No. 116779,(1992),1 pg.

O'Regan, M. H., et al., "Adenosine Receptor Agonists Inhibit the Release of γ-Aminobutyric Acid (GABA) From the Ischemic Rat Cerebral Cortex", *Chemical Abstracts*, 117, Abstract No. 104867p,(1992),p. 170.

Okusa, M D., "$A_{2A}$ Adenosine Receptor-Mediated Inhibition of Renal Injury and Neutrophil Adhesion", *American Journal of Physiology—Renal Fluid & Electrolyte Physiology*, 279(5), (2000), F809-F818.

Okusa, M D., "Enhanced Protection from Renal Ischemia: Reperfusion Injury With $A_{2A}$-Adenosine Receptor Activation and PDE 4 Inhibition", *Kidney International*, 59(6), (2001), 2114-2125.

Olsson, R. A., "$N^5$ Substituted $N$-Alkyladenosine-5'-Uronamides: Bifunctional Ligands Having Recognition Groups for A1 and A2 Adenosine Receptors", *Journal of Medicinal Chemistry*, 29 (9), (1986), 1683-1689.

Peart, J., et al., "Adenosine-Mediated Cardioprotection in Ischemic-Reperfused Mouse Heart.", *Journal of Cardiovascular Pharmacology*, 39(1), (Jan. 2002), 117-129.

Peet, N. P., "Conformationally Restrained, Chiral (Phenylisopropyl)Amino-Substituted Pyrazolo[3,4-d]Pyrimidines and Purines With Selectivity for Adenosine $A_1$ and $A_2$ Receptors", *Journal of Medicinal Chemistry*, 35 (17), (1992), 3263-3269.

Pennell, R L., et al., "Inflammatory abdominal aortic aneurysms: A thirty-year review", *J. Vasc. Surg.*, 2, (1985),859.

Pfister, J. R., et al., "Synthesis and Biological Evaluation of the Enantiomers of the Potent and Selective $A_1$-adenosine Antagonist 1,3-dipropyl-8-[2-(5,6-epoxynorbornyl)]-xanthine", *Journal of Medicinal Chemistry*, 40 (12), (Jun. 1997),pp. 1773-1778.

Pulle, V., et al., "Design, Synthesis And Pharmacological Evaluation of 2(1-Alkyl-Pyrazol-4-YL) Adenosine Derivatives As Short Acting Adenosine A2A Receptor Agonists", *Drug Development Research*, 50 (1), Abstracts From Purines 2000: Biochemical, Pharmacological and Clinical Perspectives: Abstract No. 062,(May 2000), p. 64.

Ranhosky, A., et al., "The Safety of Intravenous Dipyridamole Thallium Myocardial Perfusion Imaging", *Circulation*, 81(4), (Apr. 1990),pp. 1205-1209.

Riou, L M., "Influence of propranolol, enalaprilat, verapamil, and caffeine on adenosine $A_{2A}$-receptor-mediated coronary vasodilation", *Journal of the American College of Cardiology*, 40(9), (Nov. 6, 2002),1687-94.

Roberts, P. A., "Inhibition by Adenosine of Reactive Oxygen Metabolite Production by Human Polymorphonuclear Leucocytes", *Biochemical Journal*, 227(2), (1985), 669-674.

Robeva, A. S., "Double Tagging Recombitant $A_1$- and $A_{2A}$-Adenosine Receptors With Hexahistidine and the FLAG Epitope. —Development of an Efficient Generic Protein Purification Procedure.", *Biochemical Pharmacology*, 51(4), (Feb. 1996),pp. 545-555.

Robeva, A. S., et al., "Molecular Characterization of Recombinant Human Adenosine Receptors", *Drug Development Research*, 39, (1996), 243-252.

Rosin, D. L., et al., "Immunohistochemical Localization of Adenosine $A_{2A}$ Receptors in the Rat Central Nervous System", *The Journal of Comparative Neurology*, 401, (1998), 163-186.

Ross, S. D., et al., "Selective Adenosine-$A_{2A}$ Activation Reduces Lung Reperfusion Injury Following Transplantation", *Journal of Heart and lung transplantation*, 18 (1), Abstract Only, Proceedings of the Nineteenth Annual Meeting and Scientific Sessions of the International Society for Heart and Lung Transplantation, San Francisco, CA,(Jan. 1999), p. 72.

Ross, R., "The Pathogenesis of Antherosclerosis: A Perspective for the 1990s", *Nature*, 362, (Apr. 29, 1993),801-809.

Rothe, G. A., "Flow Cytometric Measurement of the Respiratory Burst Activity of Phagocytes Using Dihydrorhodamine 123", *Journal of Immunological Methods*, 138(1), (1991),133-135.

Sawmiller, D. R., et al., "Effects of Xanthine Amine Congener on Hypoxic Resistence and Venous and Epicardial Adenosine Concentrations.", *Cardiovascular Research*, 28(5), (May 1994), 604-609.

Schiffmann, S. N., et al., "Distribution of adenosine $A_2$ receptor mRNA in the human brain", *Neuroscience Letters*, 130, (1991), 177-181.

Schlack, et al., "Adenosine $A_2$-Receptor Activation at Reperfusion reduces Infarct Size and Improves Myocardial Wall Function in Dog Heart", *Biological Abstract*, 96 (6), Abstract No. 67801,(1993), 1 pg.

Schrier, D. J., "The Effects of Adenosine Agonists on Human Neutrophil Function", *Journal of Immunology*, 137 (10), (1986),pp. 3284-3289.

Seekamp, A., "Ischemia—Reperfusion Injury", *Agents and Actions Supplements*, 41, (1993), 137-152.

Sharief, M. K., et al., "Elevated Serum Levels of Tumor Necrosis Factor-α in Guillain-Barrlé Syndrome", *Annals of Neurology*, 33, (Jun. 1993), 591-596.

Sharma, H S., et al., "Role of cytokines in myocardial ischemia and reperfusion", *Med. of Inflamm.*, 6, (1987), 175-183.

Shepherd, R. K., et al., "Adenosine-induced Vasoconstriction in-Vivo. Role of the Mast Cell and $A_3$ Adenosine Receptor.", *Circulation Research*, 78 (4), (Apr. 1996), 627-634.

Sipka, S., "Adenosine Induced Delay of Expression of AIDS Virus, HIV, in H9T Cells", *Acta. Biochimica et Biophysica Hungarica*, 23(1), (1988) 75-82.

Siragy, H. M., et al., "Sodium Intake Markedly Alters Renal Interstitial Fluid Adenosine", *Hypertension*, 27 (3 Pt 1), (Mar. 1996), 404-407.

Smits, P., et al., "Cardiovascular effects of two xanthines and the relation to adenosine antagonism", *Clinical Pharmacology and Therapeutics*, 45(6), (1989), 593-599.

Sullivan, G. W., "Adenosine (ADO) Modulates Endotoxin and TNF-Induced PMN Activation", *Clinical Research*, 41(2), (1993), p. 172A.

Sullivan, G. W., et al., "Neutrophil $A_{2A}$ Adenosine Receptor Inhibits Inflammation in a Rat Model of Meningitis: Synergy with the Type IV Phosphodiesterase Inhibitor, Rolipram", *The Journal of Infectious Diseases*, 180, No. 5, (1999), 1550-1560.

Sullivan, G. W., "Role of $A_{2A}$ Adenosine Receptors in Inflammation", *Drug Development Research*, 45 (3/4), (1998), 103-112.

Sullivan, G. W., "The Specific Type IV Phosphodiesterase Inhibitor Rolipram Combined with Adenosine Reduces Tumor Necrosis Factor-a-Primed Neutrophil Oxidative Activity", *International Journal of Immunonopharmacology*, 17(10), (1995), 793-803.

Sullivan, G. W., "Two Methylxanthines, Pentoxifylline (PTX) and Caffeine (CAF) Have Divergent Effects on Tumor Necrosis Factor (TNF)-Primed Human Neutrophil (PMN) Activation", *Clinical Research*, 41(2), (1993),p. 172A.

Takiguchi, Y., et al., "Early administration of YT-146, an adenosine $A_2$ receptor agonist, inhibits neointimal thickening after rat femoral artery endothelium injury", *European Journal of Pharmacology* 281 (1995) 205-207, (Mar. 16, 2002),205-207.

Topol, E. J., "Randomised Trial of Coronary Intervention With Antibody Against Platelet IIb/IIIa integrin for Reduction of Clinical Restenosis: Results at Six Months", *The Lencet*, 343(8902), (1994), 881-886.

Tracey, K. J., "Cachectin/Tumor Necrosis Factor Induces Cachexia, Anemia, and Inflammation", *Journal of Experimental Medicine*, 167, (Mar. 1988),1211-1227.

Tucker, A. L., "$A_1$ adenosine receptors. Two amino acids are responsible for species differences in ligand recognition", *Journal of Biological Chemistry*, 269(45), (Nov. 11, 1994), 27900-27906.

Ueeda, M., "2-Alkoxyadenosines: Potent and Selective Agonists at the Coronary Artery $A_2$ Adenosine Receptor", *Journal of Medicinal Chemistry*, 34(4), (1991), 1334-1339.

Ukena, D., et al., "Species Differences in Structure-Activity Relationships of Adenosine Agonists and Xanthine Antagonists at Brain A1 Adenosine Receptors", *FEBS Letters*, 209 (1), (Dec. 1986), 122-128.

Underwood, D. C., et al., "Inhibition of Antigen-Induced Bronchoconstriction and Eosinophil Infiltration in the Guinea by the Cyclic AMP-Specific Phosphodiesterase Inhibitor, Rolipram", *Chemical Abstracts*, 119 (16), Abstract No. 173975a,(1993), p. 67.

Van Calker, D., et al., "Adenosine Regulates via Two Different Types of Receptors, the Accumulation of Cyclic Amp in Cultured Brain Cells", *Journal of Neurochemistry*, 33, (1979), 999-1005.

Van Calker, D., "Carbamazepine Distinguishes Between Adenosine Receptors That Mediate Different Second Messenger Responses", *European Journal of Pharmacology*, 206 (4), (1991), 285-290.

Vittori, S., et al., "2-alkenyl and 2-alkyl derivatives of adenosine and adenosine-5'-N-ethyluronamide: different affinity and selectivity of E- and Z-diastereomers at $A_{2A}$ adenosine receptors.", *Journal of Medicinal Chemistry*, 39(21), (Oct. 1996), 4211-4117.

Walker, B. A., et al., "Adenosine $A_{2a}$ Receptor Activation Delays Apoptosis in Human Neutrophils", *The American Association of Immunologists*, (1997), 2926-2931.

Walker, D I., et al., "Inflammatory Aneurysms of the Abdominal Aorta", *Brit. J. Surg.*, 59, (1972), 609-614.

Wan, A. A., et al., "Binding of the Adenosine $A_2$ Receptor Ligand ($^3$H)CGS 21680 to Human and Rat Brain: Evidence for Multiple Affinity Sites", *Journal of Neurochemistry*, (1990), 1763-1771.

Wolff, A. A., et al., "Ventricular Arrhythmias Parallel Cardiac Histamine Efflux After Coronary Artery Occlusion in the Dog", *Agents and Actions*, 25 (3/4), (1988), 296-306.

Yoneyama, F., "Vasodepressor Mechanisms of 2-(1-octynyl)-Adenosine (YT-146), a Selective Adenosine $A_2$ Receptor Agonist, Involve the Opening of Glibenclamide-sensitive $K^+$ Channels", *European Journal of Pharmacology*, 213 (1), (1992), 199-204.

Zablocki, J., et al., "Novel Short Acting Coronary Vasodilators That Are Functionally Selective For The A2A Receptor Based On 2-Heterocyclic Substituted Adenosine Derivatives", *Drug Development Research*, 50 (1), Abstracts From Purines 2000: Biochemical, Pharmacological and Clinicai Perspectives: Abstract No. 059,(May 2000),p. 63.

"U.S. Appl. No. 11/739,680, Preliminary Amendment filed Apr. 24, 2007", 3 pgs.

"U.S. Appl. No. 11/739,680, Supplemental Preliminary Amendment filed Jul. 18, 2007", 6 pgs.

"U.S. Appl. No. 08/272,821, Notice of Allowance mailed Aug. 5, 1998", 3 pgs.

"U.S. Appl. No. 09/003,930, Non-Final Office Action mailed Nov. 4, 1998", 7 pgs.

"U.S. Appl. No. 09/003,930, Final Office Action mailed Aug, 6, 1999", 6 pgs.

"U.S. Appl. No. 09/003,930, Preliminary Amendment filed Feb. 8, 1999", 5 pgs.

"U.S. Appl. No. 09/003,930, Response filed May 4, 1999 to Non-Final Office Action mailed Nov. 4, 1998", 12 pgs.

"U.S. Appl. No. 09/003,930, Response filed Nov. 4, 1999 to Final Office Action mailed Aug. 6, 1999", 10 pgs.

"U.S. Appl. No. 09/333,387, Non-Final Office Action mailed Jul. 13, 2000", 5 pgs.

"U.S. Appl. No. 09/333,387, Notice of Allowance mailed Mar. 7, 2001", 4 pgs.

"U.S. Appl. No. 09/333,387, Notice of Allowance mailed Aug. 25, 2000", 2 pgs.

"U.S. Appl. No. 09/333,387, Supplemental Amendment filed Aug. 28, 2000", 2 pgs.

"U.S. Appl. No. 09/543,385, Notice of Allowance mailed Mar. 25, 2002", 5 pgs.

"U.S. Appl. No. 09/543,385, Notice of Allowance mailed Sep. 24, 2001", 5 pgs.

"U.S. Appl. No. 09/543,385, Preliminary Amendment filed Apr. 4, 2000", 2 pgs.

"U.S. Appl. No. 09/543,385, Supplemental Preliminary Amendment filed Aug. 31, 2000", 6 pgs.

"U.S. Appl. No. 09/827,083, Notice of Allowance mailed Sep. 10, 2002", 6 pgs.

"U.S. Appl. No. 09/827,083, Preliminary Amendment mailed Apr. 5, 2001", 5 pgs.

"U.S. Appl. No. 09/827,083, Response filed Dec. 10, 2002 to Notice of Allowance mailed Sep. 10, 2002", 2 pgs.

"U.S. Appl. No. 10/263,379 Advisory Action mailed Mar. 1, 2006", 7 pgs.

"U.S. Appl. No. 10/263,379 Advisory Action mailed Apr. 11, 2006", 5 pgs.

"U.S. Appl. No. 10/263,379 Final Office Action mailed Nov. 1, 2006", 6 pgs.

"U.S. Appl. No. 10/263,379 Final Office Action mailed Nov. 9, 2005", 17 pgs.

"U.S. Appl. No. 10/263,379 Final Office Action mailed Nov. 23, 2004", 46 pgs.

"U.S. Appl. No. 10/263,379 Non Final Office Action mailed Apr. 25, 2005", 15 pgs.

"U.S. Appl. No. 10/263,379 Non Final Office Action mailed Jun. 14, 2006", 10 pgs.

"U.S. Appl. No. 10/263,379 Non Final Office Action mailed Jun. 17, 2004", 54 pgs.

"U.S. Appl. No. 10/263,379 Notice of allowance mailed Dec. 12, 2006", 5 pgs.

"U.S. Appl. No. 10/263,379 Response filed Feb. 8, 2006 to Final Office Action mailed Nov. 9, 2005", 19 pgs.

"U.S. Appl. No. 10/263,379 Response filed Feb. 23, 2005 to Final Office Action mailed Nov. 23, 2004", 20 pgs.

"U.S. Appl. No. 10/263,379 Response filed Apr. 4, 2006 to Advisory Action mailed Mar. 1, 2006", 19 pgs.

"U.S. Appl. No. 10/263,379 Response filed May 2, 2006 to Advisory Action mailed Apr. 11, 2006", 15 pgs.

"U.S. Appl. No. 10/263,379 Response filed Sep. 11, 2006 to Non Final Office Action mailed Jun. 14, 2006", 15 pgs.

"U.S. Appl. No. 10/263,379 Response filed Sep. 26, 2005 to Non Final Office Action mailed Apr. 25, 2005", 19 pgs.

"U.S. Appl. No. 10/263,379 Response filed Oct. 18, 2004 to Non Final Office Action mailed Jun. 17, 2004", 25 pgs.

"U.S. Appl. No. 10/263,379 Response filed Nov. 21, 2006 to Final Office Action mailed Nov. 1, 2006", 13 pgs.

"U.S. Appl. No. 10/379,154, Final Office Action mailed Feb. 17, 2004", 4 pgs.

"U.S. Appl. No. 10/379,154, Final Office Action mailed Mar. 3, 2006", 5 pgs.

"U.S. Appl. No. 10/379,154, Non-Final Office Action mailed Jun. 17, 2004", 4 pgs.

"U.S. Appl. No. 10/379,154, Non-Final Office Action mailed Aug. 1, 2005", 5 pgs.

"U.S. Appl. No. 10/379,154, Non-Final Office Action mailed Aug. 8, 2003", 4 pgs.

"U.S. Appl. No. 10/379,154, Non-Final Office Action mailed Dec. 15, 2004", 5 pgs.

"U.S. Appl. No. 10/379,154, Notice of Allowance mailed Jan. 4, 2007", 5 pgs.

"U.S. Appl. No. 10/379,154, Response filed Apr. 4, 2007 to Notice of Allowance and Allowability mailed Jan. 4, 2007", 3 pgs.

"U.S. Appl. No. 10/379,154, Response filed May 16, 2005 to Non-Final Office Action mailed Dec. 15, 2004", 7 pgs.

"U.S. Appl. No. 10/379,154, Response filed May 17, 2004 to Final Office Action mailed Feb. 17, 2004", 6 pgs.

"U.S. Appl. No. 10/379,154, Response filed May 31, 2006 to Final Office Action mailed Mar. 30, 2006", 7 pgs.

"U.S. Appl. No. 10/379,154, Response filed Sep. 17, 2004 to Non-Final Office Action Jun. 17, 2004", 6 pgs.

"U.S. Appl. No. 10/379,154, Response filed Nov. 6, 2003 to Non-Final Office Action mailed Aug. 8, 2003", 8 pgs.

"U.S. Appl. No. 10/379,154, Response filed Dec. 1, 2005 to Non-Final Office Action mailed Aug. 1, 2005", 7 pgs.

"U.S. Appl. No. 10/412,726 Final office action mailed Oct. 8, 2004", 28 pgs.

"U.S. Appl. No. 10/412,726 Final office action mailed Dec. 5, 2005", 13 pgs.

"U.S. Appl. No. 10/412,726 Non Final office action mailed Mar. 16, 2005", 15 pgs.

"U.S. Appl. No. 10/412,726 Non Final office action mailed Apr. 7, 2004", 25 pgs.

"U.S. Appl. No. 10/412,726 Non Final office action mailed Oct. 30, 2006", 18 pgs.

"U.S. Appl. No. 10/412,726 Response filed Feb. 8, 2005 to Final Office action mailed Oct. 8, 2004", 22 pgs.

"U.S. Appl. No. 10/412,726 Response filed Apr. 27, 2007 to Non Final office action mailed Oct. 30, 2006", 23 pgs.

"U.S. Appl. No. 10/412,726 Response filed May 5, 2006 to Final office action mailed Dec. 5, 2005", 23 pgs.

"U.S. Appl. No. 10/412,726 Response filed Jul. 9, 2004 to Non Final office action mailed Apr. 7, 2004", 20 pgs.

"U.S. Appl. No. 10/412,726 Response filed Sep. 16, 2005 to Non Final office action mailed Mar. 16, 2005", 25 pgs.

"U.S. Appl. No. 10/412,726 Final Office Action mailed Jul. 19, 2007", FOAR, 10 pgs.

"U.S. Appl. No. 10/412,726, response filed Oct. 31, 2007 to Final Office Action mailed Jul. 19, 2007.", 28 pgs.

"New Zealand Application No. 556354 Non Final Office Action mailed Aug. 28, 2007", 28 pgs.

"Prosecution File History for U.S. Appl. No. 10/263,379", 264 pgs.

"Prosecution File History for U.S. Appl. No. 10/379,154", 105 pgs.

"Prosecution File History for U.S. Appl. No. 10/412,726", 189 pgs.

"Prosecution File History for U.S. Appl. No. 09/827,083", 20 pgs.

* cited by examiner

METHOD TO REDUCE INFLAMMATORY RESPONSE IN TRANSPLANTED TISSUE

CROSS-REFERENCE TO RELATED APPLICATIONS

This application is a continuation-in-part of U.S. patent application Ser. No. 10/379,154, filed Mar. 3, 2003; which is a continuation of U.S. patent application Ser. No. 09/827,083, filed Apr. 5, 2001, issued as U.S. Pat. No. 6,531,457, on Mar. 11, 2003; which is a continuation of U.S. application Ser. No. 09/333,387, filed Jun. 15, 1999, now U.S. Pat. No. 6,232,297, issued May 15, 2001, which claims priority of U.S. provisional patent application Ser. Nos. 60/118,029, filed Feb. 1, 1999, 60/124,316, filed Mar. 12, 1999, 60/133,374, filed May 10, 1999 and 60/135,573, filed May 24, 1999 all of which are incorporated by reference herein.

This application is also a continuation-in-part of U.S. application Ser. No. 10/263,379, filed Oct. 1, 2002, now U.S. Pat. No. 7,214,665, issued May 8, 2007, which claims priority from U.S. provisional patent application Ser. No. 60/326,517, filed Oct. 1, 2001, and U.S. provisional patent application Ser. No. 60/383,200, filed May 24, 2002, all of which are incorporated by reference herein.

GOVERNMENT FUNDING

The invention described herein was made with government support under Grant Number (R01-HL37942), awarded by the National Institutes of Health. The United States Government has certain rights in the invention.

BACKGROUND OF THE INVENTION

The inflammatory response serves the purpose of eliminating harmful agents from the body. There is a wide range of pathogenic insults that can initiate an inflammatory response including infection, allergens, autoimmune stimuli, immune response to transplanted tissue, noxious chemicals, and toxins, ischemia/reperfusion, hypoxia, mechanical and thermal trauma. Inflammation normally is a very localized action which serves in expulsion, attenuation by dilution, and isolation of the damaging agent and injured tissue. The body's response becomes an agent of disease when it results in inappropriate injury to host tissues in the process of eliminating the targeted agent, or responding to a traumatic insult.

As examples, inflammation is a component of pathogenesis in several vascular diseases or injuries. Examples include: ischemia/reperfusion injury (N. G. Frangogiannis et al., in *Myocardial Ischemia: Mechanisms, Reperfusion, Protection*, M. Karmazyn, ed., Birkhuser Verlag (1996) at 236-284; H. S. Sharma et al., *Med. of Inflamm.*, 6, 175 (1987)), atherosclerosis (R. Ross, *Nature*, 362, 801 (1993)), inflammatory aortic aneurysms (N. Girardi et al., *Ann. Thor. Surg.*, 64, 251 (1997); D. I. Walker et al., *Brit. J. Surg.*, 59, 609 (1972); R. L. Pennell et al., *J. Vasc. Surg.*, 2, 859 (1985)), and restenosis following balloon angioplasty (see, R. Ross cited above). The cells involved with inflammation include leukocytes (i.e., the immune system cells—neutrophils, eosinophils, lymphocytes, monocytes, basophils, macrophages, dendritic cells, and mast cells), the vascular endothelium, vascular smooth muscle cells, fibroblasts, and myocytes.

The release of inflammatory cytokines such as tumor necrosis factor-alpha (TNFα) by leukocytes is a means by which the immune system combats pathogenic invasions, including infections. TNFα stimulates the expression and activation of adherence factors on leukocytes and endothelial cells, primes neutrophils for an enhanced inflammatory response to secondary stimuli and enhances adherent neutrophil oxidative activity. See, Sharma et al., cited above. In addition, macrophages/dendritic cells act as accessory cells processing antigen for presentation to lymphocytes. The lymphocytes, in turn, become stimulated to act as pro-inflammatory cytotoxic cells.

Generally, cytokines stimulate neutrophils to enhance oxidative (e.g., superoxide and secondary products) and nonoxidative (e.g., myeloperoxidase and other enzymes) inflammatory activity. Inappropriate and over-release of cytokines can produce counterproductive exaggerated pathogenic effects through the release of tissue-damaging oxidative and nonoxidative products (K. G. Tracey et al., *J. Exp. Med.*, 167, 1211 (1988); and D. N. Männel et al., *Rev. Infect. Dis.*, 9 (suppl. 5), S602-S606 (1987)). For example, TNFα can induce neutrophils to adhere to the blood vessel wall and then to migrate through the vessel to the site of injury and release their oxidative and non-oxidative inflammatory products.

Although monocytes collect slowly at inflammatory foci, given favorable conditions, the monocytes develop into long-term resident accessory cells and macrophages. Upon stimulation with an inflammation trigger, monocytes/macrophages also produce and secrete an array of cytokines (including TNFα), complement, lipids, reactive oxygen species, proteases and growth factors that remodel tissue and regulate surrounding tissue functions.

For example, inflammatory cytokines have been shown to be pathogenic in: arthritis (C. A. Dinarello, *Semin. Immunol.*, 4, 133 (1992)); ischemia (A. Seekamp et al., *Agents-Actions-Supp.*, 41, 137 (1993)); septic shock (D. N. Männel et al., *Rev. Infect. Dis.*, 9 (suppl. 5), S602-S606 (1987)); asthma (N. M. Cembrzynska et al., *Am. Rev. Respir. Dis.*, 147, 291 (1993)); organ transplant rejection (D. K. Imagawa et al., *Transplantation*, 51, 57 (1991); multiple sclerosis (H. P. Hartung, *Ann. Neurol.*, 33, 591 (1993)); AIDS (T. Matsuyama et al., *AIDS*, 5, 1405 (1991)); and in alkali-burned eyes (F. Miyamoto et al., *Opthalmic Res.*, 30, 168 (1997)). In addition, superoxide formation in leukocytes has been implicated in promoting replication of the human immunodeficiency virus (HIV) (S. Legrand-Poels et al., *AIDS Res. Hum. Retroviruses*, 6, 1389 (1990)).

One disease that can be treated via transplantation is diabetes mellitus. The incidence of diabetes mellitus is predicted to increase significantly in the next decade, and it already affects an estimated 130 million people worldwide. Diabetes affects 16 million Americans and consumes one out of every eight health care dollars. Despite the efficacy of insulin therapy, the devastating secondary complications, including nephropathy, neuropathy, retinopathy, and cardiovascular disease, can shorten life expectancy by as much as one third.

One method for treatment of diabetes is β-cell replacement therapy. This treatment is the best way to achieve ideal blood glucose control and stop the progression of the secondary complications of Diabetes. Islet transplantation is an attractive alternative to either insulin injection or whole organ pancreas transplantation. This method avoids the technical complications of solid-organ pancreas transplantation, related to thrombosis of the blood supply to the whole-organ allograft and the danger of activation of the digestive enzymes associated with the exocrine function. In addition, islet transplantation provides the opportunity to manipulate the islets prior to transplantation in order to decrease immunogenicity of the allograft.

Unfortunately, many recipients need 2 to 3 transplantations to achieve insulin independence even after transplantation of more than 250,000 Ieq. According to statistics, while the number of patients in the USA who are diagnosed with type I diabetes annually is about 30,000, the number of pancreas donated for transplantation is approximately 6000. These donated pancreases are not solely used for islet transplantation.

The majority of islet grafts are lost early after transplantation (within the first 3 days post-transplantation, more than half of islet grafts will die). Growing evidence implicates a nonspecific inflammatory reaction in the host microenvironment at the site of islet implantation and transplantation as one of the main reasons for islet graft early death.

Islets are believed to be highly sensitive to the toxic effects of inflammatory mediators. P-selectin exposed on activated platelets can also stimulate monocytes and macrophages to secrete chemokines that are deleterious to islets. The high concentrations of TNF-a, IL-1b, and NO generated at the site of the allograft may also have direct toxic effects on islets. Moreover, isolated human islets are also believed to express many genes involved in the generation of inflammatory responses after isolation. The expression of IL-1$\beta$, IL-8, MIP-2, MCP-1, and MIF have been found to rise after the isolation procedure, and after transplantation this upregulation may induce an intense inflammation and enhance subsequent specific immune response. As a result of this initial strong inflammatory response, subsequent antigen presentation would probably be promoted, leading to accelerated and reinforced cell mediated immunity in a later phase.

The detrimental effects of this instant inflammatory reaction may provide a reasonable explanation for the relatively low success rates in clinical islet transplantation and may explain the need for islets from several donors to obtain normoglycemia in the transplant recipient. Strategies to efficiently inhibit these cascade reactions at the time of transplantation and during the first postoperative days may be of great importance in improving the outcome of clinical islet transplantation.

It is well known that adenosine and some analogs of adenosine that nonselectively activate adenosine receptor subtypes decrease neutrophil production of inflammatory oxidative products (B. N. Cronstein et al., *Ann. N.Y. Acad. Sci.*, 451, 291 (1985); P. A. Roberts et al., *Biochem. J.*, 227, 669 (1985); D. J. Schrier et al., *J. Immunol.*, 137, 3284 (1986); B. N. Cronstein et al., *Clinical Immunol. and Immunopath.*, 42, 76 (1987); M. A. Iannone et al., in *Topics and Perspective in Adenosine Research*, E. Gerlach et al., eds., Springer-Verlag, Berlin, p. 286 (1987); S. T. McGarrity et al., *J. Leukocyte Biol.*, 44, 411421 (1988); J. De La Harpe et al., *J. Immunol.*, 143, 596 (1989); S. T. McGarrity et al., *J. Immunol.*, 142, 1986 (1989); and C. P. Nielson et al., *Br. J. Pharmacol.*, 97, 882 (1989)). For example, adenosine has been shown to inhibit superoxide release from neutrophils stimulated by chemoattractants such as the synthetic mimic of bacterial peptides, f-met-leu-phe (fMLP), and the complement component $C_5$a (B. N. Cronstein et al., *J. Immunol.*, 135, 1366 (1985)). Adenosine can decrease the greatly enhanced oxidative burst of PMN (neutrophil) first primed with TNF-$\alpha$ and then stimulated by a second stimulus such as f-met-leu-phe (G. W. Sullivan et al., *Clin. Res.*, 41, 172A (1993)). Additionally, it has been reported that adenosine can decrease the rate of HIV replication in a T-cell line (S. Sipka et al., *Acta. Biochim. Biopys. Hung.*, 23, 75 (1988)). However, there is no evidence that in vivo adenosine has anti-inflammatory activity (G. S. Firestein et al., *Clin. Res.*, 41, 170A (1993); and B. N. Cronstein et al., *Clin. Res.*, 41, 244A (1993)).

It has been suggested that there is more than one subtype of adenosine receptor on neutrophils that can have opposite effects on superoxide release (B. N. Cronstein et al., *J. Clin. Invest.*, 85, 1150 (1990)). The existence of $A_{2A}$ receptor on neutrophils was originally demonstrated by Van Calker et al. (D. Van Calker et al., *Eur. J. Pharmacology*, 206, 285 (1991)).

There has been progressive development of compounds that are more and more potent and/or selective as agonists of $A_{2A}$ adenosine receptors (AR) based on radioligand binding assays and physiological responses. Initially, compounds with little or no selectivity for $A_{2A}$ receptors were developed, such as adenosine itself or 5'-carboxamides of adenosine, such as 5'-N-ethylcarboxamidoadenosine (NECA) (B. N. Cronstein et al., *J. Immunol.*, 135, 1366 (1985)). Later, it was shown that addition of 2-alkylamino substituents increased potency and selectivity, e.g., CV1808 and CGS21680 (M. F. Jarvis et al., *J. Pharmacol. Exp. Ther.*, 251, 888 (1989)). 2-Alkoxy-substituted adenosine derivatives such as WRC-0090 are even more potent and selective as agonists at the coronary artery $A_{2A}$ receptor (M. Ueeda et al., *J. Med. Chem.*, 34, 1334 (1991)). The 2-alklylhydrazino adenosine derivatives, e.g., SHA 211 (also called WRC-0474) have also been evaluated as agonists at the coronary artery $A_{2A}$ receptor (K. Niiya et al., *J. Med. Chem.*, 35, 4557 (1992)).

There is one report of the combination of relatively non-specific adenosine analogs, R-phenylisopropyladenosine (R-PIA) and 2-chloroadenosine (Cl-Ado) with a phosphodi-esterase (PDE) inhibitor resulting in a lowering of neutrophil oxidative activity (M. A. Iannone et al., *Topics and Perspectives in Adenosine Research*, E. Garlach et al., eds., Springer-Verlag, Berlin, pp. 286-298 (1987)). However, R-PIA and Cl-Ado analogs are actually more potent activators of $A_1$ adenosine receptors than of $A_{2A}$ adenosine receptors and, thus, are likely to cause side effects due to activation of $A_1$ receptors on cardiac muscle and other tissues causing effects such as "heart block."

There remains a need for compounds that are useful for treating an inflammatory response caused by an immune response to transplanted tissue and that can enhance the survival rate of transplanted organs after transplantation.

SUMMARY OF THE INVENTION

The present invention provides a therapeutic method for treating an inflammatory response caused by an immune response to transplanted tissue, comprising the administration to a patient in need thereof of an effective amount of an $A_{2A}$ adenosine receptor agonist. In one embodiment, the immune response is a transplant rejection, or graft versus host disease.

The present invention also provides method for transplanting tissues (cells) or organs in a mammal in need thereof wherein the method includes treatment of an inflammatory response, caused by an immune response to transplanted tissue (e.g., bone marrow, cornea, kidney, lung, liver, heart, skin, pancreatic islets) including transplant rejection, and graft versus host disease, with $A_{2A}$ adenosine receptor agonists.

The agonists of $A_{2A}$ adenosine receptors of the invention can inhibit neutrophil, macrophage and T cell activation and thereby reduce inflammation caused immune responses. The effects of adenosine $A_{2A}$ agonists can be enhanced by type IV phosphodiesterase inhibitors such as rolipram.

The invention also provides compounds of the invention for use in medical therapy (e.g., for use as an adjunct in the treatment of an inflammatory response, caused by an immune response to transplanted tissue, e.g., bone marrow, cornea, kidney, lung, liver, heart, skin, pancreatic islets) including transplant rejection, and graft versus host disease, with $A_{2A}$ adenosine receptor agonists, as well as the use of a compound of the invention for the manufacture of a medicament for reducing inflammation caused by the bacteria or virus or the treatment thereof in a mammal, such as a human.

In another aspect, the present invention also provides a method to treat an inflammatory response caused by an immune response to transplanted tissue including administering to a mammal in need of said therapy, an effective anti-inflammatory amount of an agonists of $A_{2A}$ adenosine receptor, optionally with a PDE-UV inhibitor, such as, rolipram.

The invention provides a compound of formula I for use in medical therapy, preferably for use in treating inflammation or protecting mammalian tissue from inflammation such as an inflammatory response, e.g., resulting from allergy, trauma or ischemia/reperfusion injury, as well as the use of a compound of formula I for the manufacture of a medicament for the treatment of an inflammatory response due to a pathological condition or symptom in a mammal, such as a human, which is associated with inflammation.

Although certain $A_{2A}$ adenosine receptor agonists have been reported to be vasodilators, and thus to be useful to directly treat hypertension, thrombus, atherosclerosis and the like, the tissue-protective anti-inflammatory activity of the compounds of formula of the invention are not suggested by the prior art.

The invention also includes the use of a combination of these compounds with type IV phosphodiesterase inhibitors to preferably cause synergistic decreases in the inflammatory response mediated by leukocytes.

The invention also provides a pharmaceutical composition comprising an effective amount of the compound of formula I, or a pharmaceutically acceptable salt thereof, in combination with a pharmaceutically acceptable diluent or carrier, and optionally, in combination with a Type IV phosphodiesterase (PDE) inhibitor. Preferably, the composition is presented as a unit dosage form.

Additionally, the invention provides a therapeutic method for preventing or treating a pathological condition or symptom in a mammal, such as a human, wherein the activity of $A_{2A}$ adenosine receptors is implicated and agonism of said receptors is desired, comprising administering to a mammal in need of such therapy, an effective amount of a compound of formula I, or a pharmaceutically acceptable salt thereof. It is believed that activation of $A_{2A}$ adenosine receptors inhibits inflammation by affecting neutrophils, mast cells, monocytes/macrophages, platelets T-cells and/or eosinophils. Inhibition of these inflammatory cells results in tissue protection following tissue insults.

Among the inflammatory responses that can be treated (including treated prophylactically) with a compound of formula I, optionally with a Type IV PDE inhibitor, are inflammation due to:

(a) autoimmune stimulation (autoimmune diseases), such as lupus erythematosus, multiple sclerosis, infertility from endometriosis, type I diabetes mellitus including the destruction of pancreatic islets leading to diabetes and the inflammatory consequences of diabetes, including leg ulcers, Crohn's disease, ulcerative colitis, inflammatory bowel disease, osteoporosis and rheumatoid arthritis;

(b) allergic diseases such as asthma, hay fever, rhinitis, poison ivy, vernal conjunctivitis and other eosinophil-mediated conditions;

(c) skin diseases such as psoriasis, contact dermatitis, eczema, infectious skin ulcers, open wounds, cellulitis;

(d) infectious diseases including sepsis, septic shock, encephalitis, infectious arthritis, endotoxic shock, gram negative shock, Jarisch-Herxheimer reaction, anthrax, plague, tularemia, ebola, shingles, toxic shock, cerebral malaria, bacterial meningitis, acute respiratory distress syndrome (ARDS), lyme disease, HIV infection, (TNFα-enhanced HIV replication, TNFα inhibition of reverse transcriptase inhibitor activity);

(e) wasting diseases: cachexia secondary to cancer and HIV;

(f) organ, tissue or cell transplantation (e.g., bone marrow, cornea, kidney, lung, liver, heart, skin, pancreatic islets) including transplant rejection, and graft versus host disease;

(g) adverse effects from drug therapy, including adverse effects from amphotericin B treatment, adverse effects from immunosuppressive therapy, e.g., interleukin-2 treatment, adverse effects from OKT3 treatment, contrast dyes, antibiotics, adverse effects from GM-CSF treatment, adverse effects of cyclosporine treatment, and adverse effects of aminoglycoside treatment, stomatitis and mucositis due to immunosuppression;

(h) cardiovascular conditions including circulatory diseases induced or exasperated by an inflammatory response, such as ischemia, atherosclerosis, peripheral vascular disease, restenosis following angioplasty, inflammatory aortic aneurysm, vasculitis, stroke, spinal cord injury, congestive heart failure, hemorrhagic shock, ischemia/reperfusion injury, vasospasm following subarachnoid hemorrhage, vasospasm following cerebrovascular accident, pleuritis, pericarditis, and the cardiovascular complications of diabetes;

(i) dialysis, including pericarditis, due to peritoneal dialysis;

(j) gout; and (k) chemical or thermal trauma due to burns, acid, alkali and the like.

Unexpectedly, it was found that administration of one or more compounds of formula (I) was effective after the onset of the inflammatory response, e.g., after the subject was afflicted with the pathology or trauma that initiates the inflammatory response.

Tissue or cells comprising ligand bound receptor sites can be used to measure the selectively of test compounds for specific receptor subtypes, the amount of bioactive compound in blood or other physiological fluids, or can be used as a tool to identify potential therapeutic agents for the treatment of diseases or conditions associated with receptor site activation, by contacting said agents with said ligand-receptor complexes, and measuring the extent of displacement of the ligand and/or binding of the agent, or the cellular response to said agent (e.g., cAMP accumulation).

DETAILED DESCRIPTION OF THE INVENTION

Figure 1:
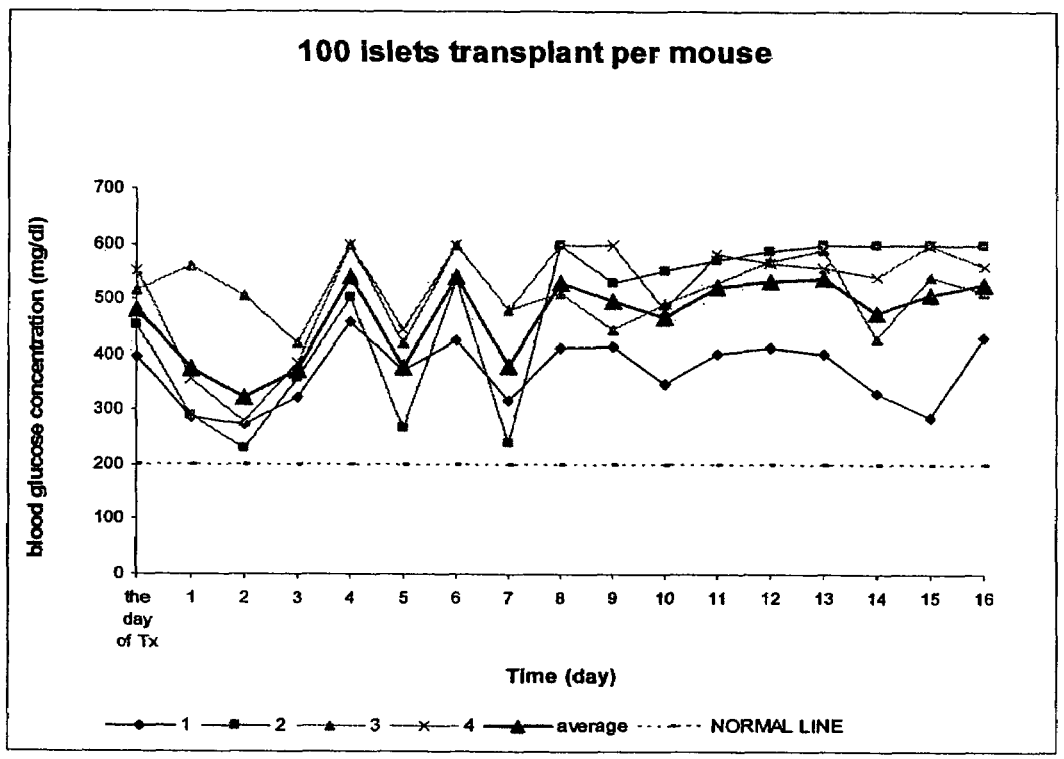
FIG. 1 shows blood glucose levels in mg/dL over time in a model for tissue rejection in mice, where the mice have received a transplant of 100 insulin-producing pancreatic islets, in the absence of any compound of the invention.

The following definitions are used, unless otherwise described. Halo is fluoro, chloro, bromo, or iodo. Alkyl, alkoxy, aralkyl, alkylaryl, etc. denote both straight and branched alkyl groups; but reference to an individual radical such as "propyl" embraces only the straight chain radical, a branched chain isomer such as "isopropyl" being specifically referred to. Aryl includes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five or six ring atoms consisting of carbon and one to four heteroatoms each selected from the group consisting of non-peroxide oxygen, sulfur, and N(X) wherein X is absent or is H, O, $(C_1-C_4)$alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

It will be appreciated by those skilled in the art that the compounds of formulas (I), (II), (III), and (IV) have more than one chiral center and may be isolated in optically active and racemic forms. Preferably, the riboside moiety of the compounds is derived from D-ribose, i.e., the 3',4'-hydroxyl groups are alpha to the sugar ring and the 2' and 5' groups is beta (3R, 4S, 2R, 5S). When the two groups on the cyclohexyl group are in the 1- and 4-position, they are preferably trans. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, or enzymatic techniques, by synthesis from optically-active starting materials, by chiral synthesis, or by chromatographic separation using a chiral stationary phase) and how to determine adenosine agonist activity using the tests described herein, or using other similar tests which are well known in the art.

Specific and preferred values listed below for radicals, substituents, and ranges, are for illustration only; they do not exclude other defined values or other values within defined ranges for the radicals and substituents.

Specifically, $(C_1-C_8)$alkyl can be methyl, ethyl, propyl, isopropyl, butyl, iso-butyl, sec-butyl, pentyl, 3-pentyl, hexyl, heptyl or octyl. As used herein, the term "cycloalkyl" encompasses bicycloalkyl (norbornyl, 2.2.2-bicyclooctyl, etc.) and tricycloalkyl (adamantyl, etc.), optionally comprising 1-2 N, O or S. Cycloalkyl also encompasses (cycloalkyl)alkyl. Thus, $(C_3-C_6)$cycloalkyl can be cyclopropyl, cyclobutyl, cyclopentyl, cyclohexyl and the like. $(C_1-C_8)$alkoxy can be methoxy, ethoxy, propoxy, isopropoxy, butoxy, iso-butoxy, sec-butoxy, pentoxy, 3-pentoxy, or hexyloxy; $(C_2-C_6)$alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl; $(C_2-C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_1-C_6)$alkanoyl can be acetyl, propanoyl or butanoyl; halo$(C_1-C_6)$alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy$(C_1-C_6)$alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; $(C_1-C_6)$alkoxycarbonyl ($CO_2R^2$) can be methoxycarbonyl, ethoxycarbonyl, propoxycarbonyl, isopropoxycarbonyl, butoxycarbonyl, pentoxycarbonyl, or hexyloxycarbonyl; $(C_1-C_6)$alkylthio can be methylthio, ethylthio, propylthio, isopropylthio, butylthio, isobutylthio, pentylthio, or hexylthio, $(C_2-C_6)$alkanoyloxy can be acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazoyl, isoxazoyl, thiazolyl, isothiazoyl, pyraxolyl, pyrrolyl, pyrazinyl, tetrazolyl, puridyl (or its N-oxide), thienyl, pyrimidinyl (or its N-oxide), indolyl, isoquinolyl (or its N-oxide) or quinolyl (or its N-oxide).

Aryl denotes a phenyl radical or an ortho-fused bicyclic carbocyclic radical having about nine to ten ring atoms in which at least one ring is aromatic. Heteroaryl denotes a radical of a monocyclic aromatic ring containing five or six ring atoms consisting of carbon and 1, 2, 3, or 4 heteroatoms each selected from the group consisting of non-peroxide oxygen, sulfur, and N(Y) wherein Y is absent or is H, O, $(C_1-C_8)$alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

The term "heterocycle" generally represents a non aromatic heterocyclic group, having from 3 to about 10 ring atoms, which can be saturated or partially unsaturated, containing at least one heteroatom (e.g., 1, 2, or 3) selected from the group consisting of oxygen, nitrogen, and sulfur. Specific, "heterocycle" groups include monocyclic, bicyclic, or tricyclic groups containing one or more heteroatoms selected from the group consisting of oxygen, nitrogen, and sulfur. A "heterocycle" group also can include one or more oxo groups (=O) attached to a ring atom. Non-limiting examples of heterocycle groups include 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholine, piperazinyl, piperidine, piperidyl, pyrazolidine, pyrazolidinyl, pyrazolinyl, pyrrolidine, pyrroline, quinuelidine, thiomorpholine, and the like.

The term "alkylene" refers to a divalent straight or branched hydrocarbon chain (e.g. ethylene —CH$_2$CH$_2$—).

The term "aryl(C$_1$-C$_8$)alkylene" for example includes benzyl, phenethyl, 3-phenylpropyl, naphthylmethyl and the like.

As used herein the term "in conjunction with" refers to co-administration of an anti-rejection agent with the A$_{2A}$ adenosine receptor agonist. The co-administration of an agent and an A$_{2A}$ adenosine receptor agonists includes administration of the agent and agonist either simultaneously, as a mixture, or sequentially. The sequential administration of the A$_{2A}$ adenosine receptor agonists can be prior to administration of the agent, within minutes or up to about 48 hours either before the administration of the agent. The A$_{2A}$ adenosine receptor agonists can also be administered after the agent. Preferably the administration of the A$_{2A}$ adenosine receptor agonists will be within about 24 hours and more preferably within about 12 hours.

In one embodiment, the patient is administered the A$_{2A}$ adenosine receptor agonists prior to transplantation. In another embodiment, the patient is implanted with a pump containing the A$_{2A}$ adenosine receptor agonists prior to transplantation.

The carbon atom content of various hydrocarbon-containing moieties is indicated by a prefix designating the minimum and maximum number of carbon atoms in the moiety, i.e., the prefix C$_i$-C$_j$ indicates a moiety of the integer "i" to the integer "j" carbon atoms, inclusive. Thus, for example, (C$_1$-C$_8$)alkyl refers to alkyl of one to eight carbon atoms, inclusive.

The compounds of the present invention are generally named according to the IUPAC or CAS nomenclature system. Abbreviations which are well known to one of ordinary skill in the art may be used (e.g., "Ph" for phenyl, "Me" for methyl, "Et" for ethyl, "h" for hour or hours and "rt" for room temperature).

In one embodiment, agonists of A$_{2A}$ adenosine receptors that are useful in the practice of the present invention include compounds having the formula (I):

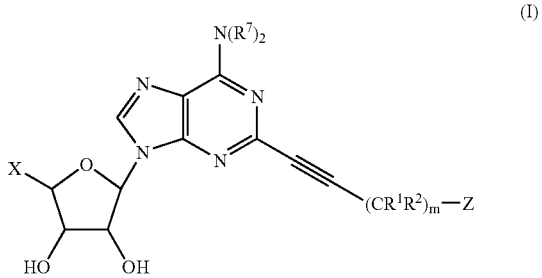

(I)

wherein

Z is CR$^3$R$^4$R$^5$ or NR$^4$R$^5$; each R$^1$ is independently hydrogen, halo, —OR$^a$, —SR$^a$, (C$_1$-C$_8$)alkyl, cyano, nitro, trifluoromethyl, trifluoromethoxy, (C$_3$-C$_8$)cycloalkyl, heterocycle, heterocycle(C$_1$-C$_8$)alkylene-, aryl, aryl(C$_1$-C$_8$)alkylene-, heteroaryl, heteroaryl(C$_1$-C$_8$)alkylene-, —CO$_2$R$^a$, R$^a$C(=O)O—, R$^a$C(=O)—, —OCO$_2$R$^a$, R$^b$R$^c$NC(=O)O—, R$^a$OC(=O)N(R$^b$)—, R$^b$R$^c$N—, R$^b$R$^c$NC(=O)—, R$^a$C(=O)N(R$^b$)—, R$^b$R$^c$NC(=O)N(R$^b$)—, R$^b$R$^c$NC(=S)N(R$^b$)—, —OPO$_3$R$^a$, R$^a$OC(=S)—, R$^a$C(=S)—, —SSR$^a$, R$^a$S(=O)—, R$^a$S(=O)$_2$—, or —N=NR$^b$;

each R$^2$ is independently hydrogen, halo, (C$_1$-C$_8$)alkyl, (C$_3$-C$_8$)cycloalkyl, heterocycle, heterocycle(C$_1$-C$_8$)alkylene-, aryl, aryl(C$_1$-C$_8$)alkylene-, heteroaryl, or heteroaryl (C$_1$-C$_8$)alkylene-; or R$^1$ and R$^2$ and the atom to which they are attached is C=O, C=S or C=NR$^d$, R$^4$ and R$^5$ together with the atoms to which they are attached form a saturated or partially unsaturated, mono-, bicyclic- or aromatic ring having 3, 4, 5, 6, 7, 8, 9 or 10 ring atoms optionally comprising 1, 2, 3, or 4 heteroatoms selected from non-peroxide oxy (—O—), thio (—S—), sulfinyl (—SO—), sulfonyl (—S(O)$_2$—) or amine (—NR$^b$—) in the ring;

wherein any ring comprising R$^4$ and R$^5$ is substituted with from 1 to 14 R$^6$ groups; wherein each R$^6$ is independently halo, —OR$^a$, —SR$^a$, (C$_1$-C$_8$)alkyl, cyano, nitro, trifluoromethyl, trifluoromethoxy, (C$_1$-C$_8$)cycloalkyl, (C$_6$-C$_{12}$)bicycloalkyl, heterocycle or heterocycle (C$_1$-C$_8$)alkylene-, aryl, aryl (C$_1$-C$_8$)alkylene-, heteroaryl, heteroaryl(C$_1$-C$_8$)alkylene-, —CO$_2$R$^a$, R$^a$C(=O)O—, R$^a$C(=O)—, —OCO$_2$R$^a$, R$^b$R$^c$NC(=O)O—, R$^a$OC(=O)N(R$^b$)—, R$^b$R$^c$N—, R$^b$R$^c$NC(=O)—, R$^a$C(=O)N(R$^b$)—, R$^b$R$^c$NC(=O)N(R$^b$)—, R$^b$R$^c$NC(=S)N(R$^b$)—, —OPO$_3$R$^a$, R$^a$OC(=S)—, R$^a$C(=S)—, —SSR$^a$, R$^a$S(=O)—, —NNR$^b$, or two R$^6$ groups and the atom to which they are attached is C=O, C=S or; two R groups together with the atom or atoms to which they are attached can form a carbocyclic or heterocyclic ring;

R$^3$ is hydrogen, halo, —OR$^a$, —SR$^a$, (C$_1$-C$_8$)alkyl, cyano, nitro, trifluoromethyl, trifluoromethoxy, (C$_3$-C$_8$)cycloalkyl, heterocycle, heterocycle(C$_1$-C$_8$)alkylene-, aryl, aryl(C$_1$-C$_8$) alkylene-, heteroaryl, heteroaryl(C$_1$-C$_8$)alkylene-, —CO$_2$R$^a$, R$^a$C(=O)O—, R$^a$C(=O)—, —OCO$_2$R$^a$, R$^b$R$^c$NC(=O)O—, R$^a$OC(=O)N(R$^b$)—, R$^b$R$^c$N—, R$^b$R$^c$NC(=O)—, R$^a$C(=O)N(R$^b$)—, R$^b$R$^c$NC(=O)N(R$^b$)—, R$^b$R$^c$NC(=S)N(R$^b$)—, —OPO$_3$R$^a$, R$^a$OC(=S)—, R$^a$C(=S)—, —SSR$^a$, R$^a$S(=O)—, R$^a$S(=O)$_2$—, —NNR$^b$; or if the ring formed from CR$^4$R$^5$ is aryl or heteroaryl or partially unsaturated then R$^3$ can be absent;

each R$^7$ is independently hydrogen, (C$_1$-C$_8$)alkyl, (C$_3$-C$_8$) cycloalkyl, aryl or aryl(C$_1$-C$_8$)alkylene, heteroaryl, heteroaryl(C$_1$-C$_8$)alkylene-;

X is —CH$_2$OR$^a$, —CO$_2$R$^a$, —OC(O)R$^a$, —CH$_2$OC(O)R$^a$, —C(O)NR$^b$R$^b$, —CH$_2$SR$^a$, —C(S)OR$^a$, —OC(S)R$^a$, —CH$_2$OC(S)R$^a$ or —C(S)NR$^b$R$^c$ or —CH$_2$N(R$^b$)(R$^c$);

wherein any of the alkyl, cycloalkyl, heterocycle, aryl, or heteroaryl, groups of R$^1$, R$^2$, R$^3$, R$^6$ and R$^7$ is optionally substituted on carbon with one or more (e.g. 1, 2, 3, or 4) substituents selected from the group consisting of halo, —OR$^a$, —SR$^a$, (C$_1$-C$_8$)alkyl, cyano, nitro, trifluoromethyl, trifluoromethoxy, (C$_3$-C$_8$)cycloalkyl, (C$_6$-C$_{12}$)bicycloalkyl, heterocycle or heterocycle(C$_1$-C$_8$)alkylene-, aryl, aryloxy, aryl(C$_1$-C$_8$)alkylene-, heteroaryl, heteroaryl(C$_1$-C$_8$)alkylene-, —CO$_2$R$^a$, R$^a$C(=O)O—, R$^a$C(=O)—, —OCO$_2$R$^a$, R$^b$R$^c$NC(=O)O—, R$^a$OC(=O)N(R$^b$)—, R$^b$R$^c$N—, R$^b$R$^c$NC(=O)—, R$^a$C(=O)N(R$^b$)—, R$^b$R$^c$NC(=O)N(R$^b$)—, R$^b$R$^c$NC(=S)N(R$^b$)—, —OPO$_3$R$^a$, R$^a$OC(=S)—, R$^a$C(=S)—, —SSR$^a$, R$^a$S(=O)$_p$—, R$^b$R$^c$NS(O)$_p$—, and —N=NR$^b$;

wherein any (C$_1$-C$_8$)alkyl, (C$_3$-C$_8$)cycloalkyl, (C$_6$-C$_{12}$)bicycloalkyl, (C$_1$-C$_8$)alkoxy, (C$_1$-C$_8$)alkanoyl, (C$_1$-C$_8$)alkylene, or heterocycle, is optionally partially unsaturated;

each R$^a$, R$^b$ and R$^c$ is independently hydrogen, (C$_1$-C$_8$) alkyl, or (C$_1$-C$_8$)alkyl substituted with 1-3 (C$_1$-C$_8$)alkoxy, (C$_3$-C$_8$)cycloalkyl, (C$_1$-C$_8$)alkylthio, amino acid, aryl, aryl (C$_1$-C$_8$)alkylene, heteroaryl, or heteroaryl(C$_1$-C$_8$)alkylene; or R$^b$ and R$^c$, together with the nitrogen to which they are attached, form a pyrrolidino, piperidino, morpholino, or thiomorpholino ring; and R$^d$ is hydrogen or (C$_1$-C$_6$)alkyl; m is 0 to about 8 and p is 0 to 2; or a pharmaceutically acceptable salt thereof.

In another embodiment, the invention includes the use of compounds of formula (I) provided that when $CR^4R^5$ is a carbocyclic ring then at least one of $R^1$, $R^2$, or $R^3$ is a group other than hydrogen or at least one $R^6$ group is a group other than —$CH_2OH$, —$CO_2R^a$, $R^aC(=O)$—, $R^aC(=O)OCH_2$— or $R^bR^cNC(=O)$—; and provided that m is at least 1 when Z is $NR^4R^5$.

Specific and preferred values listed below for radicals, substituents, and ranges, are for illustration only; they do not exclude other defined values or other values within defined ranges for the radicals and substituents.

A specific immune response is an inflammatory response from a transplant rejection.

A specific transplant rejection is from an organ, tissue or cell transplantation.

Specific cells are bone marrow, skin, or pancreatic islets.

More specific cells are pancreatic islets.

Specific organs include a cornea, kidney, lung, liver, or heart.

A specific value for $R^1$ is hydrogen, —OH, —$CH_2OH$, —OMe, —OAc, —$NH_2$, —NHMe, —$NMe_2$ or —NHAc.

Another specific value for $R^1$ is hydrogen, —OH, —OMe, —OAc, —$NH_2$, —NHMe, —$NMe_2$ or —NHAc.

Another specific value for $R^1$ is hydrogen, —OH, —OMe, or —$NH_2$.

Another specific value for $R^1$ is hydrogen, —OH, or —$NH_2$.

A more specific value for $R^1$ is hydrogen or —OH.

A specific value for $R^1$, $R^2$ and the carbon atom to which they are attached is carbonyl (C=O).

A specific value for $R^2$ is hydrogen or $(C_1-C_8)$alkyl, cyclopropyl, cyclohexyl or benzyl.

Another specific value for $R^2$ is hydrogen, methyl, ethyl or propyl.

Another specific value for $R^2$ is hydrogen or methyl.

A more specific value for $R^2$ is hydrogen.

A specific value for $R^3$ is hydrogen, OH, OMe, OAc, $NH_2$, NHMe, $NMe_2$ or NHAc.

Another specific value for $R^3$ is hydrogen, OH, OMe, or $NH_2$.

Another specific value for $R^3$ is hydrogen, OH, or $NH_2$.

A more specific value for $R^3$ is hydrogen or OH.

A specific value for the ring comprising $R^4$, $R^5$ and the atom to which they are connected is cyclopentane, cyclohexane, piperidine, dihydro-pyridine, tetrahydro-pyridine, pyridine, piperazine, decaline, tetrahydro-pyrazine, dihydro-pyrazine, pyrazine, dihydro-pyrimidine, tetrahydro-pyrimidine, hexahydro-pyrimidine, pyrazine, imidazole, dihydro-imidazole, imidazolidine, pyrazole, dihydro-pyrazole, and pyrazolidine.

A more specific value for the ring comprising $R^4$ and $R^5$ and the atom to which they are connected is, cyclohexane, piperidine or piperazine.

A specific value for $R^6$ is $(C_1-C_8)$alkyl, or substituted $(C_1-C_8)$alkyl, —$OR^a$, —$CO_2R^a$, $R^aC(=O)$—, $R^aC(=O)$O—, $R^bR^cN$—, $R^bR^cNC(=O)$—, or aryl.

Another specific value for $R^6$ is $(C_1-C_8)$alkyl, —$OR^a$, —$CO_2R^a$, $R^aC(=O)$—, $R^aC(=O)O$—, $R^bR^cN$—, $R^bR^cNC(=O)$—, or aryl.

Another specific value for $R^6$ is methyl, ethyl, butyl, OH, $OR^a$, —$CO_2R^a$, $R^aC(=O)$—, $OC(=O)CH_2CH_3$, —$CONR^bR^c$, —$NR^bR^c$ or phenyl.

Another specific value for $R^6$ is OH, OMe, methyl, ethyl, t-butyl, —$CO_2R^a$, —$C(=O)NR^bR^c$, —OAc, —$NH_2$, —NHMe, —$NMe_2$, —NHEt or —$N(Et)_2$.

Another specific value for $R^6$ is —$(CH_2)_{1-2}OR^a$, —$(CH_2)_{1-2}C(=O)OR^a$, —$(CH_2)_{1-2}OC(=O)R^a$, —$(CH_2)_{1-2}$ $C(=O)R^a$, —$(CH_2)_{1-2}OCO_2R^a$, —$(CH_2)_{1-2}NHR^a$, —$(CH_2)_{1-2}NR^bR^c$, —$(CH_2)_{1-2}OC(=O)NHR^a$, or —$(CH_2)_{1-2}OC(=O)NR^bR^c$.

Another specific value for $R^6$ is —$CH_2OH$, —$CH_2OAc$, —$CH_2OCH_3$, —$CH_2C(=O)OCH_3$, —$CH_2C(=O)CH_3$, —$CH_2C(=O)CH_3$, —$CH_2OCO_2CH_3$, —$CH_2NH(CH_3)$, or —$(CH_2)_{1-2}N(CH_3)_2$.

Another specific value for $R^6$ is methyl, ethyl, t-butyl, phenyl, —$CO_2R^a$, —$CONR^bR^c$, or $R^aC(=O)$—.

Another specific value for $R^6$ is —$CH_2OH$, —$CH_2OAc$, —$C(=O)OCH_3$, —$C(=O)CH_3$, $OCO_2CH_3$—$OCO_2CH_3$, —$CH_2NH(CH_3)$, or —$(CH_2)_{1-2}N(CH_3)_2$.

A more specific value for $R^6$ is methyl, ethyl, —$CO_2R^a$— $CONR^bR^c$, or $R^aC(=O)$—.

A specific number of $R^6$ groups substituted on the $R^4R^5$ ring is from 1 to about 4.

Specific values for $R^a$ and $R^b$ are independently hydrogen, $(C_1-C_4)$alkyl, aryl or aryl$(C_1-C_8)$alkylene.

More specific values for $R^a$ and $R^b$ are independently hydrogen, methyl, ethyl, phenyl or benzyl.

A more specific value for $R^a$ is $(C_1-C_8)$alkyl.

Another specific value for $R^a$ is methyl, ethyl, propyl or butyl.

A more specific value for $R^a$ is methyl, ethyl, i-propyl, i-butyl or tert-butyl.

Another specific value for $R^b$ and $R^c$ is a ring.

A specific value for $R^7$ is hydrogen, alkyl, aryl or aryl $(C_1-C_8)$alkylene.

Another specific value for $R^7$ is hydrogen, methyl or ethyl, phenyl or benzyl.

A more specific value for $R^7$ is H, or methyl.

A specific value for —$N(R^7)_2$ is amino, methylamino, dimethylamino, ethylamino, pentylamino, diphenylethylamino, pyridylmethylamino, diethylamino or benzylamino.

A specific value for —$N(R^7)_2$ is amino, methylamino, dimethylamino, ethylamino, diethylamino diphenylethylamino, pentylamino or benzylamino.

A specific value for $N(R^7)_2$ is amino, or methylamino.

A specific value for X is —$CH_2OR^a$, —$CO_2R^a$, —OC(O)$R^a$, —$CH_2OC(O)R^a$, —$C(O)NR^bR^c$.

Another specific value for X is —$CH_2OR^a$ or —$C(O)NR^bR^c$.

A more specific value for X is —$CH_2OH$ or —$C(O)NHCH_2CH_3$.

A specific value for m is 0, 1, or 2.

A more specific value for m is 0, or 1.

Specific examples of rings comprising $R^4$, $R^5$ and the atom to which they are connected include:

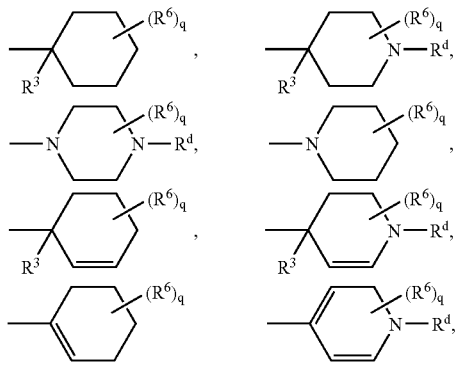

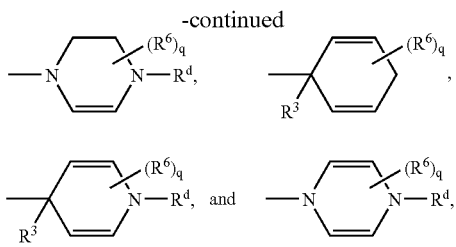

where q is from 0 to 14 and $R^d$ is hydrogen, provided that when q is zero then $R^d$ is not hydrogen.

More specific examples of rings comprising $R^4$, $R^5$ and the atom to which they are connected include:

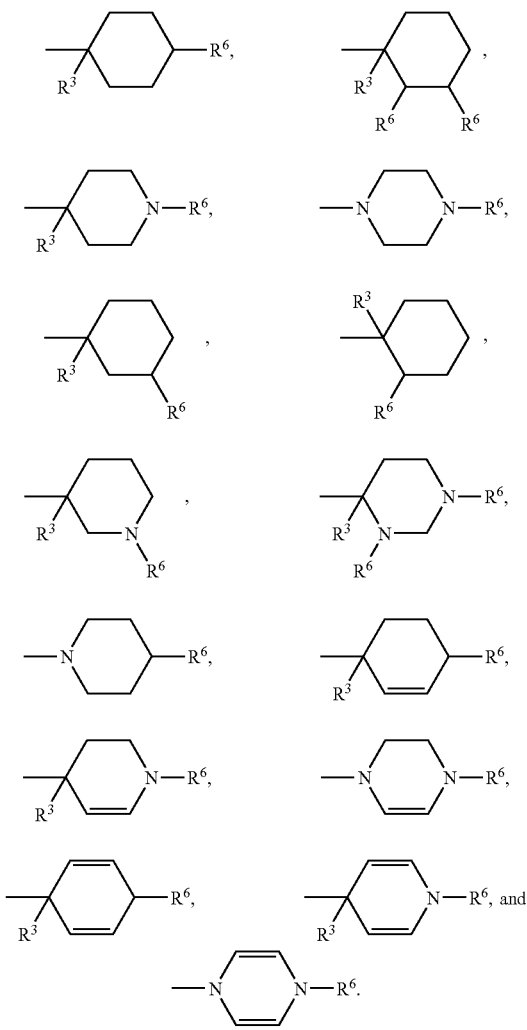

Specific values for the ring comprising $R^4$, $R^5$ and the atom to which they are connected are 2-methyl cyclohexane, 2,2-dimethylcyclohexane, 2-phenylcyclohexane, 2-ethylcyclohexane, 2,2-diethylcyclohexane, 2-tert-butyl cyclohexane, 3-methyl cyclohexane, 3,3-dimethylcyclohexane, 4-methyl cyclohexane, 4-ethylcyclohexane, 4-phenyl cyclohexane, 4-tert-butyl cyclohexane, 4-carboxymethyl cyclohexane, 4-carboxyethyl cyclohexane, 3,3,5,5-tetramethyl cyclohexane, 2,4-dimethyl cyclopentane. 4-cyclohexanecarboxyic acid, 4-cyclohexanecarboxyic acid esters, or 4-methyloxyalkanoyl-cyclohexane.

More specific values for the ring comprising $R^4$, $R^5$ and the atom to which they are connected are 4-piperidine, 4-piperidene-1-carboxylic acid, 4-piperidine-1-carboxylic acid methyl ester, 4-piperidine-1-carboxylic acid ethyl ester, 4-piperidine-1-carboxylic acid propyl ester, 4-piperidine-1-carboxylic acid tert-butyl ester, 1-piperidine, 1-piperidine-4-carboxylic acid methyl ester, 1-piperidine-4-carboxylic acid ethyl ester, 1-piperidine-4-carboxylic acid propyl ester, 1-piperidine-4-caboxylic acid tert-butyl ester, 1-piperidine-4-carboxylic acid methyl ester, 3-piperidine, 3-piperidene-1-carboxylic acid, 3-piperidine-1-carboxylic acid methyl ester, 3-piperidine-1-carboxylic acid tert-butyl ester, 1,4-piperazine, 4-piperazine-1-carboxylic acid, 4-piperazine-1-carboxylic acid methyl ester, 4-piperazine-1-carboxylic acid ethyl ester, 4-piperazine-1-carboxylic acid propyl ester, 4-piperazine-1-carboxylic acid tert-butylester, 1,3-piperazine, 3-piperazine-1-carboxylic acid, 3-piperazine-1-carboxylic acid methyl ester, 3-piperazine-1-carboxylic acid ethyl ester, 3-piperazine-1-carboxylic acid propyl ester, 3-piperidine-1-carboxylic acid tert-butylester, 1-piperidine-3-carboxylic acid methyl ester, 1-piperidine-3-carboxylic acid ethyl ester, 1-piperidine-3-carboxylic acid propyl ester or 1-piperidine-3-caboxylic acid tert-butyl ester.

Another group of specific values for the ring comprising $R^4$ and $R^5$ are 2-methyl cyclohexane, 2,2-dimethylcyclohexane, 2-phenyl cyclohexane, 2-ethylcyclohexane, 2,2-diethylcyclohexane, 2-tert-butyl cyclohexane, 3-methyl cyclohexane, 3,3-dimethylcyclohexane, 4-methyl cyclohexane, 4-ethylcyclohexane, 4-phenyl cyclohexane, 4-tert-butyl cyclohexane, 4-carboxymethyl cyclohexane, 4-carboxyethyl cyclohexane, 3,3,5,5-tetramethyl cyclohexane, 2,4-dimethyl cyclopentane, 4-piperidine-1-carboxylic acid methyl ester, 4-piperidine-1-carboxylic acid tert-butyl ester 4-piperidine, 4-piperazine-1-carboxylic acid methyl ester, 4-piperidine-1-carboxylic acid tert-butylester, 1-piperidine-4-carboxylic acid methyl ester, 1-piperidine-4-caboxylic acid tert-butyl ester, tert-butylester, 1-piperidine-4-carboxylic acid methyl ester, or 1-piperidine-4-caboxylic acid tert-butyl ester, 3-piperidine-1-carboxylic acid methyl ester, 3-piperidine-1-carboxylic acid tert-butyl ester, 3-piperidine, 3-piperazine-1-carboxylic acid methyl ester, 3-piperidine-1-carboxylic acid tert-butylester, 1-piperidine-3-carboxylic acid methyl ester, 1-piperidine-3-caboxylic acid tert-butyl ester.

Specific compounds of formula (I) are those wherein each $R^7$ is H, X is ethylaminocarbonyl and
$R^1$ is hydroxy, $R^2$ is hydrogen, and Z is 4-carboxycyclohexyl, wherein $R^a$ is hydrogen, 4; Z is 4-methoxycarbonylcyclohexylmethyl, $R^a$ is methyl, 5; $R^1$ and $R^2$ together are oxo, Z is a 4-carbonylcyclohexyl group, wherein $R^a$ is methyl, methoxy, ethyl, ethoxy, propyl, isopropoxy, -isobutyl, tert-butyl, amine, methylamine or dimethylamine, 6.

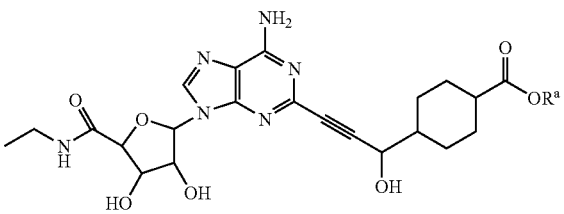

4, $R^a$ is H
5, $R^a$ is $CH_3$

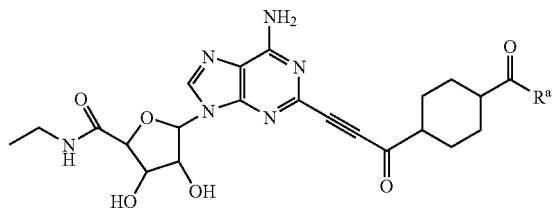

6

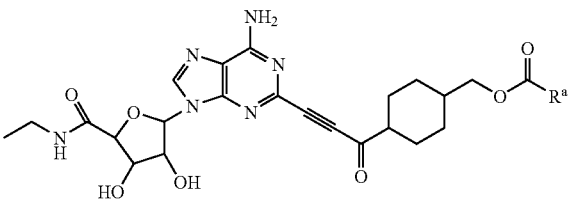

8

Another group of specific compounds of formula (I) are those wherein each $R^7$ is H, X is ethylaminocarbonyl, $R^1$ is hydroxy, $R^2$ is hydrogen, and Z is a substituted 4-(methyleneoxycarbonyl)cyclohexyl group, wherein $R^a$ is methyl, ethyl, propyl, tert-butyl, methoxy, ethoxy, methylamine or dimethylamine, 7; or $R^1$ and $R^2$ together are oxo, and Z is a substituted-(methyleneoxycarbonyl)cyclohexyl group, wherein $R^a$ is methyl, ethyl, propyl, tert-butyl, methoxy, ethoxy, methylamine or dimethylamine, 8.

Another group of specific compounds of formula (I) are those wherein each $R^7$ is H, X is ethylaminocarbonyl, and $R^1$ and $R^2$ are each hydrogen, and Z is a 1-piperidyl-4-carboxylic acid or ester group, wherein $R^a$ is hydrogen, methyl, ethyl, propyl, isopropyl, or t-butyl, 9; $R^1$ and $R^2$ together are oxo, and Z is a 1-piperidyl-4-carboxylic acid or ester group, wherein $R^a$ is hydrogen, methyl, ethyl, propyl, isopropyl, or t-butyl, 10; $R^1$ and $R^2$ are each hydrogen and Z is a 4-(methyleneoxycarbonyl)piperidin-4-yl group wherein $R^a$ is methyl, ethyl, propyl or t-butyl, amine, methylamine, dimethylamine, 11; or $R^1$ and $R^2$ together are oxo, and Z is a 4-(methyleneoxycarbonyl)piperidin-4-yl wherein $R^a$ is methyl, ethyl, propyl or t-butyl, amine, methylamine, dimethylamine, 12; $R^1$ and $R^2$ are each hydrogen and Z is a 4-(methyleneoxycarbonyl)piperidin-4-yl-oxy wherein $R^a$ is hydrogen, methyl, ethyl, propyl isopropyl, isobutyl, or t-butyl, 13 or $R^1$ and $R^2$ together are oxo, Z is a 4-(methyleneoxycarbonyl)piperidin-4-yl-oxy wherein $R^a$ is hydrogen, methyl, ethyl, propyl, isopropyl, isobutyl, or t-butyl, 14.

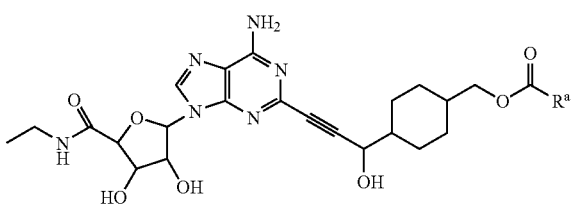

7

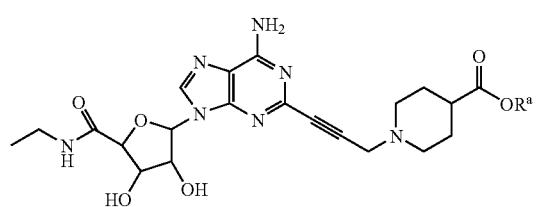

9

10

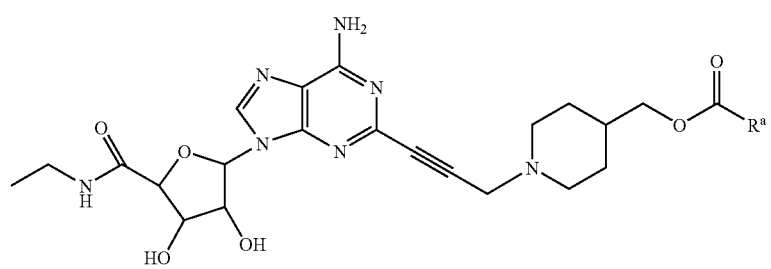

11

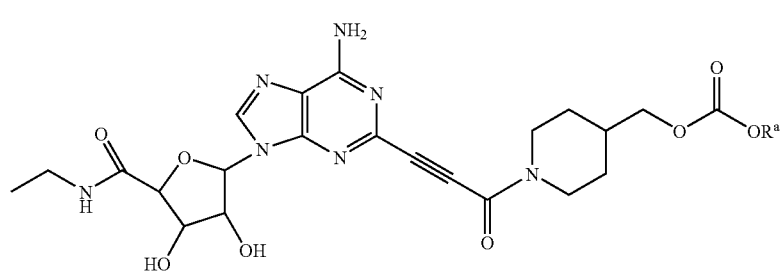

12

-continued

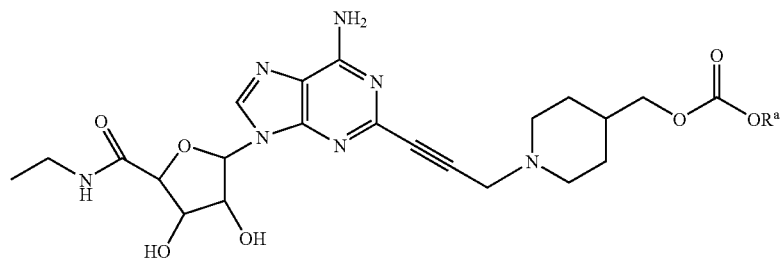

13

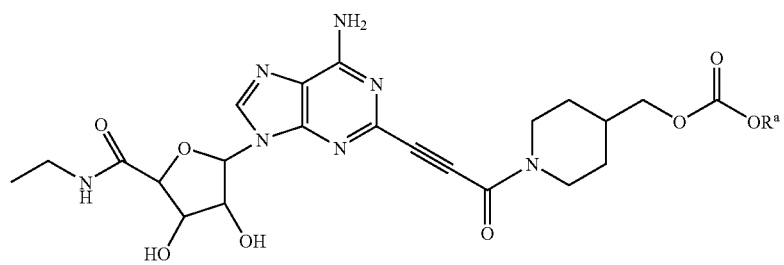

14

Another group of specific compounds of formula (I) are those wherein each $R^7$ is H, X is ethylaminocarbonyl, $R^1$ and $R^2$ are each hydrogen, and Z is a 4-piperidyl-1-carboxylic acid or ester group, wherein $R^a$ is methyl, ethyl, propyl, isopropyl, isobutyl, or t-butyl, 15, $R^1$ is hydroxy, $R^2$ is hydrogen, and Z is a 4-piperidyl-1-carboxylic acid or ester group, wherein $R^a$ is methyl, ethyl, propyl, isopropyl, isobutyl, or t-butyl, 16; or $R^1$ and $R^2$ together are oxo, and Z is a 4-piperidyl-1-carboxylic acid or ester group, wherein $R^a$ is methyl, ethyl, propyl, isopropyl, isobutyl, or t-butyl, 17.

Another group of specific compounds of formula (I) are those wherein each $R^7$ is H, X is ethylaminocarbonyl, $R^1$ and $R^2$ are each hydrogen, Z is a 4-piperazine-1-carboxylic acid or ester group wherein $R^a$ is methyl, ethyl, isopropyl, isobutyl, or t-butyl, 18; or $R^1$ and $R^2$ together are oxo, Z is a 4-piperazine-1-carboxylic acid or ester group wherein $R^a$ is methyl, ethyl, isopropyl, isobutyl, or t-butyl, 19.

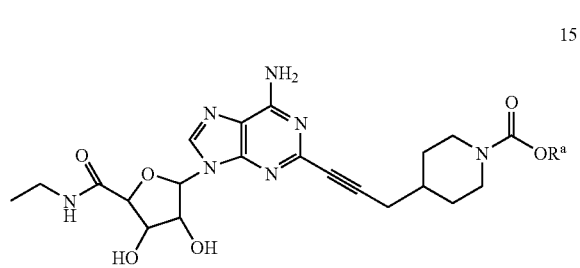

15

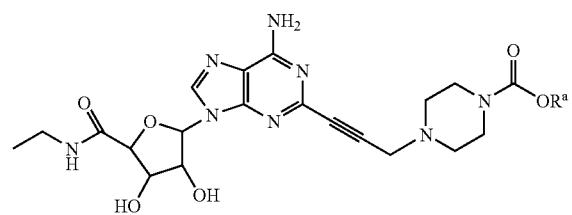

18

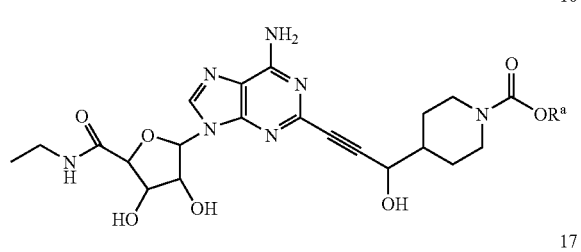

16

17

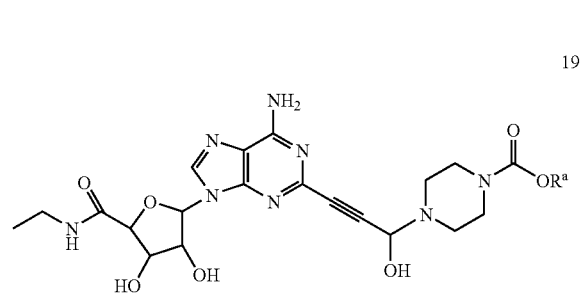

19

Specific $A_{2A}$ adenosine receptor agonists suitable for use with the present invention include those described in U.S. Pat. No. 6,232,297 and in U.S. Patent Application No. 2003/0186926 A1.

Examples of compounds useful in practicing the invention are illustrated in tables 1, 2, 3, 4, 5, 6 and 7 below:

TABLE 1

| Compound | R | $R^1$ | $R^2$ | $R^6$ |
|---|---|---|---|---|
| ATL2037 | NECA | H | H | $CH_2OH$ |
| MP9056 | NECA | OH | H | $CH_2OH$ |
| ATL146a | NECA | H | H | $CO_2H$ |
| MP9057 | NECA | OH | H | $CO_2H$ |
| ATL146e | NECA | H | H | $CO_2Me$ |
| MP9058 | NECA | OH | H | $CO_2Me$ |
| JR2145 | $CH_2OH$ | H | H | $CO_2Me$ |
| MP9059 | $CH_2OH$ | OH | H | $CO_2Me$ |
| ATL193 | NECA | H | H | $CH_2OAc$ |
| MP9060 | NECA | OH | H | $CH_2Oac$ |
| JR2147 | $CH_2OH$ | H | H | $CH_2Oac$ |
| MP9061 | $CH_2OH$ | OH | H | $CH_2Oac$ |
| JR3023 | NECA | H | H | $CH_2N(CH_3)_2$ |
| MP9062 | NECA | OH | H | $CH_2N(CH_3)_2$ |
| JR3021 | NECA | H | H | $COOCH_2CH_2NHBoc$ |
| MP9063 | NECA | OH | H | $COOCH_2CH_2NHBoc$ |
| JR3033 | NECA | H | H | $COOCH_2CH_2NH_2$ |
| MP9064 | NECA | OH | H | $COOCH_2CH_2NH_2$ |
| JR3037 | NECA | H | H | $CONHCH_2CH_3$ |
| MP9065 | NECA | OH | H | $CONHCH_2CH_3$ |
| JR3055 | NECA | H | H | $CONH_2$ |
| MP9072 | NECA | OH | H | $CONH_2$ |
| JR3065 | NECA | H | H | CONHMe |
| MP9066 | NECA | OH | H | CONHMe |
| JR3067B | NECA | H | H | Me, cis $CO_2Me$ |
| MP9067 | NECA | OH | H | Me, cis $CO_2Me$ |
| JR3067A | NECA | H | H | Me, trans $CO_2Me$ |
| MP9068 | NECA | OH | H | Me, trans $CO_2Me$ |
| JR3087 | NECA | H | H | $CH_2CH_3$ |
| MP9069 | NECA | OH | H | $CH_2CH_3$ |
| JR3159A | NECA | OH | H | H |
| JR3159B | NECA | OH | H | H |
| JR3119 | NECA | H | H | $COCH_3$ |
| MP9070 | NECA | OH | H | $COCH_3$ |
| JR3121 | NECA | H | H | $CHCH_3(OH)$ |
| MP9071 | NECA | OH | H | $CHCH_3(OH)$ |
| JR3139 | NECA | OH | $C_6H_{11}$ | H |

NECA = $CH_3CH_2N(H)C(O)$—

TABLE 2

| Compound | $R^1$ | $R^2$ | $R^6$ |
|---|---|---|---|
| JR3261 | H | H | H |
| JR3259 | H | H | $CO_2tBu$ |
| JR3269 | H | H | $CO_2Et$ |
| JR4011 | H | H | $CO_2iBu$ |
| JR4009 | H | H | $CO_2iPr$ |
| JR4007 | H | H | $CO_2Me$ |
| JR4051 | H | H | $COC(CH_3)_3$ |
| JR4047 | H | H | $COCH_2(CH_3)_3$ |
| MP9047 | H | H | $COCH_3$ |
| MP9048 | H | H | $C(O)N(CH_3)_2$ |
| MP9049 | H | H | $C(O)N(CH_3)Et$ |
| MP9050 | H | H | $C(O)N(CH_3)iPr$ |
| MP9051 | H | H | $C(O)N(CH_3)iBu$ |
| MP9052 | H | H | $C(O)NH(CH_3)$ |
| MP9053 | H | H | $C(O)NH(Et)$ |
| MP9054 | H | H | $C(O)NH(iPr)$ |
| MP9055 | H | H | $C(O)NH(iBu)$ |
| TX3261 | OH | H | H |
| TX3259 | OH | H | $CO_2tBu$ |
| TX3269 | OH | H | $CO_2Et$ |
| TX4011 | OH | H | $CO_2iBu$ |
| TX4009 | OH | H | $CO_2iPr$ |
| TX4007 | OH | H | COMe |
| TX4051 | OH | H | $COC(CH_3)_3$ |
| TX4047 | OH | H | $COCH_2(CH_3)_3$ |
| TX9047 | OH | H | $COCH_3$ |
| TX9048 | OH | H | $C(O)N(CH_3)_2$ |
| TX9049 | OH | H | $C(O)N(CH_3)Et$ |
| TX9050 | OH | H | $C(O)N(CH_3)iPr$ |
| TX9051 | OH | H | $C(O)N(CH_3)iBu$ |
| TX9052 | OH | H | $C(O)NH(CH_3)$ |
| TX9053 | OH | H | $C(O)NH(Et)$ |
| TX9054 | OH | H | $C(O)NH(iPr)$ |
| TX9055 | OH | H | $C(O)NH(iBu)$ |

TABLE 3

| Compound | n | $R^3$ | $R^6$ |
|---|---|---|---|
| JR3135 | 1 | OH | H |
| JR3089 | 2 | OH | H |
| JR3205 | 2 | $NH_2$ | H |
| JR3177A | 2 | OH | 2-$CH_3$ |
| JR3177B | 2 | OH | 2-$CH_3$ |
| JR3181A | 2 | OH | 2-$CH_3$ |
| JR3181B | 2 | OH | 2-$CH_3$ |
| JR3227 | 2 | OH | 2-$C(CH_3)_3$ |
| JR9876 | 2 | OH | 2-$C_6H_5$ |
| JR3179 | 2 | OH | 3-$CH_3$ |

TABLE 3-continued

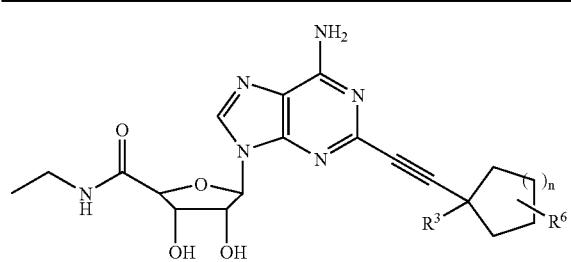

| Compound | n | R³ | R⁶ |
|---|---|---|---|
| JR3221 | 2 | OH(R) | 3-CH₃(R) |
| ATL203 | 2 | OH(S) | 3-CH₃(R) |
| MP9041 | 2 | OH(R) | 3-CH₃(S) |
| MP9042 | 2 | OH(S) | 3-CH₃(S) |
| JR3201B | 2 | OH | 2-(CH₃)₂ |
| MP9043 | 2 | OH(R) | 3-CH₂CH₃(R) |
| MP9044 | 2 | OH(S) | 3-CH₂CH₃(R) |
| MP9045 | 2 | OH(R) | 3-CH₂CH₃(S) |
| MP9046 | 2 | OH(S) | 3-CH₂CH₃(S) |
| JR3163 | 2 | OH | 3-(CH₃)₂, 5-(CH₃)₂ |
| JR9875 | 2 | OH | 4-CH₃ |
| JR3149 | 2 | OH | 4-C₂H₅ |
| JR3203 | 2 | OH | 4-C(CH₃)₃ |
| JR3161 | 2 | OH | 4-C₆H₅ |

TABLE 4

| Compound | R¹ | R² | R⁶ |
|---|---|---|---|
| JR3213 | H | H | CO₂Et |
| JR3281 | H | H | CO₂tBu |
| JR3289 | H | H | H |
| JR4025 | H | H | cyclohexyl |
| JR4053 | H | H | COMe |
| JR4049 | H | H | CO₂iBu |
| JR3283 | H | H | 2-Pyrimidinyl |
| MP9029 | H | H | COMe |
| MP9030 | H | H | COC(CH₃)₃ |
| MP9031 | H | H | COCH₂(CH₃)₃ |
| MP9032 | H | H | COCH₃ |
| MP9033 | H | H | C(O)N(CH₃)₂ |
| MP9034 | H | H | C(O)N(CH₃)Et |
| MP9035 | H | H | C(O)N(CH₃)iPr |
| MP9036 | H | H | C(O)N(CH₃)iBu |
| MP9037 | H | H | C(O)NH(CH₃) |
| MP9038 | H | H | C(O)NH(Et) |
| MP9039 | H | H | C(O)NH(iPr) |
| MP9040 | H | H | C(O)NH(iBu) |

TABLE 5

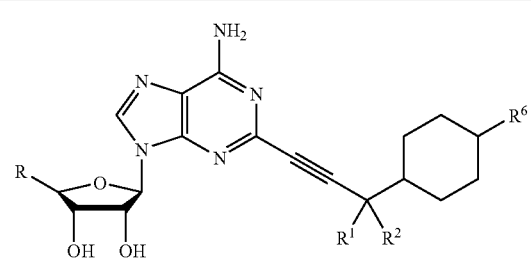

| Compound | R | R¹ | R² | R⁶ |
|---|---|---|---|---|
| MP9021 | NECA | H | H | CH₂OH |
| MP9022 | NECA | H | H | CO₂H |
| JR3251 | NECA | H | H | CO₂Me |
| JR3279 | NECA | H | H | CO₂Et |
| MP9027 | CH₂OH | H | H | CO₂Me |
| MP9028 | NECA | H | H | CO₂MeCH₂OAc |
| MP9015 | CH₂OH | H | H | CH₂OAc |
| MP9016 | NECA | H | H | CH₂N(CH₃)₂ |
| MP9017 | NECA | H | H | COOCH₂CH₂NHBoc |
| MP9018 | NECA | H | H | COOCH₂CH₂NH₂ |
| MP9019 | NECA | H | H | CONHCH₂CH₃ |
| MP9020 | NECA | H | H | CONH₂ |
| MP9023 | NECA | H | H | CONHMe |
| MP9024 | NECA | H | H | CH₂CH₃ |
| MP9025 | NECA | H | H | COCH₃ |
| MP9026 | NECA | H | H | CHCH₃(OH). |

NECA = CH₃CH₂N(H)C(O)—

TABLE 6

| Compound | R | R¹ | R² | R⁶ |
|---|---|---|---|---|
| MP9001 | NECA | H | H | CH₂OH |
| MP9002 | NECA | H | H | CO₂H |
| JR3253 | NECA | H | H | CO₂Me |
| MP9003 | CH₂OH | H | H | CO₂Me |
| MP9004 | NECA | H | H | CH₂OAc |
| MP9005 | CH₂OH | H | H | CH₂OAc |
| MP9006 | NECA | H | H | CH₂N(CH₃)₂ |
| MP9007 | NECA | H | H | COOCH₂CH₂NHBoc |
| MP9008 | NECA | H | H | COOCH₂CH₂NH₂ |
| MP9009 | NECA | H | H | CONHCH₂CH₃ |
| MP9010 | NECA | H | H | CONH₂ |
| MP9011 | NECA | H | H | CONHMe |
| MP9012 | NECA | H | H | CH₂CH₃ |
| MP9013 | NECA | H | H | COCH₃ |
| MP9014 | NECA | H | H | CHCH₃(OH) |

NECA = CH₃CH₂N(H)C(O)—

TABLE 7

Structure: adenine with NH$_2$, ribose with R and two OH groups, linked via C≡C-C(O)-Y-piperazine-Y'-R$^6$

| Compound | R | Y | Y' | R$^6$ |
|---|---|---|---|---|
| RJ1111 | NECA | CH | CH | CO$_2$Me |
| RJ1112 | NECA | CH | N | CO$_2$Me |
| RJ1113 | NECA | N | CH | CO$_2$Me |
| RJ1114 | NECA | N | N | CO$_2$Me |
| RJ1115 | NECA | CH | CH | CH$_2$OH |
| RJ1116 | NECA | CH | N | CH$_2$OH |
| RJ1117 | NECA | N | CH | CH$_2$OH |
| RJ1118 | NECA | N | N | CH$_2$OH |
| RJ1119 | NECA | CH | CH | CO$_2$H |
| RJ1120 | NECA | CH | N | CO$_2$H |
| RJ1121 | NECA | N | CH | CO$_2$H |
| RJ1122 | NECA | N | N | CO$_2$H |
| RJ1123 | NECA | CH | CH | CH$_2$OAc |
| RJ1124 | NECA | CH | N | CH$_2$OAc |
| RJ1125 | NECA | N | CH | CH$_2$OAc |
| RJ1126 | NECA | N | N | CH$_2$OAc |
| RJ1127 | NECA | CH | CH | CONH$_2$ |
| RJ1128 | NECA | CH | N | CONH$_2$ |
| RJ1129 | NECA | N | CH | CONH$_2$ |
| RJ1130 | NECA | N | N | CONH$_2$ |
| RJ1131 | NECA | CH | CH | CONHMe |
| RJ1132 | NECA | CH | N | CONHMe |
| RJ1133 | NECA | N | CH | CONHMe |
| RJ1134 | NECA | N | N | CONHMe |
| RJ1135 | NECA | CH | CH | CO$_2$tBu |
| RJ1136 | NECA | CH | N | CO$_2$tBu |
| RJ1137 | NECA | N | CH | CO$_2$tBu |
| RJ1138 | NECA | N | N | CO$_2$tBu |
| RJ1139 | NECA | CH | CH | CO$_2$Et |
| RJ1140 | NECA | CH | N | CO$_2$Et |
| RJ1141 | NECA | N | CH | CO$_2$Et |
| RJ1142 | NECA | N | N | CO$_2$Et |
| RJ1143 | NECA | CH | CH | CO$_2$iBu |
| RJ1144 | NECA | CH | N | CO$_2$iBu |
| RJ1145 | NECA | N | CH | CO$_2$iBu |
| RJ1146 | NECA | N | N | CO$_2$iBu |
| RJ1147 | NECA | CH | CH | CO$_2$iPr |
| RJ1148 | NECA | CH | N | CO$_2$iPr |
| RJ1149 | NECA | N | CH | CO$_2$iPr |
| RJ1150 | NECA | N | N | CO$_2$iPr |
| RJ1151 | NECA | CH | CH | COMe |
| RJ1152 | NECA | CH | N | COMe |
| RJ1153 | NECA | N | CH | COMe |
| RJ1154 | NECA | N | N | COMe |
| RJ1155 | NECA | CH | CH | COC(CH$_3$)$_3$ |
| RJ1156 | NECA | CH | N | COC(CH$_3$)$_3$ |
| RJ1157 | NECA | N | CH | COC(CH$_3$)$_3$ |
| RJ1158 | NECA | N | N | COCCH$_3$)$_3$ |
| RJ1159 | NECA | CH | CH | COCH$_2$CH$_3$)$_3$ |
| RJ1160 | NECA | CH | N | COCH$_2$CH$_3$)$_3$ |
| RJ1161 | NECA | N | CH | COCH$_2$(CH$_3$)$_3$ |
| RJ1162 | NECA | N | N | COCH$_2$(CH$_3$)$_3$ |
| RJ1163 | NECA | CH | CH | C(O)N(CH$_3$)$_2$ |
| RJ1164 | NECA | CH | N | C(O)N(CH$_3$)$_2$ |
| RJ1165 | NECA | N | CH | C(O)N(CH$_3$)$_2$ |
| RJ1166 | NECA | N | N | C(O)N(CH$_3$)$_2$ |
| RJ1167 | NECA | CH | CH | C(O)N(CH$_3$)Et |
| RJ1168 | NECA | CH | N | C(O)N(CH$_3$)Et |
| RJ1169 | NECA | N | CH | C(O)N(CH3)Et |
| RJ1170 | NECA | N | N | C(O)N(CH$_3$)Et |
| RJ1171 | NECA | CH | CH | C(O)N(CH$_3$)iPr |
| RJ1172 | NECA | CH | N | C(O)N(CH$_3$)iPr |
| RJ1173 | NECA | N | CH | C(O)N(CH$_3$)iPr |
| RJ1174 | NECA | N | N | C(O)N(CH$_3$)iPr |

TABLE 7-continued

| Compound | R | Y | Y' | R$^6$ |
|---|---|---|---|---|
| RJ1175 | NECA | CH | CH | C(O)N(CH$_3$)iBu |
| RJ1176 | NECA | CH | N | C(O)N(CH$_3$)iBu |
| RJ1177 | NECA | N | CH | C(O)N(CH$_3$)iBu |
| RJ1178 | NECA | N | N | C(O)N(CH$_3$)iBu |
| RJ1179 | NECA | CH | CH | C(O)NH(Et) |
| RJ1180 | NECA | CH | N | C(O)NH(Et) |
| RJ1181 | NECA | N | CH | C(O)NH(Et) |
| RJ1182 | NECA | N | N | C(O)NH(Et) |
| RJ1183 | NECA | CH | CH | C(O)NH(iPr) |
| RJ1184 | NECA | CH | N | C(O)NH(iPr) |
| RJ1185 | NECA | N | CH | C(O)NH(iPr) |
| RJ1186 | NECA | N | N | C(O)NH(iPr) |
| RJ1187 | NECA | CH | CH | C(O)NH(iBu) |
| RJ1188 | NECA | CH | N | C(O)NH(iBu) |
| RJ1189 | NECA | N | CH | C(O)NH(iBu) |
| RJ1190 | NECA | N | N | C(O)NH(iBu) |
| RJ1191 | NECA | CH | CH | CH$_2$OCOCH$_3$ |
| RJ1192 | NECA | N | CH | CH$_2$OCOCH$_3$ |
| RJ1193 | NECA | CH | CH | CH$_2$OCOEt |
| RJ1194 | NECA | N | CH | CH$_2$OCOEt |
| RJ1195 | NECA | CH | CH | CH$_2$OCOiPr |
| RJ1196 | NECA | N | CH | CH$_2$OCOiPr |
| RJ1197 | NECA | CH | CH | CH$_2$OCOiBu |
| RJ1198 | NECA | N | CH | CH$_2$OCOiBu |

NECA = O CH$_3$CH$_2$N(H)C(O)—

In another embodiment, agonists of A$_{2A}$ adenosine receptors that are useful in the practice of the present invention include compounds having the formula (II):

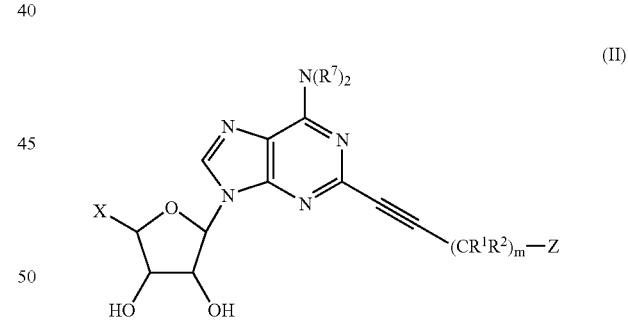

(II)

wherein Z is CR$^3$R$^4$R$^5$; each R$^1$, R$^2$ and R$^3$ is hydrogen; R$^4$ and R$^5$ together with the carbon atom to which they are attached form a cycloalkyl ring having 3, 4, 5, 6, 7, 8, 9 or 10 ring atoms; and wherein the ring comprising R$^4$ and R$^5$ is substituted with —(CH$_2$)$_{0-6}$—Y; where Y is —CH$_2$OR$^a$, —CO$_2$R$^a$, —OC(O)R$^a$, —CH$_2$OC(O)R$^a$, —C(O)NR$^b$R$^c$, —CH$_2$SR$^a$, —C(S)OR$^a$, —OC(S)R$^a$, —CH$_2$OC(S)R$^a$ or C(S)NR$^b$R$^c$ or —CH$_2$N(R$^b$)(R$^c$);

each R$^7$ is independently hydrogen, (C$_1$-C$_8$)alkyl, (C$_3$-C$_8$) cycloalkyl, aryl or aryl(C$_1$-C$_8$)alkylene;

X is —CH$_2$OR$^a$, —CO$_2$R$^a$, —OC(O)R$^a$, —CH$_2$OC(O)R$^a$, —C(O)NR$^b$R$^c$, —CH$_2$SR$^a$, —C(S)OR$^a$, —OC(S)R$^a$, —CH$_2$OC(S)R$^a$ or C(S)NR$^b$R$^c$ or —CH$_2$N(R$^b$)(R$^c$);

each $R^a$, $R^b$ and $R^c$ is independently hydrogen, $(C_1-C_8)$ alkyl, or $(C_1-C_8)$alkyl substituted with 1-3 $(C_1-C_8)$alkoxy, $(C_3-C_8)$cycloalkyl, $(C_1-C_8)$alkylthio, amino acid, aryl, aryl $(C_1-C_8)$alkylene, heteroaryl, or heteroaryl$(C_1-C_8)$alkylene; or $R^b$ and $R^c$, together with the nitrogen to which they are attached, form a pyrrolidino, piperidino, morpholino, or thiomorpholino ring; and m is 0 to about 6; or a pharmaceutically acceptable salt thereof.

A specific value for $—N(R^7)_2$ is amino, monomethylamino or cyclopropylamino.

A specific value for Z is carboxy- or $—(C_1-C_4)$alkoxycarbonyl-cyclohexyl$(C_1-C_4)$alkyl.

A specific value for $R^a$ is H or $(C_1-C_4)$alkyl, i.e., methyl or ethyl.

A specific value for $R^b$ is H, methyl or phenyl.

A specific value for $R^c$ is H, methyl or phenyl.

A specific value for $—(CR^1R^2)_m—$ is $—CH_2—$ or $—CH_2—CH_2—$.

A specific value for X is $CO_2R^a$, $(C_2-C_5)$alkanoylmethyl or amido.

A specific value for Y is $CO_2R^a$, $(C_2-C_5)$alkanoylmethyl or amido.

A specific value for m is 1.

Specific compounds useful for practicing the invention are compounds JR3259, JR3269, JR4011, JR4009, and JR4007.

Specific $A_{2A}$ adenosine receptor agonists suitable for use with the present invention having formula (II) include those described in U.S. Pat. No. 6,232,297. Specific compounds of formula (II) are those wherein each $R^7$ is H, X is ethylaminocarbonyl and Z is 4-carboxycyclohexylmethyl (DWH-146a), Z is 4-methoxycarbonylcyclohexylmethyl (DWH-146e), Z is 4-isopropylcarbonyl-cyclohexylmethyl (AB-1), Z is 4-acetoxymethyl-cyclohexylmethyl (JMR-193) or Z is 4-pyrrolidine-1-carbonylcyclohexylmethyl (AB-3). These compounds are depicted below.

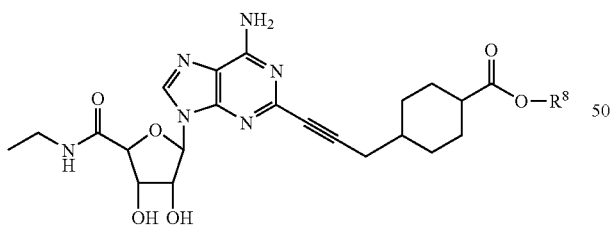

DWH-146:$R^8$ = H or Me.
AB-1:$R^8$ = iPr

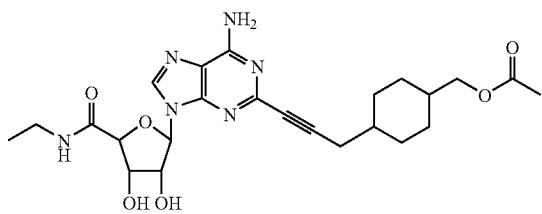

JMR-193

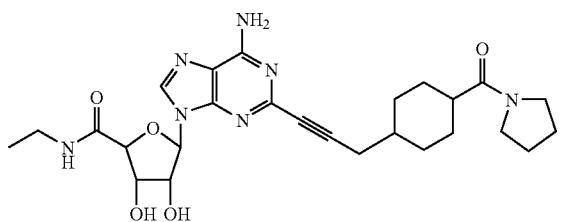

AB-3

The specific $A_{2A}$ adenosine receptor agonists suitable for use with the present invention having formula (II) include those described in U.S. Pat. No. 6,232,297. These compounds, having formula (II), can be prepared according to the methods described therein.

Another specific group of agonists of $A_{2A}$ adenosine receptors that are useful in the practice of the present invention include compounds having the general formula (III):

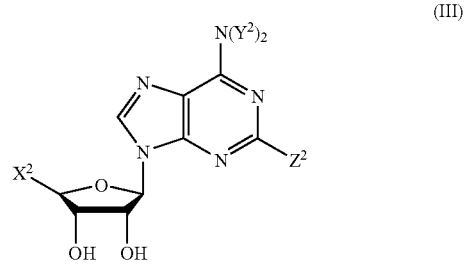

(III)

wherein $Z^2$ is a group selected from the group consisting of $—OR^{12}$, $—NR^{13}R^{14}$, a $—C≡C-Z^3$, and $—NH—N=R^{17}$;

each $Y^2$ is individually H, $C_1-C_6$ alkyl, $C_3-C_7$ cycloalkyl, phenyl or phenyl $C_1-C_3$ alkyl;

$R^{12}$ is a) $C_{1-4}$-alkyl;

b) $C_{1-4}$-alkyl substituted with one or more $C_{1-4}$-alkoxy groups, halogens (fluorine, chlorine or bromine), hydroxy groups, amino groups, mono($C_{1-4}$-alkyl)amino groups, di($C_{1-4}$-alkyl)amino groups or $C_{6-10}$-aryl groups wherein the aryl groups may be substituted with one or more halogens (fluorine, chlorine or bromine), $C_{1-4}$-alkyl groups, hydroxy groups, amino groups, mono ($C_{1-4}$-alkyl)amino groups or di($C_{1-4}$-alkyl)amino groups); or c) $C_{6-10}$-aryl; or (d) $C_{6-10}$-aryl substituted with one or more halogens (fluorine, chlorine or bromine), hydroxy groups, amino groups, mono($C_{1-4}$-alkyl)amino groups, di($C_{1-4}$-alkyl)amino groups or $C_{1-4}$-alkyl groups;

one of $R^{13}$ and $R^{14}$ has the same meaning as $R^{12}$ and the other is hydrogen; and R¹⁷ is a group having the formula (i)

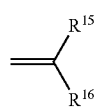
(i)

wherein each of $R^{15}$ and $R^{16}$ independently may be hydrogen, ($C_3$-$C_7$)cycloalkyl or any of the meanings of $R^{12}$, provided that $R^{15}$ and $R^{16}$ are not both hydrogen;

$X^2$ is $CH_2OH$, $CH_3$, $CO_2R^{20}$ or $C(=O)NR^{21}R^{22}$ wherein $R^{20}$ has the same meaning as $R^{13}$ and wherein $R^{21}$ and $R^{22}$ have the same meanings as $R^{15}$ and $R^{16}$ or $R^{21}$ and $R^{22}$ are both H;

$Z^3$ has one of the following meanings:

a) $C_6$-$C_{10}$ aryl, optionally substituted with one to three halogen atoms, $C_1$-$C_6$ alkyl, $C_1$-$C_6$ haloalkyl, $C_1$-$C_6$ alkoxy, $C_1$-$C_6$ haloalkoxy, $C_2$-$C_6$ alkoxycarbonyl, $C_2$-$C_6$ alkoxyalkyl, $C_1$-$C_6$ alkylthio, thio, CHO, cyanomethyl, nitro, cyano, hydroxy, carboxy, $C_2$-$C_6$ acyl, amino $C_1$-$C_3$ monoalkylamino, $C_2$-$C_6$ dialkylamino, methylenedioxy or aminocarbonyl;

b) a group of formula —$(CH_2)_q$-Het wherein q is 0 or an integer from 1 to 3 and Het is 5 or 6 membered heterocyclic aromatic or non-aromatic ring, optionally benzo-condensed, containing 1 to 3 heteroatoms selected from non-peroxide oxygen, nitrogen or sulphur, linked through a carbon atom or through a nitrogen atom;

c) $C_3$-$C_7$ cycloalkyl optionally containing unsaturation or $C_2$-$C_4$ alkenyl;

d)

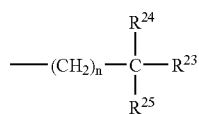
(ii)

wherein $R^{23}$ is hydrogen, methyl or phenyl;

$R^{24}$ is hydrogen, $C_1$-$C_6$ linear or branched alkyl, $C_5$-$C_6$ cycloalkyl or $C_3$-$C_7$ cycloalkenyl, phenyl-$C_1$-$C_2$-alkyl or $R^{23}$ and $R^{24}$, taken together, form a 5 or 6-membered carbocyclic ring or $R^{25}$ is hydrogen and $R^{23}$ and $R^{24}$, taken together, form an oxo group or a corresponding acetalic derivative;

$R^{25}$ is OH, $NH_2$ dialkylamino, halogen, cyano; and n is 0 or 1 to 4; or e) $C_1$-$C_{16}$ alkyl, optionally comprising 1-2 double bonds, O, S or $NY^2$; or a pharmaceutically acceptable salt thereof.

Specific $C_{6-10}$-aryl groups include phenyl and naphthyl.

Preferably, in the compound of formula (I), $Z^2$ is a group of the formula (iii)

—O—$(CH_2)_n$—Ar (iii)

wherein n is an integer from 1-4, preferably 2, and Ar is a phenyl group, tolyl group, naphthyl group, xylyl group or mesityl group. Most preferably Ar is a para-tolyl group and n=2.

Preferably, in the compound of formula (II), $Z^2$ is a group of the formula (iv)

—NH—N=CHCy (iv)

wherein Cy is a $C_{3-7}$-cycloalkyl group, preferably cyclohexyl or a $C_{1-4}$ alkyl group, preferably isopropyl.

Preferably, in the compound of formula (III), $Z^2$ is a group of the formula (vii)

—C≡C-$Z^3$ (v)

wherein $Z^3$ is $C_3$-$C_{16}$ alkyl, hydroxy $C_2$-$C_6$ alkyl or (phenyl) (hydroxymethyl).

Specific examples of such compounds of formula (I) include WRC-0470, WRC-0474 [SHA 211], WRC-0090 and WRC-0018, shown below:

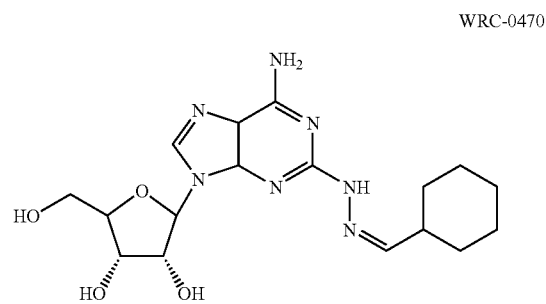
WRC-0470

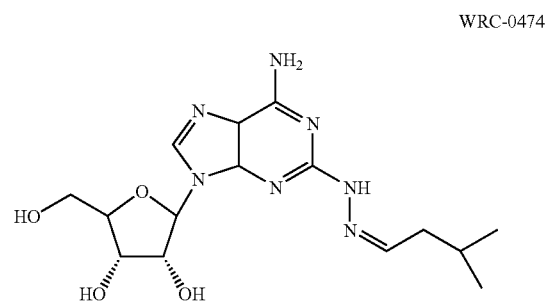
WRC-0474

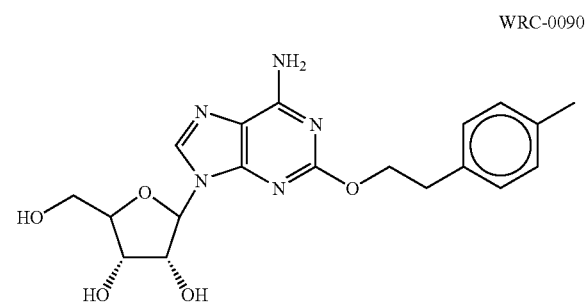
WRC-0090

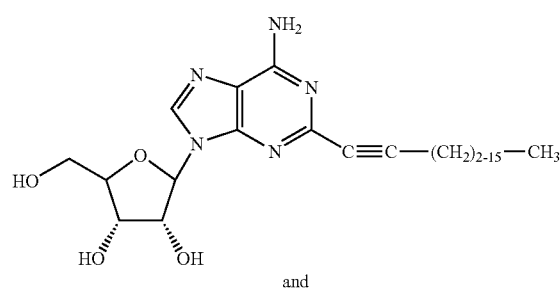

and

-continued

WRC-0018

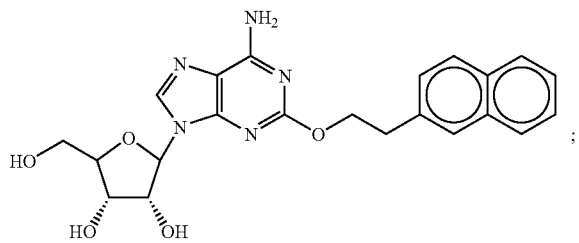

wherein the H on $CH_2OH$ can optionally be replaced by ethylaminocarbonyl. Of these specific examples, WRC-0474 [SHA 211] and WRC-0470 are particularly preferred.

Such compounds may be synthesized as described in: Olsson et al. (U.S. Pat. Nos. 5,140,015 and 5,278,150); Cristalli (U.S. Pat. No. 5,593,975); Miyasaka et al. (U.S. Pat. No. 4,956,345); Hutchinson, A. J. et al., *J. Pharmacol. Exp. Ther.*, 251, 47 (1989); Olsson, R. A. et al., *J. Med. Chem.*, 29, 1683 (1986); Bridges, A. J. et al., *J. Med. Chem.*, 31, 1282 (1988); Hutchinson, A. J. et al., *J. Med. Chem.*, 33, 1919 (1990); Ukeeda, M. et al., *J. Med. Chem.*, 34, 1334 (1991); Francis, J. E. et al., *J. Med. Chem.*, 34, 2570 (1991); Yoneyama, F. et al., *Eur. J. Pharmacol.*, 213, 199-204 (1992); Peet, N. P. et al., *J. Med. Chem.*, 35, 3263 (1992); and Cristalli, G. et al., *J. Med. Chem.*, 35, 2363 (1992); all of which are incorporated herein by reference.

Another embodiment includes compounds having formula (III) where $Z^2$ is a group having formula (vi):

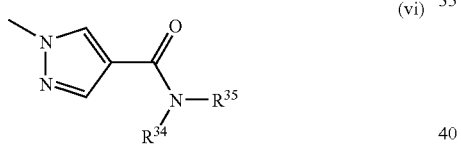

(vi)

wherein $R^{34}$ and $R^{35}$ are independently H, $C_1$-$C_6$ alkyl, $C_3$-$C_7$ cycloalkyl, phenyl, phenyl $C_1$-$C_3$ alkyl or $R^{34}$ and $R^{35}$ taken together with the nitrogen atom are a 5- or 6-membered heterocyclic ring containing 1-2 heteroatoms selected from non-peroxide oxygen, nitrogen ($N(R^{13})$) or sulphur atoms. Preferably one of $R^{34}$ and $R^{35}$ is hydrogen and the other is ethyl, methyl or propyl. More preferably one of $R^{34}$ and $R^{35}$ is hydrogen and the other is ethyl or methyl.

The 2-(pyrazol-1-yl)adenosine compounds of the invention, wherein $Z^2$ is a group having formula (vi), can be prepared by reacting a 2-chloro- or 2-iodo adenosine derivative with an 1H-pyrazole-4-carboxamides compound having formula (vii):

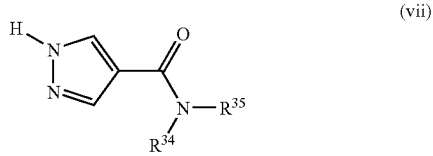

(vii)

where $R^{34}$ and $R^{35}$ are as described above, wherein selective protection/deprotection of the amido group is used as needed.

A specific pyrazole derivative useful in practicing this invention is a compound having the formula:

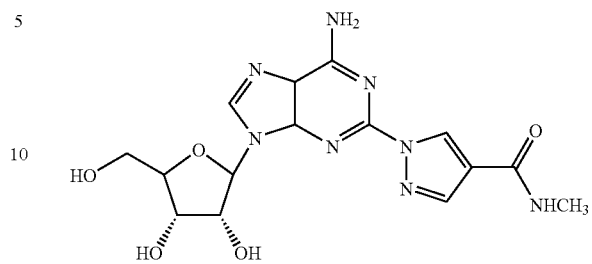

The 1H-pyrazole-4-carboxamides can be prepared starting with 1H-pyrazole-4-carboxylic acid, available from Aldrich Chemical Co. In the first step, the acid is converted to an ester, e.g., a methyl or ethyl ester. The ester converted to the amide via aminolysis, e.g., with methylamine to form the methyl amide. The pyrazole-4-carboxamide will react with the 2-halopurines in the presence of a strong base to provide the 2-(pyrazol-1-yl)adenosine compounds having formula (III).

Another specific group of agonists of $A_{2A}$ adenosine receptors that are useful in the practice of the present invention include compounds having the general formula (IV):

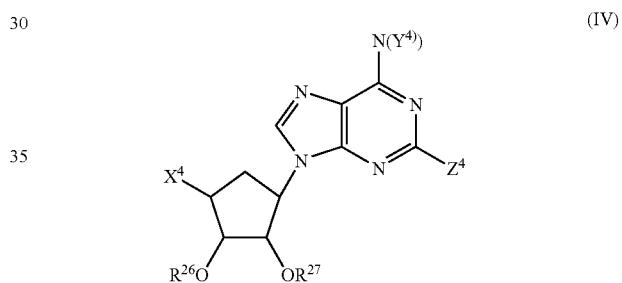

(IV)

wherein $Z^4$ is $-NR^{28}R^{29}$;
$R^{28}$ is hydrogen or $(C_1$-$C_4)$alkyl; and $R^{29}$ is a) $(C_1$-$C_4)$alkyl;

b) $(C_1$-$C_4)$alkyl substituted with one or more $(C_1$-$C_4)$ alkoxy, halogen, hydroxy, amino, mono($(C_1$-$C_4)$alkyl) amino, di($(C_1$-$C_4)$alkyl)amino or $(C_6$-$C_{10})$aryl wherein aryl is optionally substituted with one or more halogen, hydroxy, amino, $(C_1$-$C_4)$alkyl, $R^{30}OOC$—$((C_1$-$C_4)$ alkyl)-, $R^{31}$ $R^{32}NC(=O)$—$((C_1$-$C_4)$alkyl)-, mono $((C_1$-$C_4)$alkyl)amino or di($(C_1$-$C_4)$alkyl)amino;

c) $(C_6$-$C_{10})$aryl; or d) $(C_6$-$C_{10})$aryl substituted with one or more halogen, hydroxy, amino, mono($(C_1$-$C_4)$alkyl)amino, di($(C_1$-$C_4)$ alkyl)amino or $(C_1$-$C_4)$alkyl;

wherein each $Y^4$ is individually H, $(C_1$-$C_6)$alkyl, $(C_3$-$C_7)$ cycloalkyl, phenyl or phenyl($C_1$-$C_3)$alkyl; and $X^4$ is $-C(=O)NR^{31}R^{32}$, $-COOR^{30}$, or $-CH_2OR^{30}$;

wherein each of $R^{31}$ and $R^{32}$ are independently; hydrogen; $C_{3-7}$-cycloalkyl; $(C_1$-$C_4)$alkyl; $(C_1$-$C_4)$alkyl substituted with one or more $(C_1$-$C_4)$alkoxy, halogen, hydroxy, $-COOR^{33}$, amino, mono($(C_1$-$C_4)$alkyl)amino, di($(C_1$-$C_4)$alkyl)amino or $(C_6$-$C_{10})$aryl wherein aryl is optionally substituted with one or more halogen, $(C_1$-$C_4)$alkyl, hydroxy, amino, mono ($(C_1$-$C_4)$alkyl)amino or di($(C_1$-$C_4)$alkyl)amino; $(C_6$-$C_{10})$ aryl; or $(C_6\text{-}C_{10})$aryl substituted with one or more halogen, hydroxy, amino, mono$((C_1\text{-}C_4)$alkyl)amino, di$((C_1\text{-}C_4)$alkyl)amino or $(C_1\text{-}C_4)$alkyl;

$R^{26}$ and $R^{27}$ independently represent hydrogen, lower alkanoyl, lower alkoxy-lower alkanoyl, aroyl, carbamoyl or mono- or di-lower alkylcarbamoyl; and $R^{30}$ and $R^{33}$ are independently hydrogen, $(C_1\text{-}C_4)$alkyl, $(C_6\text{-}C_{10})$aryl or $(C_6\text{-}C_{10})$aryl$((C_1\text{-}C_4)$alkyl); or a pharmaceutically acceptable salt thereof.

In one embodiment of formula (IV), at least one of $R^{28}$ and $R^{29}$ is $(C_1\text{-}C_4)$alkyl substituted with one or more $(C_1\text{-}C_4)$alkoxy, halogen, hydroxy, amino, mono$((C_1\text{-}C_4)$alkyl)amino, di$((C_1\text{-}C_4)$alkyl)amino or $(C_6\text{-}C_{10})$aryl wherein aryl is optionally substituted with one or more halogen, hydroxy, amino, $(C_1\text{-}C_4)$alkyl, $R^{30}$OOC—$(C_1\text{-}C_4)$alkyl, mono$((C_1\text{-}C_4)$alkyl)amino or di$((C_1\text{-}C_4)$alkyl)amino.

In another embodiment, at least one of $R^{31}$ and $R^{32}$ is $C_{1\text{-}4}$alkyl substituted with one or more $(C_1\text{-}C_4)$alkoxy, halogen, hydroxy, amino, mono$((C_1\text{-}C_4)$alkyl)amino, di$((C_1\text{-}C_4)$alkyl)amino or $C_{6\text{-}10}$-aryl wherein aryl is optionally substituted with one or more halogen, hydroxy, amino, $(C_1\text{-}C_4)$alkyl, $R^{30}$OOC—$(C_1\text{-}C_4)$alkylene-, mono$((C_1\text{-}C_4)$alkyl)amino or di$((C_1\text{-}C_4)$alkyl)amino.

In another embodiment, at least one of $R^{28}$ and $R^{29}$ is $C_{6\text{-}10}$-aryl substituted with one or more halogen, hydroxy, amino, mono$((C_1\text{-}C_4)$alkyl)amino, di$((C_1\text{-}C_4)$alkyl)amino or $(C_1\text{-}C_4)$alkyl.

In another embodiment, at least one of $R^{31}$ and $R^{32}$ is $C_{6\text{-}10}$-aryl substituted with one or more halogen, hydroxy, amino, mono$((C_1\text{-}C_4)$alkyl)amino, di$((C_1\text{-}C_4)$alkyl)amino or $(C_1\text{-}C_4)$alkyl.

In a specific combination, $R^{31}$ is hydrogen and $R^{32}$ is $(C_1\text{-}C_4)$alkyl, cyclopropyl or hydroxy-$(C_2\text{-}C_4)$alkyl. A specific $R^{28}$ group is $(C_1\text{-}C_4)$alkyl substituted with $(C_6\text{-}C_{10})$aryl, that is in turn substituted with $R^{30}$O(O)C—$(C_1\text{-}C_4)$alkylene-.

A specific compound having formula (IV) is:

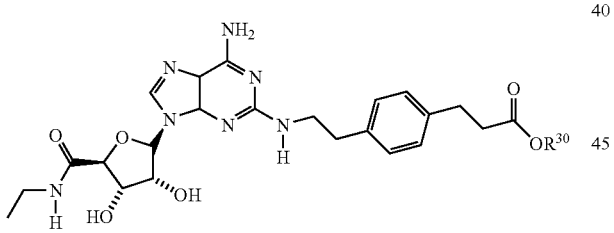

wherein $R^{30}$ is hydrogen, methyl, ethyl, n-propyl or isopropyl. More preferred is a compound wherein the $R^{30}$ group is methyl or ethyl. The most preferred $R^{30}$ group is methyl.

Two compounds that are particularly useful in practicing the present invention have the formula:

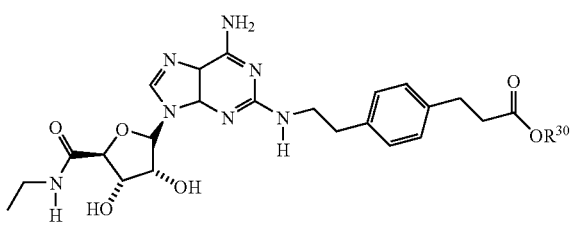

wherein $R^{30}$ is hydrogen (acid, CGS21680) and where $R^{30}$ is methyl (ester, JR2171).

The compounds of the invention having formula (IV) may be synthesized as described in: U.S. Pat. No. 4,968,697 or *J. Med. Chem.*, 33, 1919-1924, (1990).

Specifically, the invention also provides the use of a compound of formula (I) or a pharmaceutically acceptable salt thereof to prepare a medicament for treating systemic intoxification in a mammal (e.g. a human),.

Specifically, the invention also provides the use of a compound of formula (I) or a pharmaceutically acceptable salt thereof to prepare a medicament for treating inflammation caused by bacterial, fungal or viral infections and the inflammation caused by the treatment of these infections, e.g., by the death of the bacterial or viral cells in a mammal (e.g. a human).

The present method also includes the administration of a Type IV phosphodiesterase (PDE) inhibitor in combination with compounds having formulae (I), (I), (III), and (IV). The combination of the compounds of the invention with type IV phosphodiesterase inhibitor provides synergistic decreases in the inflammatory response of immune cells. Examples of Type IV phosphodiesterase (PDE) inhibitors include those disclosed in U.S. Pat. No. 4,193,926, and WO 92-079778, and Molnar-Kimber, K. L. et al., *J. Immunol.*, 150, 295A (1993), all of which are incorporated herein by reference.

Suitable Type IV phosphodiesterase (PDE) inhibitors include racemic and optically active 4-(polyalkoxyphenyl)-2-pyrrolidones of general formula (VI):

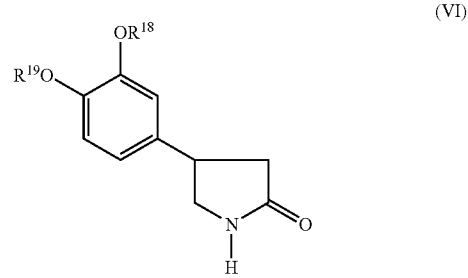

(disclosed and described in U.S. Pat. No. 4,193,926) wherein $R^{18}$ and $R^{19}$ are independently the same or different and are hydrocarbon radicals having up to 18 carbon atoms with at least one being other than methyl, a heterocyclic ring, or alkyl of 1-5 carbon atoms which is substituted by one or more of halogen atoms, hydroxy, carboxy, alkoxy, alkoxycarbonyl or an amino group or amino.

Examples of hydrocarbon $R^{18}$ and $R^{19}$ groups are saturated and unsaturated, straight-chain and branched alkyl of 1-18, preferably 1-5, carbon atoms, cycloalkyl and cycloalkylalkyl, preferably 3-7 carbon atoms, and aryl and aralkyl, preferably of 6-10 carbon atoms, especially monocyclic.

Rolipram is an example of a suitable Type IV phosphodiesterase or PDE inhibitor included within the above formula. Rolipram has the following formula:

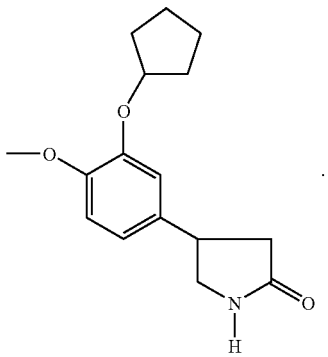

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Compounds of the present invention can conveniently be administered in a pharmaceutical composition containing the compound in combination with a suitable excipient. Such pharmaceutical compositions can be prepared by methods and contain excipients which are well known in the art. A generally recognized compendium of such methods and ingredients is Remington's Pharmaceutical Sciences by E. W. Martin (Mark Publ. Co., 15th Ed., 1975). The compounds and compositions of the present invention can be administered parenterally (for example, by intravenous, intraperitoneal or intramuscular injection), topically, orally, or rectally.

For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The compounds or compositions can also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

Pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The compound is conveniently administered in unit dosage form; for example, containing about 0.05 mg to about 500 mg, conveniently about 0.1 mg to about 250 mg, most conveniently, about 1 mg to about 150 mg of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The compositions can conveniently be administered orally, sublingually, transdermally, or parenterally at dose levels of about 0.01 to about 150 µg/kg, preferably about 0.1 to about 50 µg/kg, and more preferably about 0.1 to about 10 µg/kg of mammal body weight.

The surgical techniques for transplanting organs are known to the person skilled in the art of organ transplantation.

For parenteral administration the compounds are presented in aqueous solution in a concentration of from about 0.1 to about 10%, more preferably about 0.1 to about 7%. The solution may contain other ingredients, such as emulsifiers, antioxidants or buffers.

The preparation of compounds useful in practicing the present invention are disclosed in U.S. patent application Ser. No. 10/236,379, filed Oct. 1, 2002, and can generally be prepared as illustrated in Schemes 1A and 1B below. Starting materials can be prepared by procedures described in these schemes, procedures described in the General methods below or by procedures that would be well known to one of ordinary skill in organic chemistry. The variables used in Schemes 1A and Scheme 1B are as defined herein or as in the claims.

The preparation of alkynyl cycloalkanols is illustrated in Scheme 1A. A solution of an appropriate cycloalkanone (where j is from 0-5) is prepared in a solvent such as THF. A solution of a suitable ethynylmagnesium halide compound in a solvent is added to the cycloalkanone. After addition, the solution is allowed to stir at about 20 C for about 20 hours. The reaction is monitored via TLC until the starting material is consumed. The reaction is quenched with water, filtered over a plug of sand and silica, washed with a solvent, such as EtOAc, and evaporated to provide the product. Typically, two products are formed, the isomers formed by the axial/equatorial addition of the alkyne (where m is as defined above, and the sum of m1 and m2 is from 0 to about 7) to the ketone. The compounds are purified via flash chromatography using EtOAc/Hexanes to provide the product.

Scheme 1A

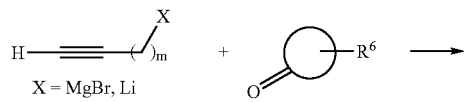

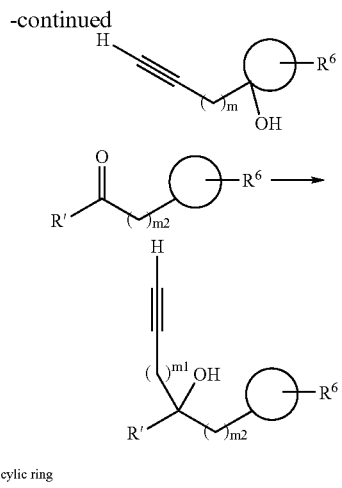

In accordance with one embodiment of the present invention a composition comprising an agonist of $A_{2A}AR$ is administered to a patient to treat septic shock and systemic inflammatory response syndrome. As used herein the term "treating" includes prophylaxis of the specific disorder or condition, or alleviation of the symptoms associated with a specific disorder or condition and/or preventing or eliminating said symptoms. In one embodiment a method for treating septic shock or systemic inflammatory response syndrome is provided wherein an agonist of $A_{2A}ARs$ is administered to a patient to reduce inflammation and improve survival in a patient suffering from septic shock or systemic inflammatory response syndrome. In one embodiment the $A_{2A}AR$ agonist is selected from the group consisting of ATL146e, AB-1, AB-3 and JR-3213.

The preparation of 2-alkynyladenosines is illustrated in Scheme 1B. A flame-dried round bottom under nitrogen is charged with 5-(6-Amino-2-iodo-purin-9-yl)-3,4-dihydroxytetrahydrofuran-2-carboxylic acid ethylamide (NECA 2-Iodoadenosine) and a solvent such as DMF. The appropriate alkyne, wherein R is a —$(CR^1R^2)_m$ Z group, is dissolved in acetonitrile followed by TEA, 5 mole % $Pd(PPh_3)_4$, and CuI. All solvents are thoroughly degassed.

The solution is allowed to stir for about 24 hours at room temperature, and monitored until complete by HPLC. If the reaction is not complete after this time, additional catalyst, CuI, and TEA are added. After the reaction is complete, the solvents are removed under high-vacuum and the residue taken up in a small amount of DMF. This product is isolated using preparative silica TLC. The product is purified by RP-HPLC.

Scheme 1B

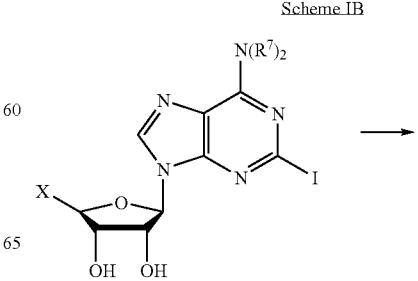

-continued

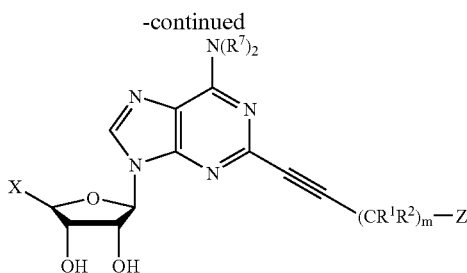

The following abbreviations have been used herein:
2-Aas 2-alkynyladenosines;
$^{125}$I-ABA N$^6$-(4-amino-3-$^{125}$iodo-benzyl)adenosine
APCI Atmospheric pressure chemical ionization
ATL146e 4-{3-[6-Amino-9-(5-ethylcarbamoyl-3,4-dihydroxy-tetrahydro-furan-2-yl)-9H-purin-2-yl]-prop-2-ynyl}cyclo-hexanecarboxylic acid methyl ester;
CCPA 2-chloro-N$^6$-cyclopentyladenosine;
CGS21680 2-[4-(2-carboxyethyl)phenethylamino]-5'-N-ethyl-carboxamidoadenosine;
Cl-IB-MECA N$^6$-3-iodo-2-chlorobenzyladenosine-5'-N-methyl-uronamide;
CPA N$^6$-cyclopentyladenosine
DMF dimethylformamide
DMSO dimethylsulfoxide
DMSO-d$_6$ deuterated dimethylsulfoxide
EtOAc ethyl acetate
eq equivalent
GPCR G protein coupled receptor; hA$_{2A}$AR, Recombinant human A$_{2A}$ adenosine receptor;
IADO 2-Iodoadenosine
$^{125}$I-APE, 2-[2-(4-amino-3-[$^{125}$I]iodophenyl)ethylamino] adenosine;
NECA 5'-N-ethylcarboxamidoadenosine;
IB-MECA N$^6$-3-iodobenzyladenosine-5'-N-methyluronamide;
2-Iodoadenosine 5-(6-amino-2-iodo-purin-9-yl)-3,4-dihydroxytetra-hydro-furan-2carboxylic acid ethylamide
HPLC high-performance liquid chromatography
HRMS high-resolution mass spectrometry
$^{125}$I-ZM241385, $^{125}$I-4-(2-[7-amino-2-[2-furyl][1,2,4]triazolo[2,3-α]-[1,3,5]triazin-5-yl-amino]ethyl)phenol;
INECA 2-iodo-N-ethylcarboxamidoadenosine
LC/MS liquid chromatography/mass spectrometry
m.p. melting point
MHz megahertz
MRS 1220, N-(9-chloro-2-furan-2-yl-[1,2,4]triazolo[1,5-c]-quinazolin-5-yl)-2-phenylacetamide;
MS mass spectrometry
NECA N-ethylcarboxamidoadenosine
NMR nuclear magnetic resonance
RP-HPLC reverse phase high-performance liquid chromatography
TBAF tetrabutylammonium fluoride
TBS tert-butyldimethylsilyl
TBDMSCl tert-butyldimethylsilylchloride
TEA triethylamine
TFA trifluoroacetic acid
THF tetrahydrofuan
TLC thin layer chromatography
p-TSOH para-toluenesulfonic acid
XAC 8-(4-((2-a-minoethyl)aminocarbonyl-methyloxy)-phenyl)-1-3-dipropylxanthine.

EXAMPLES

Effects of A$_{2A}$AR agonists in in vivo studies

The effects of A$_{2A}$AR agonist, ATL146e were studied in a mouse islet transplant model. No mice in the control group were cured with 100 islets transplanted per mouse transplantation within 17 days after transplantation (See FIG. 1). In contrast, in ATL 146e treated group, (where ATL 146e was used at 10 ng/kg/min beginning with transplantation and lasting for 7 days, all mice were cured of diabetes within 17 days (See FIG. 2).

Figure 3:
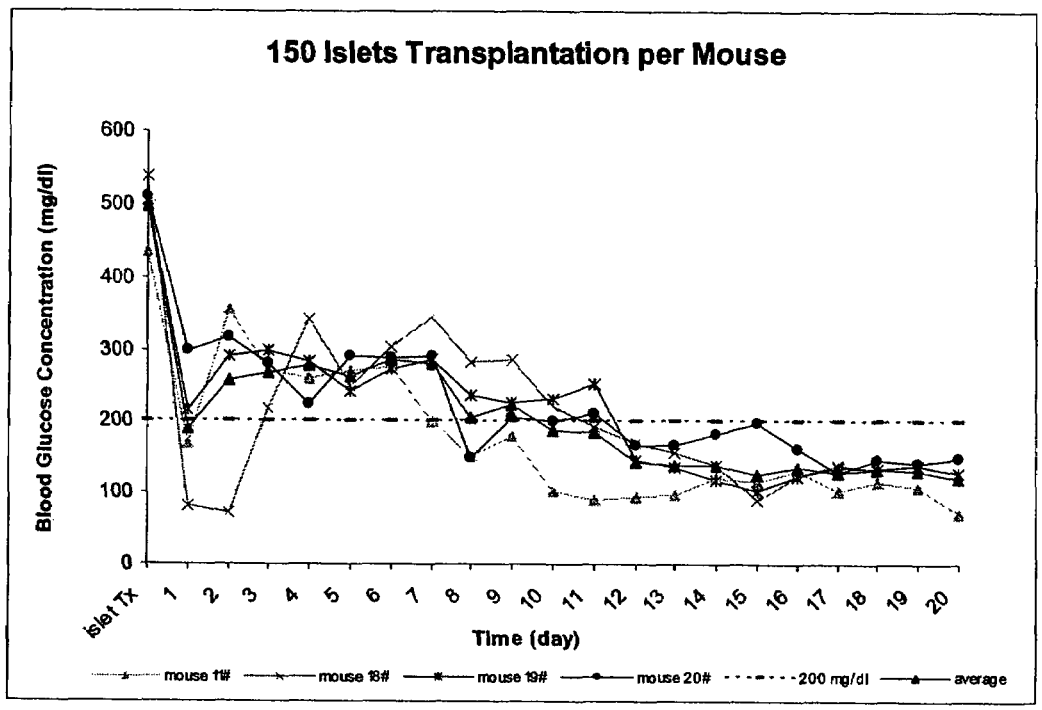
FIG. 3 shows blood glucose levels in mg/dL over time in a model for tissue rejection in mice, where the mice have received a transplant of 150 insulin-producing pancreatic islets, in the absence of any compound of the invention.
Figure 4:
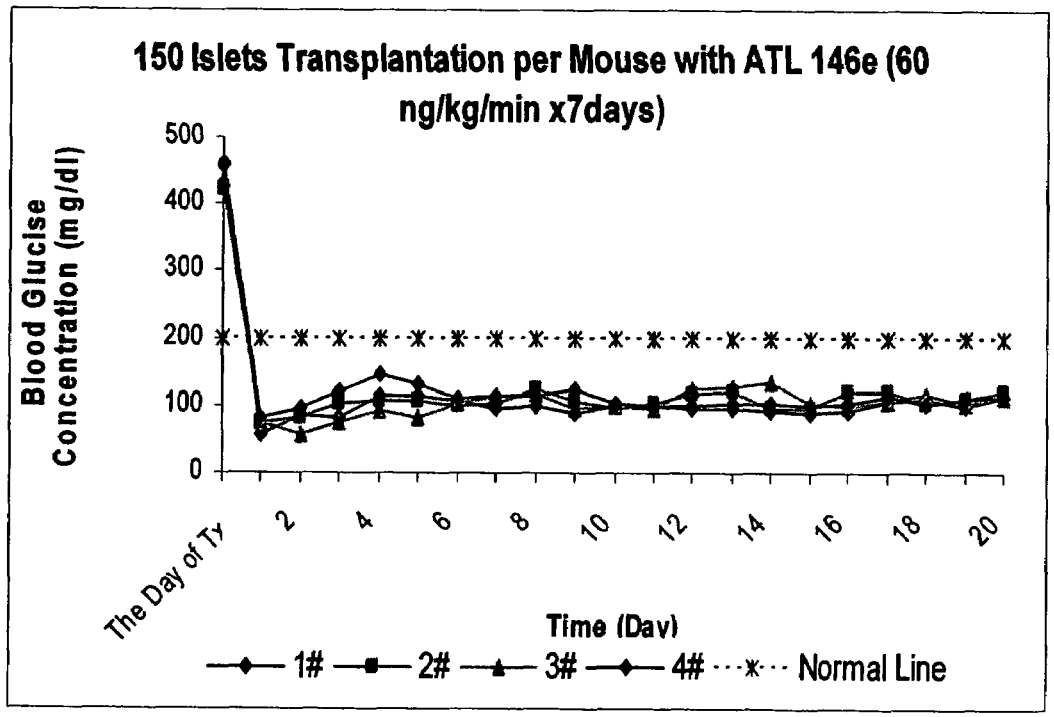
FIG. 4 shows blood glucose levels in mg/dL over time in a model for tissue rejection in mice, where the mice have received a transplant of 150 insulin-producing pancreatic islets, in the presence of inventive compound ATL146e at a dose of 60 ng/kg/min administered starting 1 day before the transplant then for 7 days.

When the dose of A$_{2A}$AR agonist, ATL 146e, was raised to 60 ng/kg/min and administered beginning 1 day before transplantation, diabetes was cured immediately with 150 islets transplanted per mouse (See FIG. 4). In contrast, without the A$_{2A}$AR agonist compound, it took almost 2 weeks to achieve normoglycemia (See FIG. 3).

Figure 2:
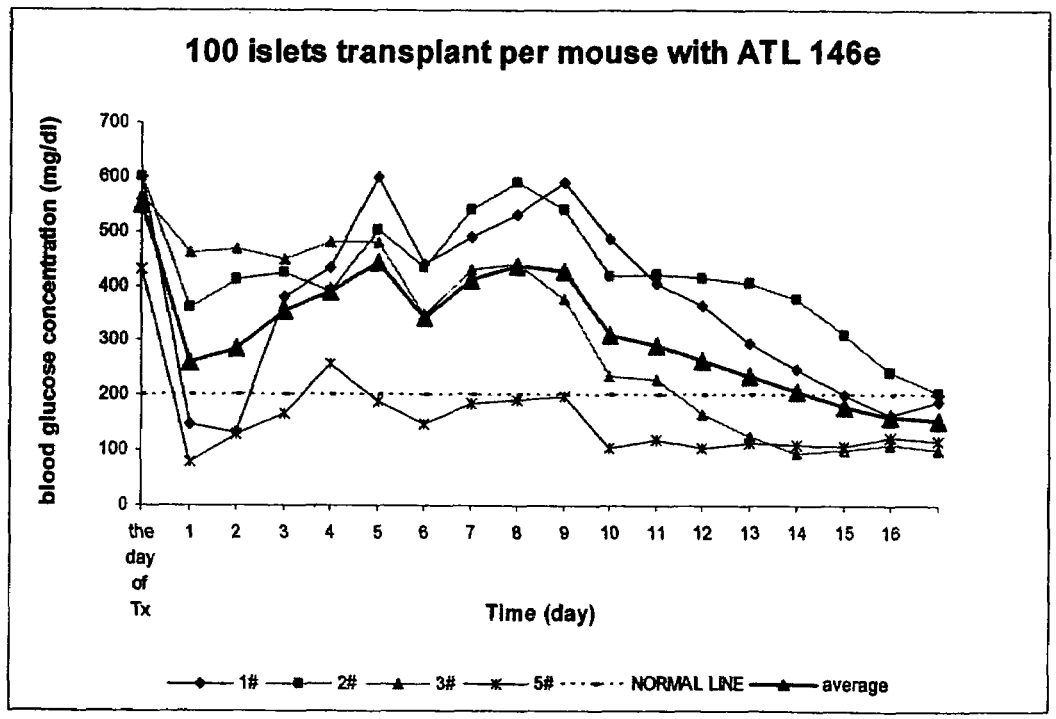
FIG. 2 shows blood glucose levels in mg/dL over time in a model for tissue rejection in mice, where the mice have received a transplant of 100 insulin-producing pancreatic islets, in the presence of inventive compound ATL146e at a dose of 10 ng/kg/min for 7 days.
Figure 5:
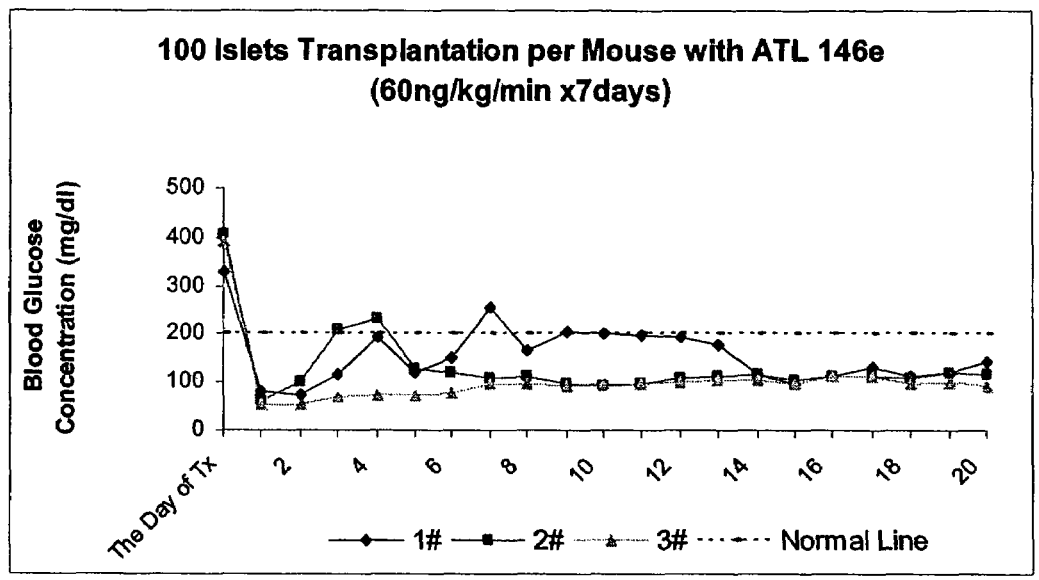
FIG. 5 shows blood glucose levels in mg/dL over time in a model for tissue rejection in mice, where the mice have received a transplant of 100 insulin-producing pancreatic islets, in the presence of inventive compound ATL146e at a dose of 60 ng/kg/min administered starting 1 day before the transplant then for 7 days.

When the A$_{2A}$AR agonist, ATL 146e (60 ng/kg/min), was administered 1 day before transplantation, diabetes was cured immediately with 100 islets per mouse (See FIG. 5). Compared to the previous data, where cure can not be achieved at this dose of islet tissue without ATL 146e (FIG. 1) or took two weeks to achieve at the lower dose (FIG. 2).

Figure 6:
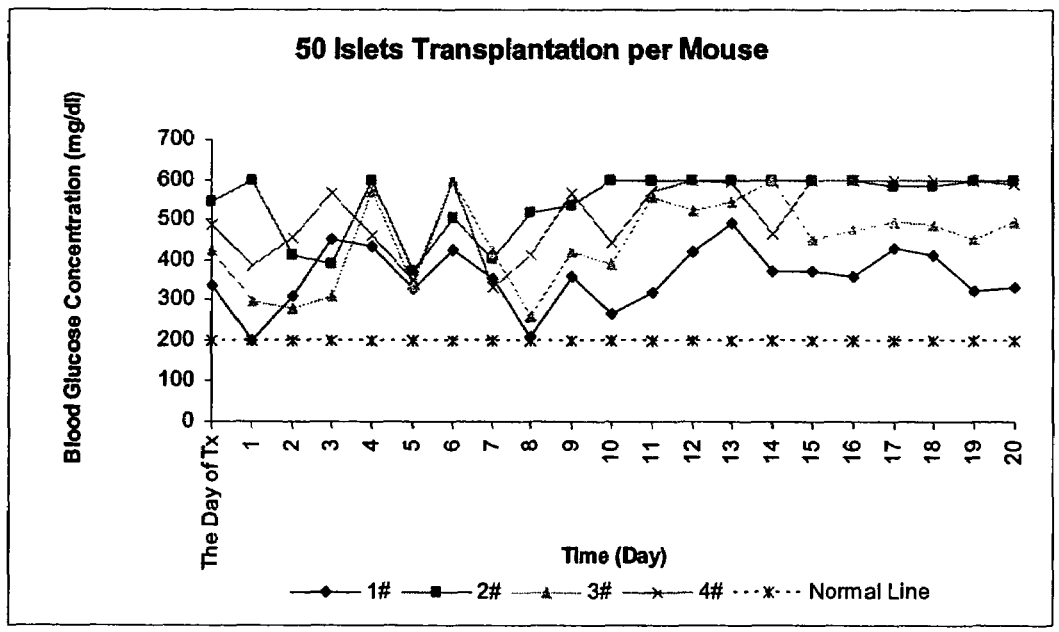
FIG. 6 shows blood glucose levels in mg/dL over time in a model for tissue rejection in mice, where the mice have received a transplant of 50 insulin-producing pancreatic islets, in the absence of any compound of the invention.
Figure 7:
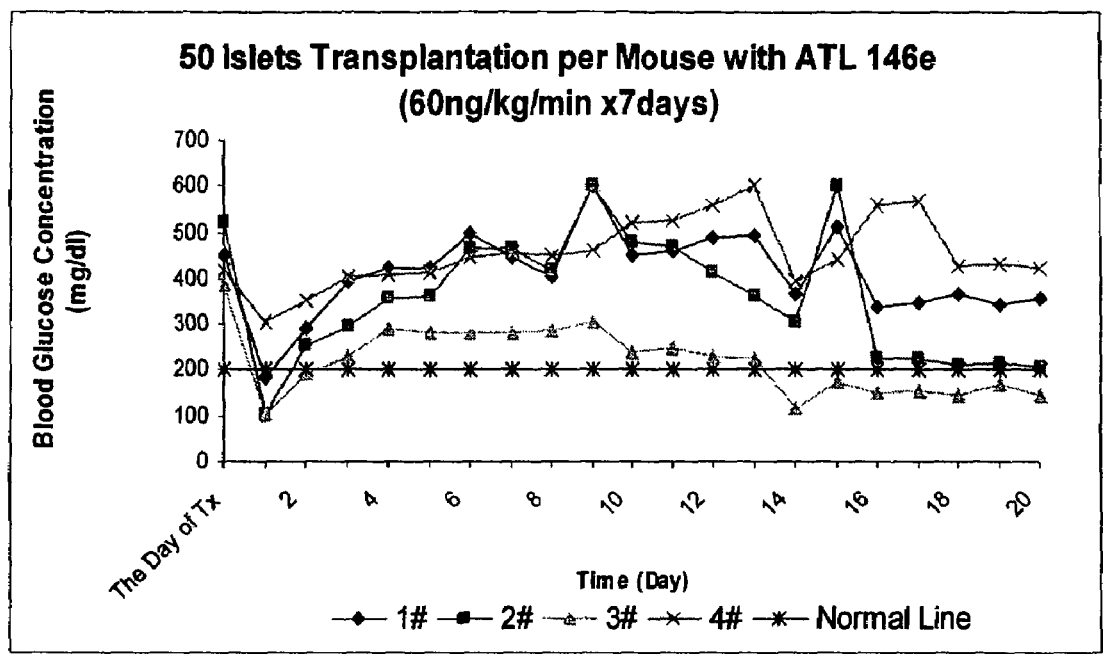
FIG. 7 shows blood glucose levels in mg/dL over time in a model for tissue rejection in mice, where the mice have received a transplant of 50 insulin-producing pancreatic islets, in the presence of inventive compound ATL146e at a dose of 60 ng/kg/min administered starting 1 day before the transplant then for 7 days.

For mice receiving only 50 islets, use of A$_{2A}$AR agonist, ATL 146e at a dose of 60 ng/kg/min, administered 1 day before transplantation also resulted in half of mice achieving normoglycemia by 14-17 days after transplantation (See FIG. 7). In contrast, in the absence of ATL 146e, diabetes can not be cured by 50 islets transplanted per mouse (FIG. 6).

In another experiment, a 50 islet transplant group was used, and the A$_{2A}$AR agonist, ATL 146e, was administered for 3 days prior to transplantation. This resulted in a cure within 7 days in 3 of 4 animals, i.e., the animals achieved normoglycemia.

All cited publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A therapeutic method for treating inflammation caused by an immune response to transplanted tissue, comprising the administration to a patient in need thereof an effective amount of an A$_{2A}$ adenosine receptor agonist, wherein the A$_{2A}$ adenosine receptor agonist is a compound of formula (I):

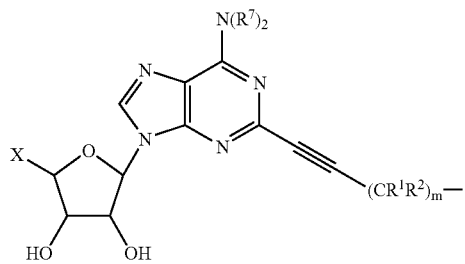

wherein
Z is CR$^3$R$^4$R$^5$;
each R$^1$ is hydrogen;
each R$^2$ is hydrogen;
R$^3$ is hydrogen;

R⁴ and R⁵ together with the atom to which they are attached form a saturated mono- or bicyclic cycloalkyl ring having 3, 4, 5, 6, 7, 8, 9 or 10 ring atoms wherein the cycloalkyl optionally comprises 1-2 N, O, or S;

wherein any ring comprising R⁴ and R⁵ is substituted with from 1 to 3 R⁶ groups; wherein each R⁶ is independently (C₁-C₆)alkyl, CH₂OH, —CO₂Rᵃ,RᵃC(=O)O—, or RᵇRᶜNC(=O)—;

wherein any of the alkyl groups of R⁶ is optionally substituted on carbon with a substituent selected from the group consisting of CH₂OH, —CO₂Rᵃ,RᵃC(=O)O—, and RᵇRᶜNC(=O)—;

each R⁷ is independently hydrogen, (C₁-C₆)alkyl, (C₃-C₇)cycloalkyl, phenyl or phenyl(C₁-C₃)alkylene;

X is —CH₂OH, —CO₂Rᵃ, —OC(O)Rᵃ, —CH₂OC(O)Rᵃ, or —C(O)NRᵇRᶜ;

each Rᵃ, Rᵇ and Rᶜ is independently hydrogen, (C₁-C₆)alkyl, or (C₁-C₆)alkyl substituted with 1-3 (C₁-C₆)alkoxy, (C₃-C₆)cycloalkyl, (C₁-C₆)alkylthio, aryl or aryl (C₁-C₆)alkylene; and m is 0 to 6;

or a pharmaceutically acceptable salt thereof.

2. The method of claim 1, wherein the immune response is a transplant rejection, or graft versus host disease.

3. The method of claim 2, wherein the immune response is a transplant rejection.

4. The method of claims 1 or 2, wherein the transplantation comprises an organ, tissue or cell transplantation.

5. The method of claim 4, wherein the cells are bone marrow, skin, or pancreatic islets.

6. The method of claim 5, wherein the cells are pancreatic islets.

7. The method of claim 4, wherein the organ is a cornea, kidney, lung, liver, or heart.

8. The method of claim 1, wherein the ring comprising R⁴, R⁵ and the atom to which they are connected is cyclopentane, cyclohexane, piperidine, piperazine, decaline, hexahydro-pyrimidine, imidazolidine, or pyrazolidine.

9. The method of claim 8, wherein the ring comprising R⁴, R⁵ and the atom to which they are connected is cyclopentane, cyclohexane, piperidine, piperazine, hexahydro-pyrimidine, imidazolidine, or pyrazolidine.

10. The method of claim 9, wherein the ring comprising R⁴ and R⁵ and the atom to which they are connected is cyclohexane, piperidine or piperazine.

11. The method of claim 1, wherein R⁶ is —CO₂Rᵃ, RᵃC(=O)O—, or RᵇRᶜNC(=O)—.

12. The method of claim 1, wherein R⁶ is methyl, ethyl, t-butyl, —CO₂Rᵃ or CONRᵇRᶜ.

13. The method of claim 1, wherein R⁶ is —CH₂OH, —CH₂OAc, -or CH₂C(=O)OCH₃.

14. The method of claim 1, wherein Rᵃ and Rᵇ are independently hydrogen, methyl, ethyl, phenyl or benzyl.

15. The method of claim 1, wherein Rᵃ is (C₁-C₆)alkyl.

16. The method of claim 1, wherein Rᵃ is methyl, ethyl, propyl or butyl.

17. The method of claim 1, wherein Rᵃ is, methyl, ethyl, i-propyl, i-butyl or tert-butyl.

18. The method of claim 1, wherein R⁷ is hydrogen, or alkyl.

19. The method of claim 1, wherein R⁷ is hydrogen, methyl or ethyl.

20. The method of claim 19, wherein R⁷ is H, or methyl.

21. The method of claim 1, wherein N(R⁷)₂ is amino, methylamino, dimethylamino; ethylamino; pentylamino, diethylamino or benzylamino.

22. The method of claim 1, wherein N(R⁷)₂ is amino, or methylamino.

23. The method of claim 1, wherein X is —CH₂OH or —C(O)NRᵇRᶜ.

24. The method of claim 23, wherein X is —C(O)NHCH₂CH₃.

25. The method of claim 1, wherein m is 1 or 2.

26. The method of claim 1, wherein the rings comprising R⁴, R⁵ and the atom to which they are connected are selected from the group consisting of:

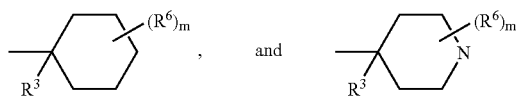

where m is from 1 to 3.

27. The method of claim 1, wherein the rings comprising R⁴, R⁵ and the atom to which they are connected are selected from the group consisting of:

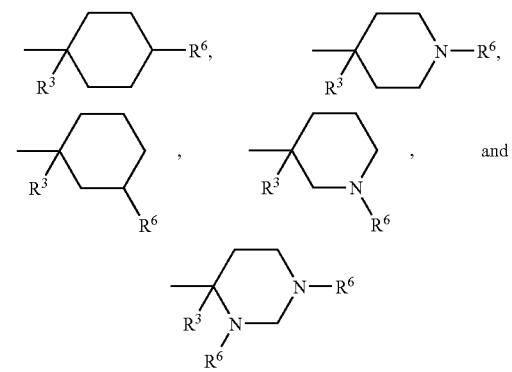

28. The method of claim 1, wherein the ring comprising R⁴ and R⁵ is 2-methylcyclohexane, 2,2-dimethylcyclohexane, 2-ethylcyclohexane, 2,2-diethylcyclohexane, 2-tert-butylcyclohexane, 3-methylcyclohexane, 3,3-dimethylcyclohexane, 4-methylcyclohexane, 4-ethylcyclohexane, 4-tert-butylcyclohexane, 4-carboxymethyl cyclohexane, 4-carboxyethyl cyclohexane, 3,3,5,5-tetramethyl cyclohexane, 2,4-dimethyl cyclopentane, 4-cyclohexanecarboxylic acid, or 4-cyclohexanecarboxylic acid esters.

29. The method of claim 1, wherein the ring comprising R⁴ and R⁵ is 4-piperidine, 4-piperidene-1-carboxylic acid, 4-piperidine-1-carboxylic acid methyl ester, 4-piperidine-1-carboxylic acid ethyl ester, 4-piperidine-1-carboxylic acid propyl ester, 4-piperidine-1-carboxylic acid tert-butyl ester, 3-piperidine, 3-piperidene-1-carboxylic acid, 3-piperidine-1-carboxylic acid methyl ester, or 3-piperidine-1-carboxylic acid tert-butyl ester.

30. The method of claim 1, wherein the $A_{2A}$ adenosine receptor agonist is:
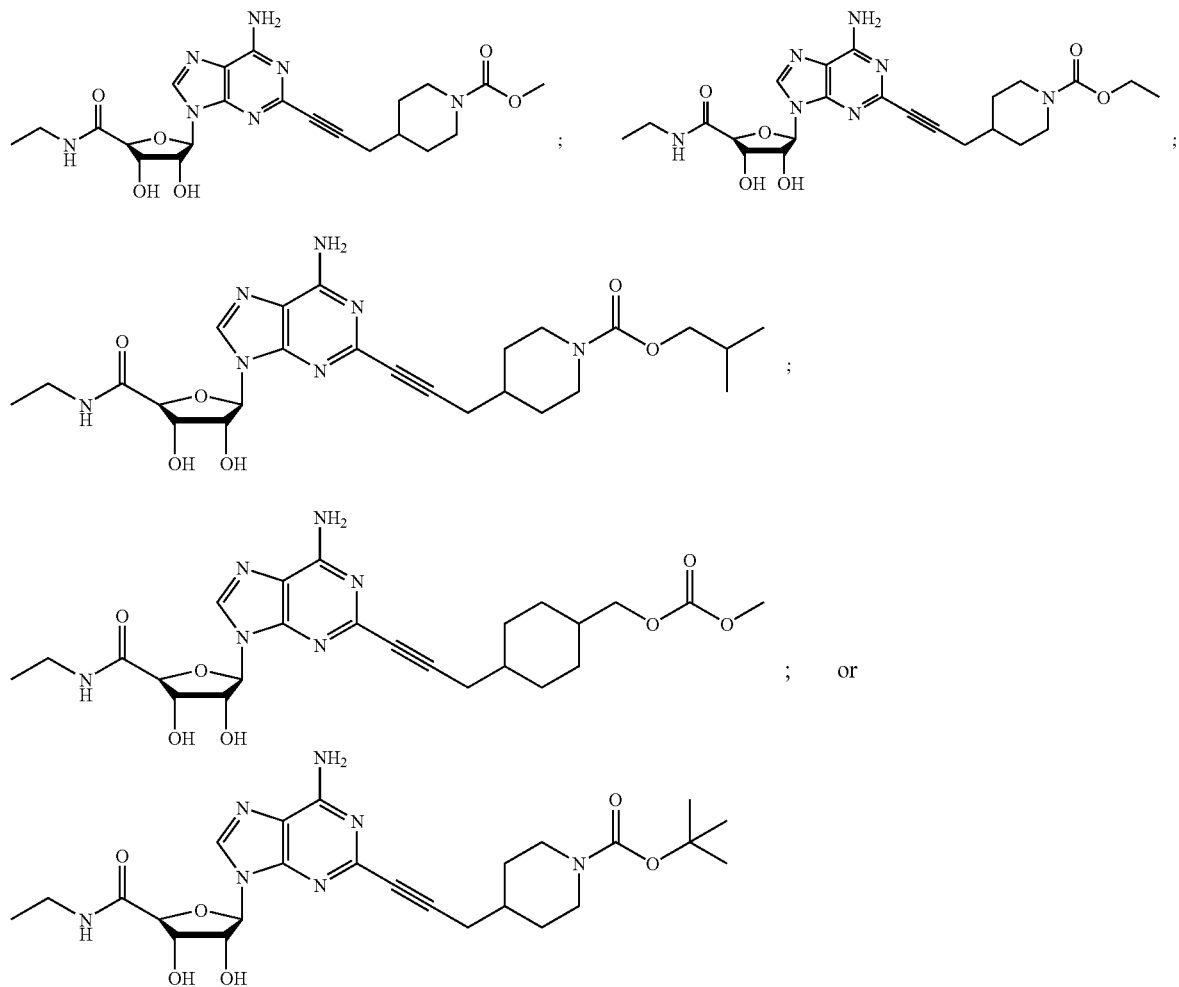
31. The method of claim 1, wherein the $A_{2A}$ adenosine receptor agonist is
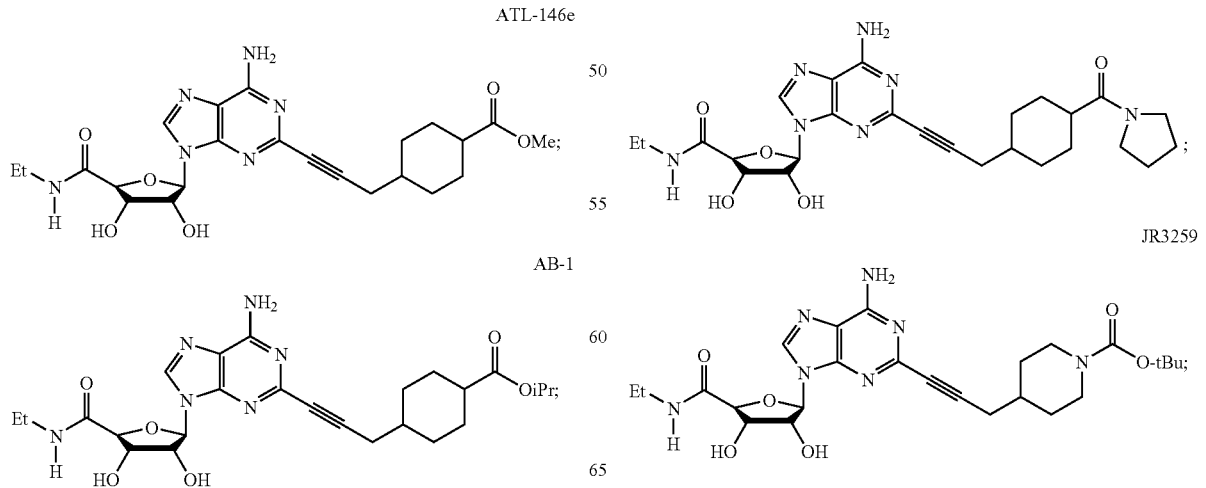

-continued
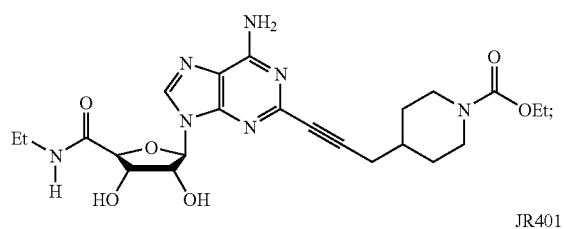
JR3269
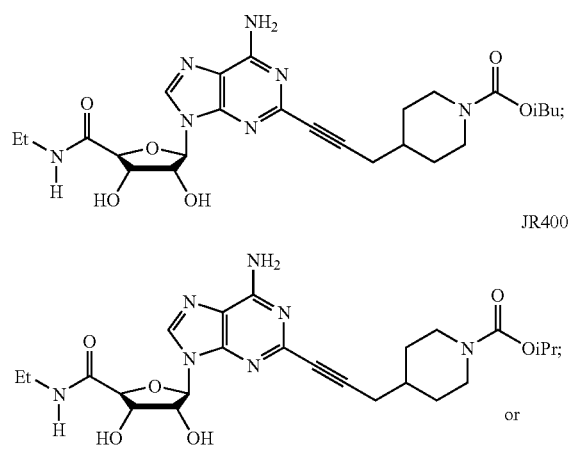
JR4011
JR4009
or
-continued
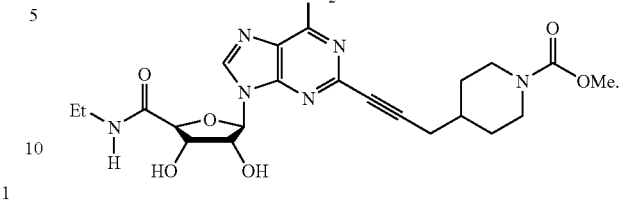
JR4007
32. The method of claim 31, wherein the $A_{2A}$ adenosine receptor agonist is the compound:
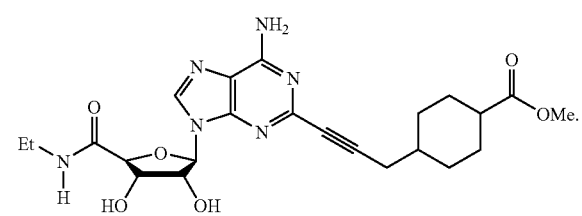
33. The method of claim 1, wherein the $A_{2A}$ adenosine receptor C agonist is administered by operation of a pump.
* * * * *